US012667356B1

(12) United States Patent
Bruns et al.

(10) Patent No.: US 12,667,356 B1
(45) Date of Patent: Jun. 30, 2026

(54) SURGICAL STAPLER WITH DISCRETELY POSITIONABLE DISTAL TIP

(71) Applicant: Cilag GmbH International, Zug (CH)

(72) Inventors: Jeffery Bruns, Cincinnati, OH (US); Nicholas A. Wilson, Montgomery, OH (US); Nicholas Fanelli, Morrow, OH (US); Kevin Fiebig, Cincinnati, OH (US); John May, Milford, OH (US); Marissa Talia Kamenir, Cincinnati, OH (US)

(73) Assignee: Cilag GmbH International, Zug (CH)

( * ) Notice: Subject to any disclaimer, the term of this patent is extended or adjusted under 35 U.S.C. 154(b) by 0 days.

(21) Appl. No.: 19/070,888

(22) Filed: Mar. 5, 2025

(51) Int. Cl.
　　*A61B 17/072* (2006.01)
　　*A61B 17/00* (2006.01)

(52) U.S. Cl.
　　CPC ................. *A61B 17/07207* (2013.01); *A61B 2017/00526* (2013.01); *A61B 2017/00862* (2013.01); *A61B 2017/07264* (2013.01); *A61B 2017/07271* (2013.01); *A61B 2017/07278* (2013.01); *A61B 2017/07285* (2013.01)

(58) Field of Classification Search
　　CPC .... A61B 17/07207; A61B 2017/00526; A61B 2017/00862; A61B 2017/07264; A61B 2017/07271; A61B 2017/07278; A61B 2017/07285
　　See application file for complete search history.

(56) References Cited

U.S. PATENT DOCUMENTS

| | | | |
|---|---|---|---|
| 2,887,111 | A | 5/1959 | Leyro |
| 4,608,981 | A | 9/1986 | Rothfuss et al. |
| 4,981,149 | A | 1/1991 | Yoon et al. |

(Continued)

FOREIGN PATENT DOCUMENTS

| | | |
|---|---|---|
| EP | 0537453 A1 | 4/1993 |
| EP | 2599452 A1 | 6/2013 |

(Continued)

OTHER PUBLICATIONS

European Search Report and Written Opinion dated Apr. 8, 2020 for Application No. EP 20154700.7, 12 pgs.

(Continued)

*Primary Examiner* — Michelle Lopez
(74) *Attorney, Agent, or Firm* — Lempia Summerfield Katz LLC

(57) ABSTRACT

An apparatus includes a first and second jaws (1404, 1406) that cooperate to clamp and staple tissue. The second jaw includes a jaw body (1408) and a distal tip (1410A, 1410B) pivotable relative to the jaw body between first and second discrete positions. The apparatus further includes first and second stops (1602, 1702A, 1702B, 1702C) configured to constrain the pivotable motion of the distal tip (1410A, 1410B), and a spring (1422) configured to exert a resilient force against a proximal protrusion (1414) of the distal tip in a first direction when in the first position and exert the resilient force against the proximal protrusion in a second, different, direction, when in the second position, the direc- (Continued)

tion of the resilient force of the spring exerted against the proximal protrusion transitioning from one of the first and second directions to the other when the distal tip is transitioned between positions.

31 Claims, 50 Drawing Sheets

(56)                    References Cited

U.S. PATENT DOCUMENTS

| | | | |
|---|---|---|---|
| 5,129,570 A | 7/1992 | Schulze et al. |
| 5,397,324 A | 3/1995 | Carroll et al. |
| 5,447,265 A | 9/1995 | Vidal et al. |
| 5,476,206 A | 12/1995 | Green et al. |
| 5,507,426 A | 4/1996 | Young et al. |
| 5,549,621 A | 8/1996 | Bessler et al. |
| 5,562,211 A | 10/1996 | Simons et al. |
| 5,649,957 A | 7/1997 | Levin |
| 5,766,187 A | 6/1998 | Sugarbaker |
| 5,772,099 A | 6/1998 | Gravener |
| 5,922,008 A | 7/1999 | Gimpelson |
| 5,941,442 A | 8/1999 | Geiste et al. |
| 6,241,740 B1 | 6/2001 | Davis et al. |
| 6,446,854 B1 | 9/2002 | Remiszewski et al. |
| 6,736,793 B2 | 5/2004 | Meyer et al. |
| 6,978,921 B2 | 12/2005 | Shelton, IV et al. |
| 7,000,818 B2 | 2/2006 | Shelton, IV et al. |
| 7,143,923 B2 | 12/2006 | Shelton, IV et al. |
| 7,300,444 B1 | 11/2007 | Nielsen et al. |
| 7,303,108 B2 | 12/2007 | Shelton, IV |
| 7,367,485 B2 | 5/2008 | Shelton, IV et al. |
| 7,380,695 B2 | 6/2008 | Doll et al. |
| 7,380,696 B2 | 6/2008 | Shelton, IV et al. |
| 7,404,508 B2 | 7/2008 | Smith et al. |
| 7,434,715 B2 | 10/2008 | Shelton, IV et al. |
| 7,588,177 B2 | 9/2009 | Racenet |
| 7,644,848 B2 | 1/2010 | Swayze et al. |
| 7,682,368 B1 | 3/2010 | Bombard et al. |
| 7,721,930 B2 | 5/2010 | Mckenna et al. |
| 7,866,523 B1 | 1/2011 | White et al. |
| 7,914,543 B2 | 3/2011 | Roth et al. |
| 8,066,166 B2 | 11/2011 | Demmy et al. |
| 8,136,711 B2 | 3/2012 | Beardsley et al. |
| 8,210,411 B2 | 7/2012 | Yates et al. |
| 8,348,123 B2 | 1/2013 | Scirica et al. |
| 8,403,195 B2 | 3/2013 | Beardsley et al. |
| 8,403,196 B2 | 3/2013 | Beardsley et al. |
| 8,408,439 B2 | 4/2013 | Huang et al. |
| 8,453,914 B2 | 6/2013 | Laurent et al. |
| 8,496,153 B2 | 7/2013 | Demmy et al. |
| 8,690,039 B2 | 4/2014 | Beardsley et al. |
| 8,714,429 B2 | 5/2014 | Demmy |
| 8,844,790 B2 | 9/2014 | Demmy et al. |
| 9,016,546 B2 | 4/2015 | Demmy et al. |
| 9,039,736 B2 | 5/2015 | Scirica et al. |
| 9,186,142 B2 | 11/2015 | Fanelli et al. |
| 9,433,416 B2 | 9/2016 | Beardsley et al. |
| 9,517,065 B2 | 12/2016 | Simms et al. |
| 9,522,004 B2 | 12/2016 | Demmy |
| 9,597,078 B2 | 3/2017 | Scirica et al. |
| 9,622,746 B2 | 4/2017 | Simms et al. |
| 9,713,470 B2 | 7/2017 | Scirica et al. |
| 9,717,497 B2 | 8/2017 | Zerkle et al. |
| 9,795,379 B2 | 10/2017 | Leimbach et al. |
| 9,808,248 B2 | 11/2017 | Hoffman |
| 9,839,421 B2 | 12/2017 | Zerkle et al. |
| 9,913,642 B2 | 3/2018 | Leimbach et al. |
| 9,936,952 B2 | 4/2018 | Demmy |
| 9,936,968 B2 | 4/2018 | Demmy et al. |
| 9,943,311 B2 | 4/2018 | Scirica et al. |
| 10,080,564 B2 | 9/2018 | Beardsley et al. |
| 10,092,292 B2 | 10/2018 | Boudreaux et al. |
| D833,010 S | 11/2018 | Harris et al. |
| D836,198 S | 12/2018 | Harris et al. |
| D836,199 S | 12/2018 | Schowalter et al. |
| 10,182,813 B2 | 1/2019 | Leimbach et al. |
| 10,507,032 B2 | 12/2019 | Demmy et al. |
| 10,779,827 B2 | 9/2020 | Scirica et al. |
| 10,786,252 B2 | 9/2020 | Harris et al. |
| 10,973,516 B2 | 4/2021 | Shelton, IV et al. |
| 11,103,244 B2 | 8/2021 | Harris et al. |
| 11,123,066 B2 | 9/2021 | Beardsley et al. |
| 11,185,327 B2 | 11/2021 | Harris et al. |
| 11,272,930 B2 | 3/2022 | Harris et al. |
| 11,304,697 B2 | 4/2022 | Fanelli et al. |
| 11,317,912 B2 | 5/2022 | Jenkins et al. |
| 11,439,391 B2 | 9/2022 | Bruns et al. |
| 11,564,684 B2 | 1/2023 | Harris et al. |
| 11,564,687 B2 | 1/2023 | Harris et al. |
| 2002/0065534 A1 | 5/2002 | Hermann et al. |
| 2002/0099375 A1 | 7/2002 | Hess et al. |
| 2004/0193186 A1 | 9/2004 | Kortenbach et al. |
| 2004/0243151 A1 | 12/2004 | Demmy et al. |
| 2010/0094315 A1 | 4/2010 | Beardsley et al. |
| 2011/0106150 A1 | 5/2011 | Hausen et al. |
| 2012/0143218 A1 | 6/2012 | Beardsley et al. |
| 2013/0334280 A1 | 12/2013 | Krehel et al. |
| 2014/0166723 A1 | 6/2014 | Beardsley et al. |
| 2018/0235610 A1 | 8/2018 | Harris et al. |
| 2018/0235611 A1 | 8/2018 | Harris et al. |
| 2018/0235619 A1 | 8/2018 | Harris et al. |
| 2019/0000481 A1 | 1/2019 | Harris et al. |
| 2019/0015100 A1 | 1/2019 | Yigit et al. |
| 2020/0015812 A1 | 1/2020 | Harris et al. |
| 2020/0015813 A1 | 1/2020 | Harris et al. |
| 2020/0015814 A1 | 1/2020 | Harris et al. |
| 2020/0015815 A1 | 1/2020 | Harris et al. |
| 2020/0015817 A1 | 1/2020 | Harris et al. |
| 2020/0205825 A1 | 7/2020 | Vendely et al. |
| 2020/0237369 A1 | 7/2020 | Jenkins et al. |
| 2020/0237370 A1 | 7/2020 | Fanelli et al. |
| 2021/0177401 A1 | 6/2021 | Abramek et al. |
| 2021/0307744 A1 | 10/2021 | Walcott et al. |
| 2024/0382198 A1* | 11/2024 | Hirschfeld ....... A61B 17/07207 |

FOREIGN PATENT DOCUMENTS

| | | | |
|---|---|---|---|
| EP | 2674111 A2 | 12/2013 |
| EP | 2777523 A1 | 9/2014 |
| WO | 2004096057 A2 | 11/2004 |
| WO | 2013151888 A1 | 10/2013 |
| WO | 2016094236 A1 | 6/2016 |

OTHER PUBLICATIONS

European Search Report and Written Opinion dated Apr. 21, 2020 for Application No. EP 20154720.5, 10 pgs.
European Search Report and Written Opinion dated May 8, 2020 for Application No. EP 20154723.9, 10 pgs.
Extended European Search Report from European Patent Application No. 23177399, dated Jan. 18, 2024, 8 pages.
International Search Report and Written Opinion dated Apr. 8, 2020 for International Application No. PCT/IB2020/050700, 12 pages.
International Search Report and Written Opinion dated Apr. 21, 2020 for International Application No. PCT/IB2020/050703, 11 pages.
International Search Report and Written Opinion dated May 4, 2020 for International Application No. PCT/IB2020/050701, 11 pages.

* cited by examiner

SURGICAL STAPLER WITH DISCRETELY POSITIONABLE DISTAL TIP

BACKGROUND

In some settings, endoscopic surgical instruments may be preferred over traditional open surgical devices to minimize the size of the surgical incision as well as post-operative recovery time and complications. Consequently, some endoscopic surgical instruments may be suitable for placement of a distal end effector at a desired surgical site through the cannula of a trocar. These distal end effectors may engage tissue in a number of ways to achieve a diagnostic or therapeutic effect (e.g., endocutter, grasper, cutter, stapler, clip applier, access device, drug/gene therapy delivery device, and energy delivery device using ultrasound, RF, laser, etc.). Endoscopic surgical instruments may include a shaft that extends proximally from the end effector to a handle portion, which is manipulated by the clinician, or alternatively to a robot. Such a shaft may enable insertion to a desired depth and rotation about the longitudinal axis of the shaft, thereby facilitating positioning of the end effector within the patient. Positioning of an end effector may be further facilitated through inclusion of one or more articulation joints or features, enabling the end effector to be selectively articulated or otherwise deflected relative to the longitudinal axis of the shaft.

Examples of endoscopic surgical instruments include surgical staplers. Some such staplers are operable to clamp down on layers of tissue, cut through the clamped layers of tissue, and drive staples through the layers of tissue to substantially seal the severed layers of tissue together near the severed ends of the tissue layers. Such endoscopic surgical staplers may also be used in open procedures and/or other non-endoscopic procedures. By way of example only, a surgical stapler may be inserted through a thoracotomy and thereby between a patient's ribs to reach one or more organs in a thoracic surgical procedure that does not use a trocar as a conduit for the stapler. Such procedures may include the use of the stapler to sever and close a vessel leading to an organ, such as a lung. For instance, the vessels leading to an organ may be severed and closed by a stapler before removal of the organ from the thoracic cavity. Of course, surgical staplers may be used in various other settings and procedures.

In some procedures, it may be necessary to fire (i.e., cut and/or staple) along tissue where more than one firing is necessary to complete the procedure. In other words, it may be necessary to perform multiple sequential firings along a continuous path, known as "marching." With procedures that involve marching, a surgical stapler end effector may be placed at the surgical site, actuated to cut and staple, removed from the surgical site for installation of a new staple cartridge, and then placed back at the surgical site again for the next firing along the same path. In some such procedures, the clinician may have a need or desire to adjust the position of a distal tip of the end effector during the surgical procedure to better facilitate the manipulation of and firing on tissue. However, known surgical staplers have limited capabilities for such adjustment.

The surgical stapling features of the present disclosure seek to enable a clinician to quickly and precisely adjust the position of a distal tip of a surgical stapler end effector during a surgical procedure. While various kinds of surgical staplers and associated components have been made and used, it is believed that no one prior to the inventor(s) has made or used the invention described in the appended claims.

BRIEF DESCRIPTION OF THE DRAWINGS

The accompanying drawings, which are incorporated in and constitute a part of this specification, illustrate embodiments of the invention, and, together with the general description of the invention given above, and the detailed description of the embodiments given below, serve to explain the principles of the present invention.

Figure 1:
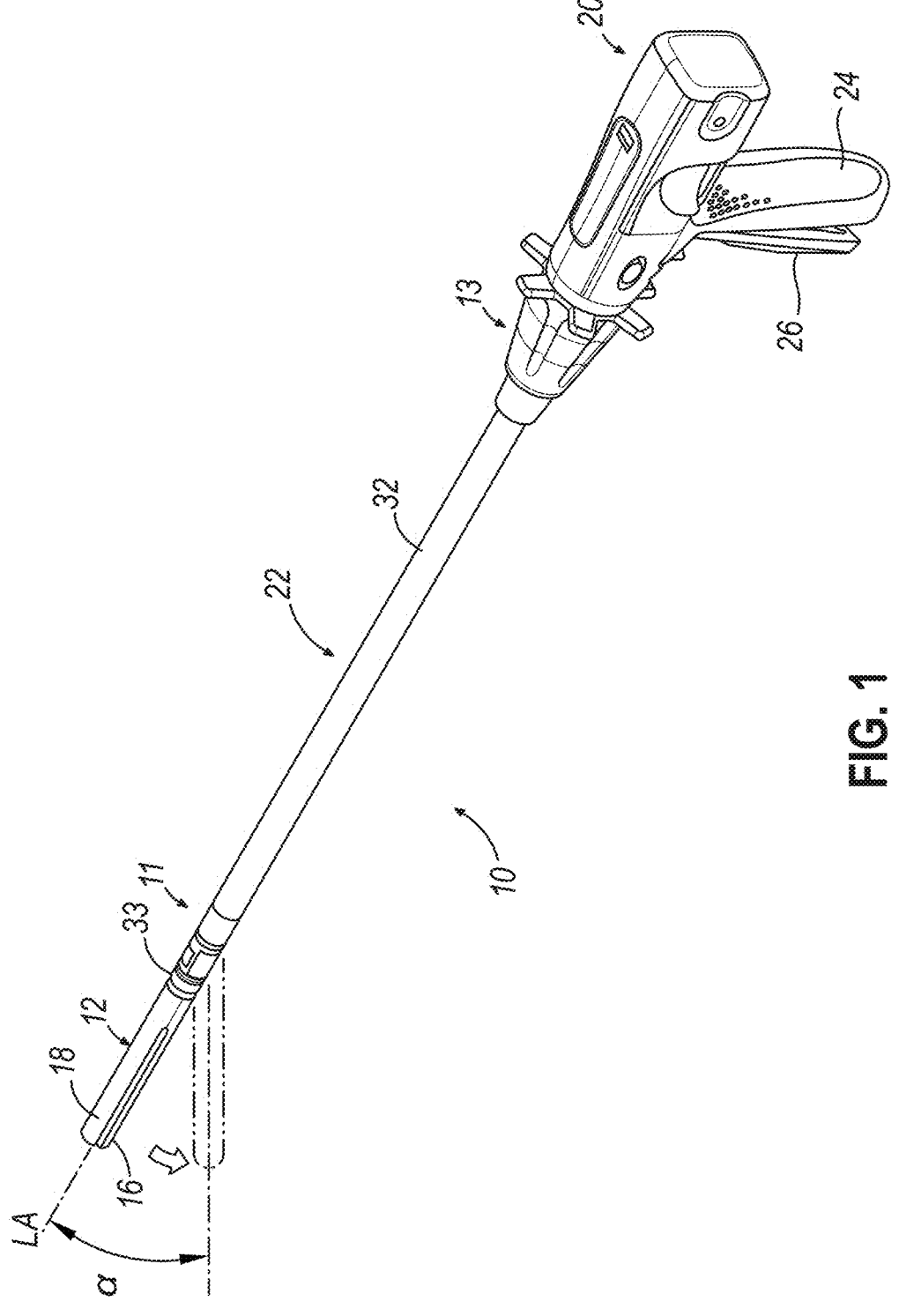
FIG. 1 depicts a perspective view of an example of an articulating surgical stapling instrument.

The drawings are not intended to be limiting in any way, and it is contemplated that various embodiments of the invention may be carried out in a variety of other ways, including those not necessarily depicted in the drawings. The accompanying drawings incorporated in and forming a part of the specification illustrate several aspects of the present invention, and together with the description serve to explain the principles of the invention; it being understood, however, that this invention is not limited to the precise arrangements shown.

DETAILED DESCRIPTION

The following description of certain examples of the technology should not be used to limit its scope. Other examples, features, aspects, embodiments, and advantages of the technology will become apparent to those skilled in the art from the following description, which is by way of illustration, one of the best modes contemplated for carrying out the technology. As will be realized, the technology described herein is capable of other different and obvious aspects, all without departing from the technology. Accordingly, the drawings and descriptions should be regarded as illustrative in nature and not restrictive.

For clarity of disclosure, the terms "proximal" and "distal" are defined herein relative to a human or robotic operator of the surgical instrument. The term "proximal" refers the position of an element closer to the human or robotic operator of the surgical instrument and further away from the surgical end effector of the surgical instrument. The term "distal" refers to the position of an element closer to the surgical end effector of the surgical instrument and further away from the human or robotic operator of the surgical instrument. In addition, the terms "upper," "lower," "lateral," "transverse," "bottom," "top," are relative terms to provide additional clarity to the figure descriptions provided below. The terms "upper," "lower," "lateral," "transverse,"

"bottom," "top," are thus not intended to unnecessarily limit the invention described herein.

Furthermore, the terms "about," "approximately," "substantially," and the like as used herein in connection with any numerical values, ranges of values, and/or geometric/positional quantifications are intended to encompass the exact value(s) or quantification(s) referenced as well as a suitable tolerance that enables the referenced feature or combination of features to function for the intended purpose described herein. For example, "substantially parallel" encompasses nominally parallel structures.

As used herein in connection with various examples of end effector jaw tips, a tip described as "angled," "bent," or "curved" encompasses tip configurations in which a longitudinal path (e.g., linear or arcuate) along which the tip extends is non-coaxial and non-parallel with a longitudinal axis of the jaw body; particularly, configurations in which the longitudinal tip path extends distally toward the opposing jaw. Conversely, a tip described as "straight" encompasses tip configurations in which a longitudinal axis of the tip is substantially parallel or coaxial with the longitudinal axis of the jaw body.

I. Illustrative Surgical Stapler

FIGS. 1-7 depict an example of a surgical stapling and severing instrument (10) that is sized for insertion through a trocar cannula or an incision (e.g., thoracotomy, etc.) to a surgical site in a patient for performing a surgical procedure. Instrument (10) of the present example includes a handle portion (20) connected to a shaft (22), which distally terminates in an articulation joint (11), which is further coupled with an end effector (12). Once articulation joint (11) and end effector (12) are inserted through the cannula passageway of a trocar, articulation joint (11) may be remotely articulated, as depicted in phantom in FIG. 1, by an articulation control (13), such that end effector (12) may be deflected from the longitudinal axis (LA) of shaft (22) at a desired angle ($\alpha$). End effector (12) of the present example includes a lower jaw (16) (also referred to herein as a cartridge jaw) that includes a staple cartridge (37), and an upper jaw in the form of a pivotable anvil jaw (18).

Unless otherwise described, the term "pivot" (and variations thereof) as used herein encompasses but is not necessarily limited to pivotal movement about a fixed axis. For instance, in some versions, anvil jaw (18) may pivot about an axis that is defined by a pin (or similar feature) that slidably translates along an elongate slot or channel as anvil jaw (18) moves toward lower jaw (16). Such translation may occur before, during, or after the pivotal motion. It should therefore be understood that such combinations of pivotal and translational movement are encompassed by the term "pivot" and variations thereof as used herein.

Handle portion (20) includes a pistol grip (24) and a closure trigger (26). Closure trigger (26) is pivotable toward pistol grip (24) to cause clamping, or closing, of anvil jaw (18) toward lower jaw (16) of end effector (12). Such closing of anvil jaw (18) is provided through a closure tube (32) and a closure ring (33), which both longitudinally translate relative to handle portion (20) in response to pivoting of closure trigger (26) relative to pistol grip (24). Closure tube (32) extends along the length of shaft (22); and closure ring (33) is positioned distal to articulation joint (11). Articulation joint (11) is operable to communicate/transmit longitudinal movement from closure tube (32) to closure ring (33).

Figure 2:
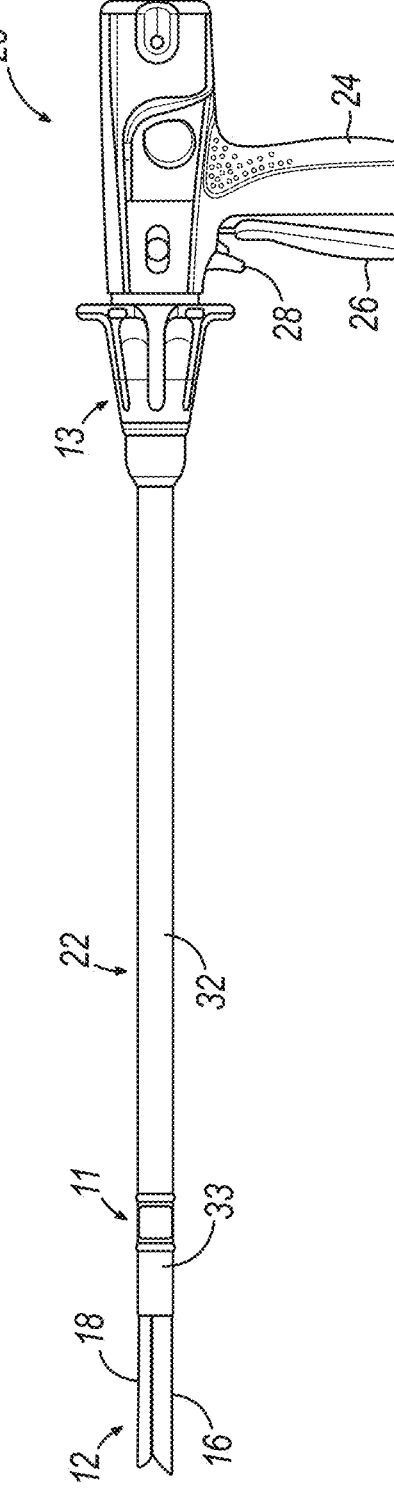
FIG. 2 depicts a side view of the instrument of FIG. 1.

As shown in FIG. 2, handle portion (20) also includes a firing trigger (28). An elongate member (not shown) longitudinally extends through shaft (22) and communicates a longitudinal firing motion from handle portion (20) to a firing beam (14) in response to actuation of firing trigger (28). This distal translation of firing beam (14) causes the stapling and severing of clamped tissue in end effector (12), as will be described in greater detail below.

As shown in FIGS. 3-6, end effector (12) employs a firing beam (14) that includes a transversely oriented upper pin (38), a firing beam cap (44), a transversely oriented middle pin (46), and a distally presented cutting edge (48). Upper pin (38) is positioned and translatable within a longitudinal anvil slot (42) of anvil jaw (18). Firing beam cap (44) slidably engages a lower surface of lower jaw (16) by having firing beam (14) extend through lower jaw slot (45) (shown in FIG. 4B) that is formed through lower jaw (16). Middle pin (46) slidingly engages a top surface of lower jaw (16), cooperating with firing beam cap (44).

Figure 3:
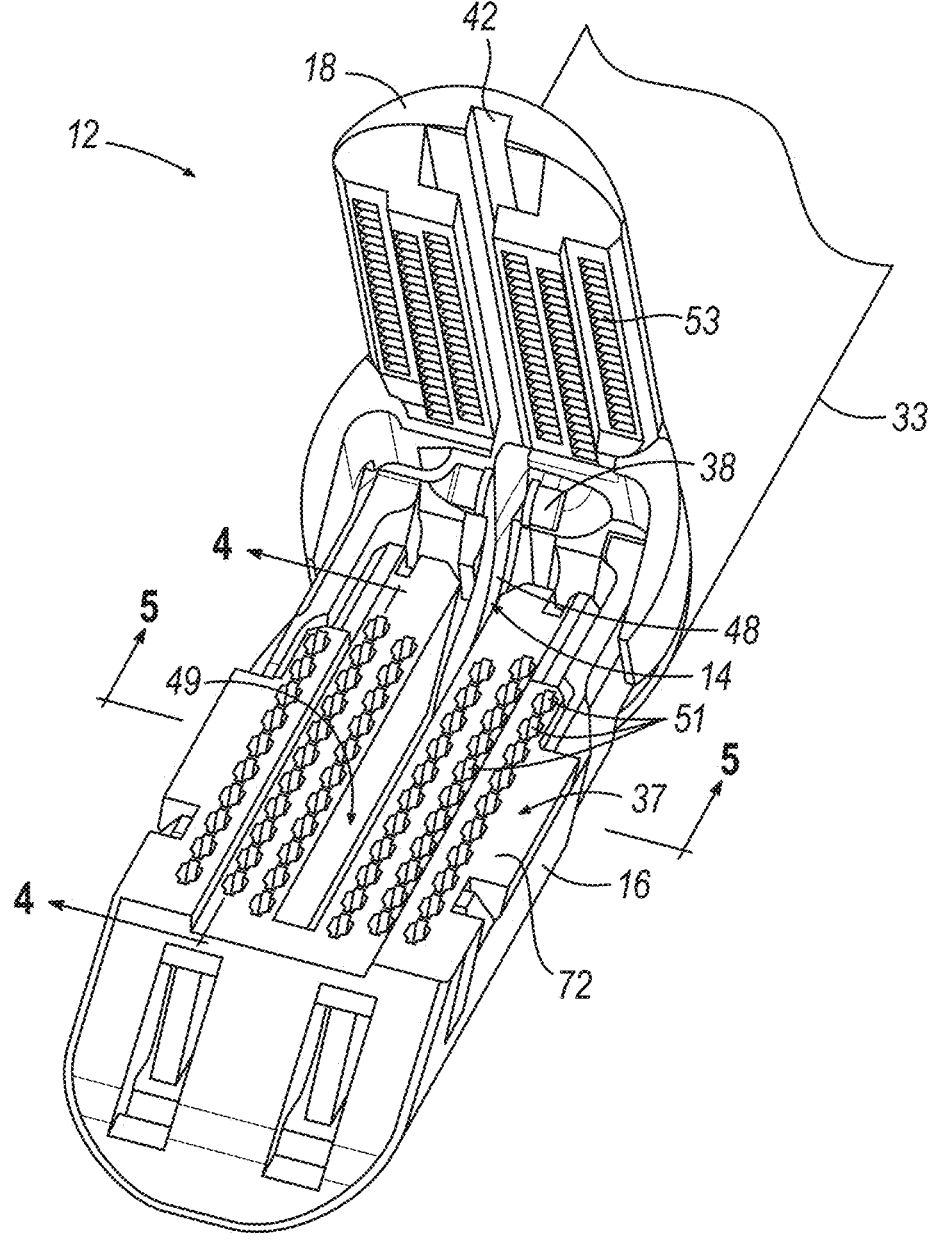
FIG. 3 depicts a perspective view of an opened end effector of the instrument of FIG. 1.
Figure 4A:
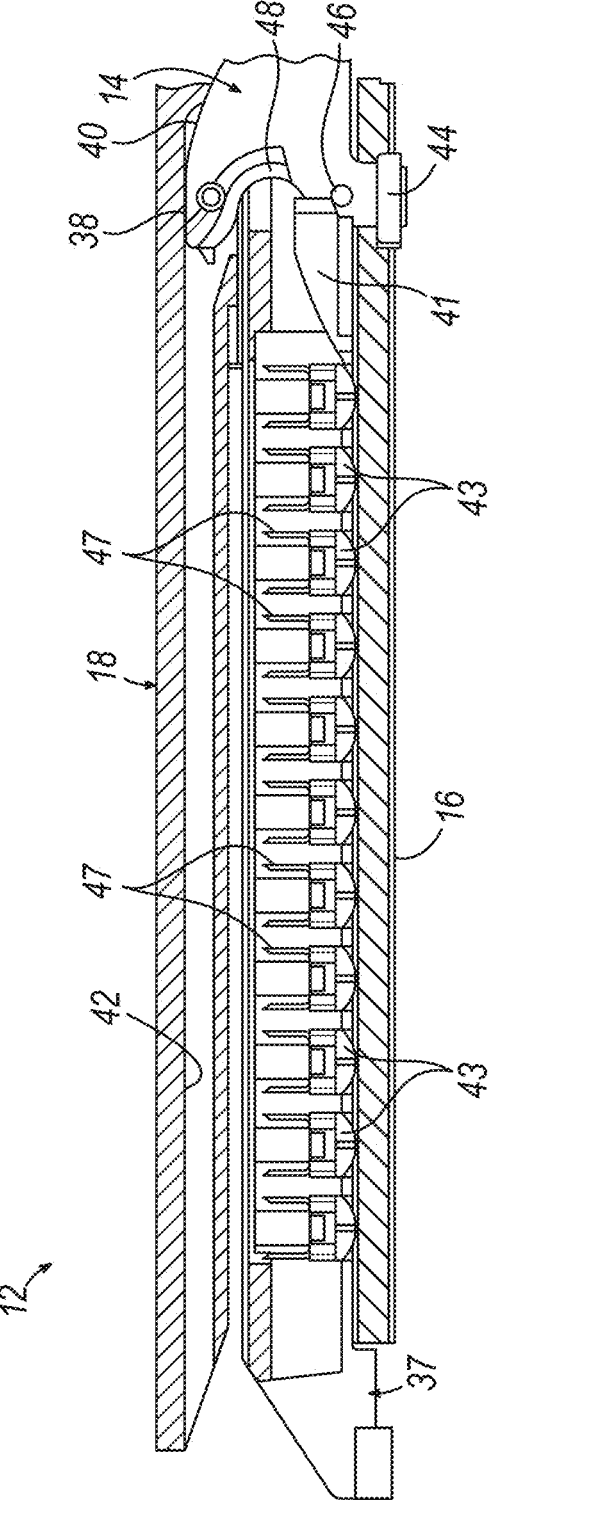
FIG. 4A depicts a side cross-sectional view of the end effector of FIG. 3, taken along line 4-4 of FIG. 3, with the firing beam in a proximal position.
Figure 4B:
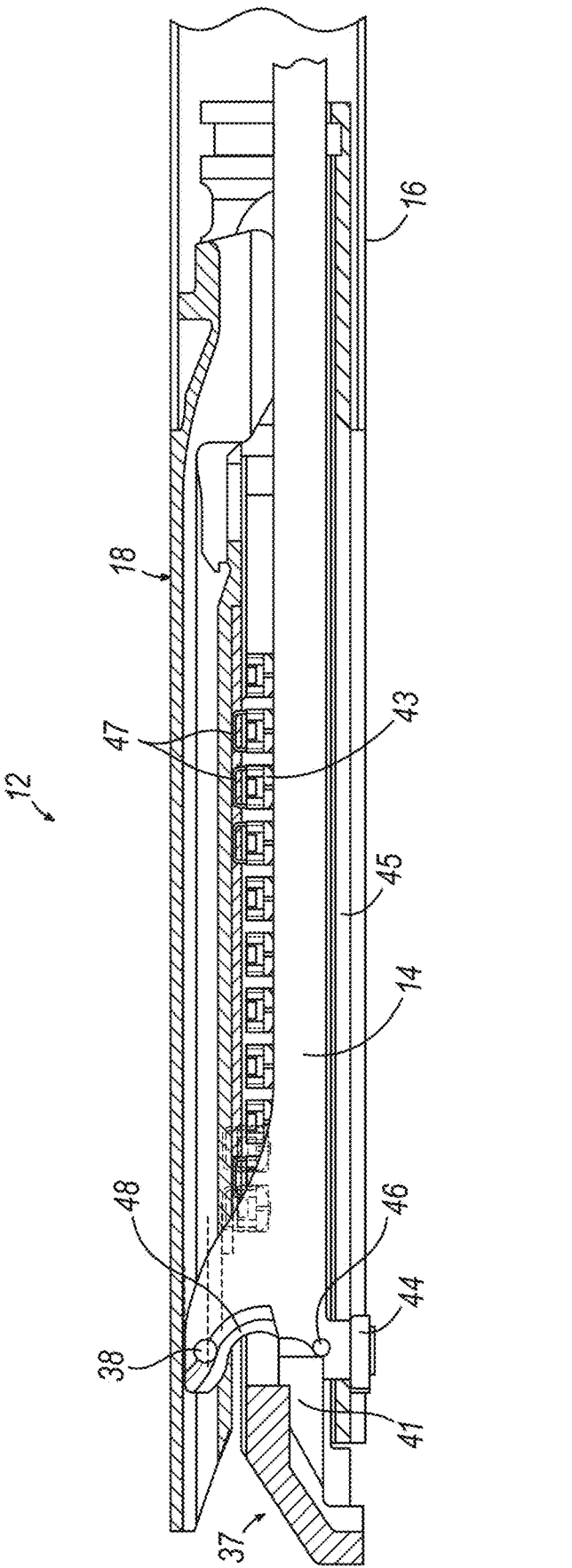
FIG. 4B depicts a side cross-sectional view of the end effector of FIG. 3, taken along line 4-4 of FIG. 3, with the firing beam in a distal position.
Figure 5:
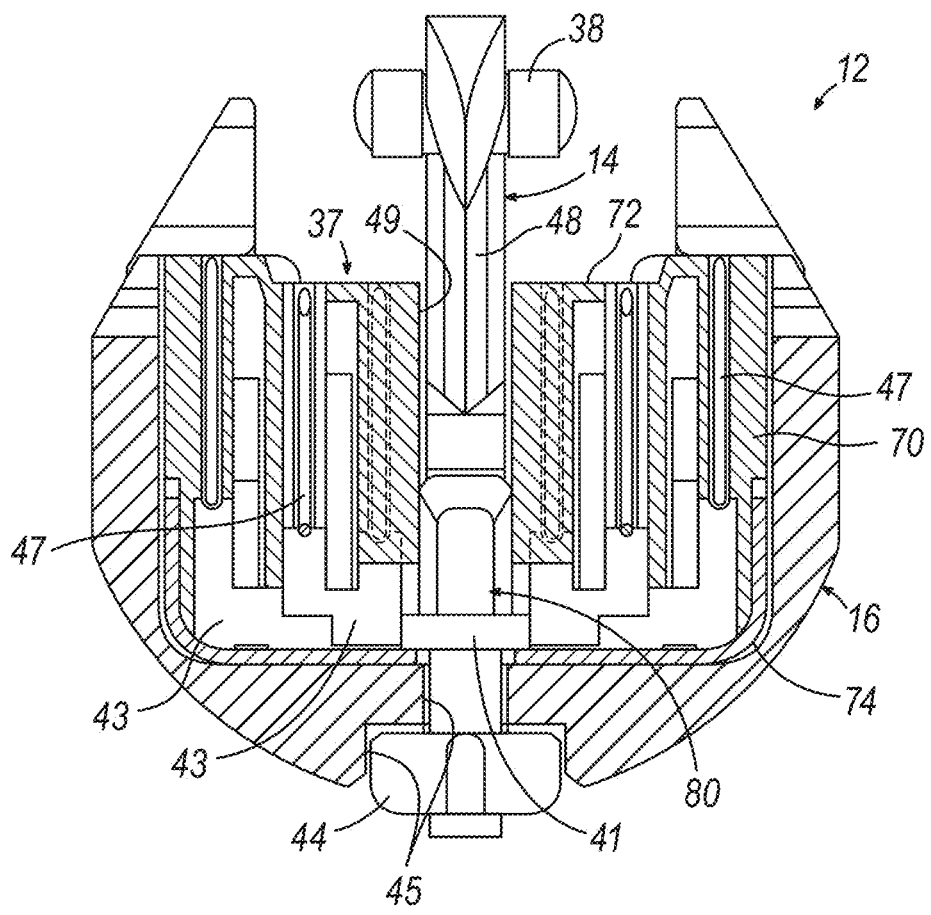
FIG. 5 depicts an end cross-sectional view of the end effector of FIG. 3, taken along line 5-5 of FIG. 3.
Figure 6:
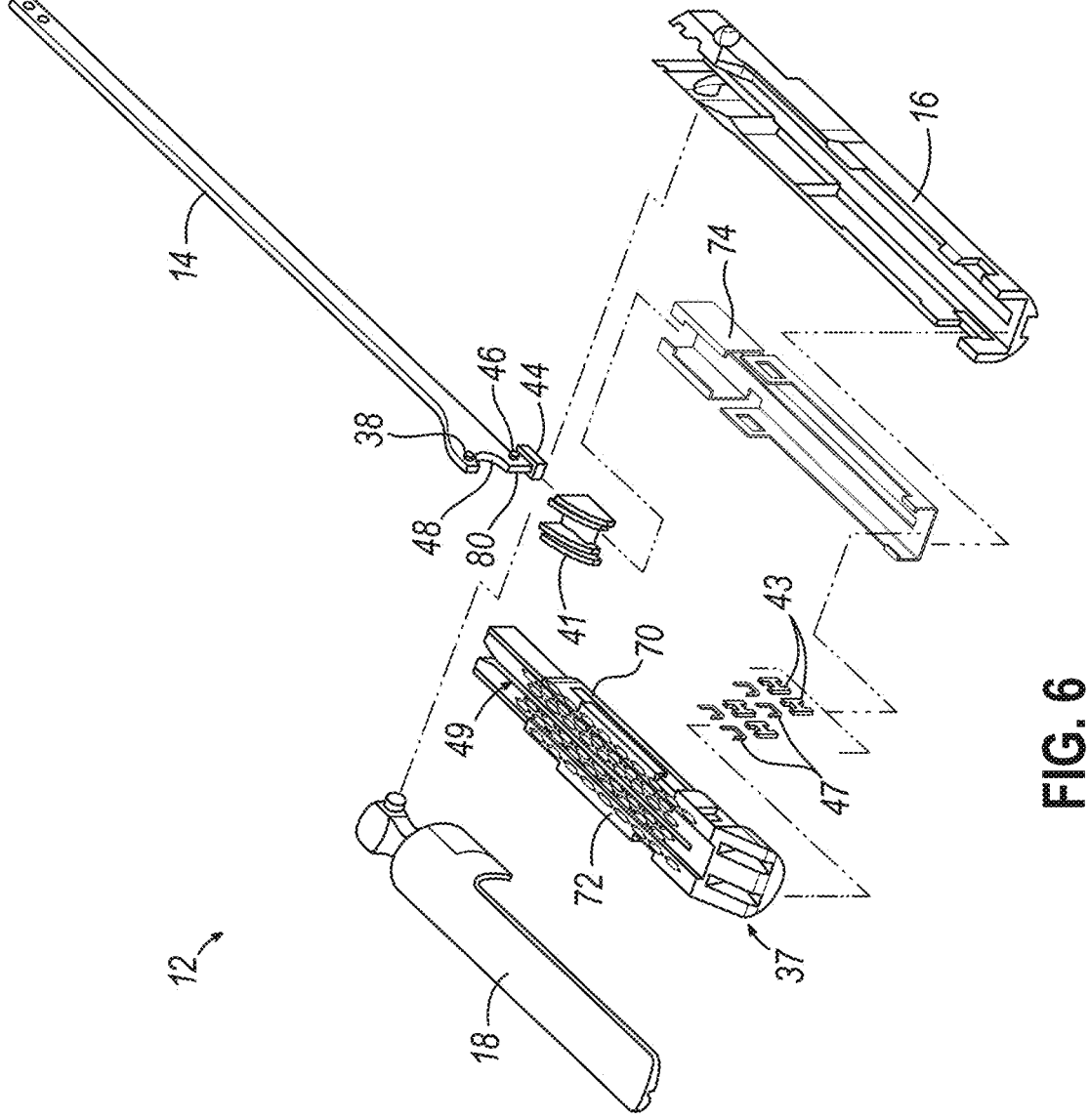
FIG. 6 depicts an exploded perspective view of the end effector of FIG. 3.

FIG. 3 shows firing beam (14) of the present example proximally positioned and anvil jaw (18) pivoted to an open configuration, allowing an unspent staple cartridge (37) to be removably installed into a channel of lower jaw (16). As best seen in FIGS. 5-6, staple cartridge (37) of the present example includes a cartridge body (70), which presents an upper deck (72) and is coupled with a lower cartridge tray (74). As best seen in FIG. 3, a vertical slot (49) extends longitudinally through a portion of staple cartridge body (70). As also best seen in FIG. 3, three rows of staple apertures (51) are formed through upper deck (72) on each lateral side of vertical slot (49). As shown in FIGS. 4A-6, a wedge sled (41) and a plurality of staple drivers (43) are captured between cartridge body (70) and tray (74), with wedge sled (41) being located proximal to staple drivers (43). Wedge sled (41) is movable longitudinally within staple cartridge (37); while staple drivers (43) are movable vertically within staple cartridge (37). Staples (47) are also positioned within cartridge body (70), above corresponding staple drivers (43). Each staple (47) is driven vertically within cartridge body (70) by a staple driver (43) to drive staple (47) out through an associated staple aperture (51). As best seen in FIGS. 4A-4B and 6, wedge sled (41) presents inclined cam surfaces that urge staple drivers (43) upwardly as wedge sled (41) is driven distally through staple cartridge (37).

With end effector (12) closed, as depicted in FIGS. 4A-4B by distally advancing closure tube (32) and closure ring (33), a firing member in the form of firing beam (14) is then advanced distally into engagement with anvil jaw (18) by having upper pin (38) enter longitudinal anvil slot (42). A pusher block (80) (shown in FIG. 5) located at distal end of firing beam (14) pushes wedge sled (41) distally as firing beam (14) is advanced distally through staple cartridge (37) when firing trigger (28) is actuated. During such firing, cutting edge (48) of firing beam (14) enters vertical slot (49) of staple cartridge (37), severing tissue clamped between staple cartridge (37) and anvil jaw (18). As shown in FIGS. 4A-4B, middle pin (46) and pusher block (80) together actuate staple cartridge (37) by entering into vertical slot (49) within staple cartridge (37), driving wedge sled (41) into upward camming contact with staple drivers (43), which in turn drives staples (47) out through staple apertures (51) and into forming contact with staple forming pockets (53) (shown in FIG. 3) on inner surface of anvil jaw (18). FIG. 4B depicts firing beam (14) fully distally translated after completing severing and stapling of tissue. Staple forming pockets (53) are intentionally omitted from the view in FIGS. 4A-4B but are shown in FIG. 3. Anvil jaw (18) is intentionally omitted from the view in FIG. 5.

Figure 7:
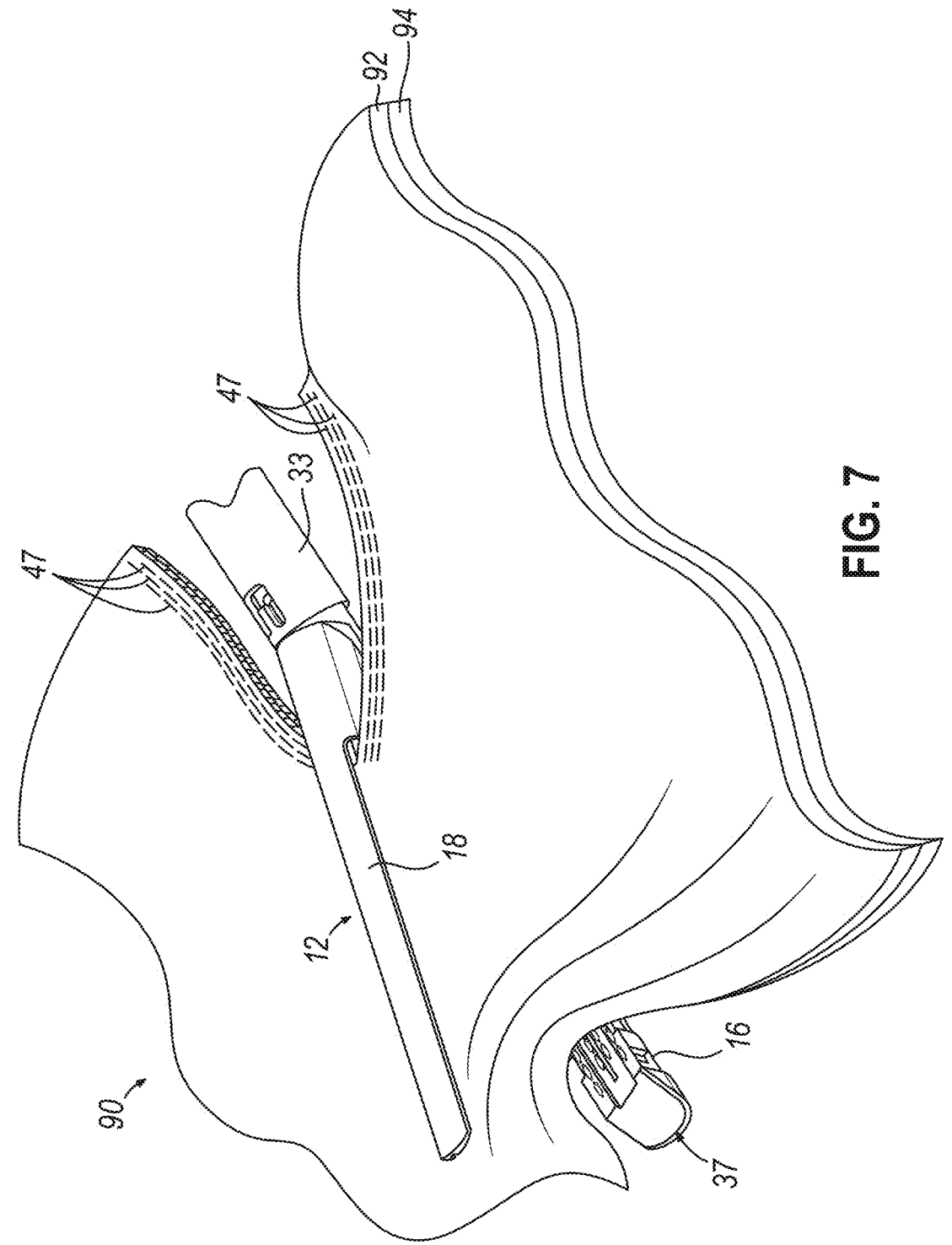
FIG. 7 depicts a perspective view of the end effector of FIG. 3, positioned at tissue and having been actuated once in the tissue.

FIG. 7 shows end effector (12) having been actuated through a single firing stroke through tissue (90). Cutting edge (48) (obscured in FIG. 7) has cut through tissue (90), while staple drivers (43) have driven three alternating rows of staples (47) through tissue (90) on each side of the cut line produced by cutting edge (48). After the first firing stroke is complete, end effector (12) is withdrawn from the patient, spent staple cartridge (37) is replaced with a new staple cartridge (37), and end effector (12) is then again inserted into the patient to reach the stapling site for further cutting and stapling. This process may be repeated until the desired quantity and pattern of firing strokes across the tissue (90) has been completed.

Instrument (10) may be further constructed and operable in accordance with any of the teachings of the following references, the disclosures of which are incorporated by reference herein: U.S. Pat. No. 8,210,411, entitled "Motor-Driven Surgical Instrument," issued Jul. 3, 2012; U.S. Pat. No. 9,186,142, entitled "Surgical Instrument End Effector Articulation Drive with Pinion and Opposing Racks," issued on Nov. 17, 2015; U.S. Pat. No. 9,517,065, entitled "Integrated Tissue Positioning and Jaw Alignment Features for Surgical Stapler," issued Dec. 13, 2016; U.S. Pat. No. 9,622,746, entitled "Distal Tip Features for End Effector of Surgical Instrument," issued Apr. 18, 2017; U.S. Pat. No. 9,717,497, entitled "Lockout Feature for Movable Cutting Member of Surgical Instrument," issued Aug. 1, 2017; U.S. Pat. No. 9,795,379, entitled "Surgical Instrument with Multi-Diameter Shaft," issued Oct. 24, 2017; U.S. Pat. No. 9,808,248, entitled "Installation Features for Surgical Instrument End Effector Cartridge," issued Nov. 7, 2017; U.S. Pat. No. 9,839,421, entitled "Jaw Closure Feature for End Effector of Surgical Instrument," issued Dec. 12, 2017; and/or U.S. Pat. No. 10,092,292, entitled "Staple Forming Features for Surgical Stapling Instrument," issued Oct. 9, 2018.

II. End Effector with Visualization, Lead-In, and Gathering Feature

In some instances, it may be desirable to provide the user with better visualization of end effector (12). In particular, as end effector (12) is inserted into a surgical site, the user may rotate shaft (22) of instrument (10) during the procedure. As a result, end effector (12) also rotates. As end effector (12) rotates, it may be desirable for the user to have visual access to the surgical site. For instance, the user may wish to see the interface or contact between tissue (90) and end effector (12). Since end effector (12) may be rotated about the longitudinal axis (LA) relative to handle portion (20), the user may view the surgical site such that lower jaw (16) of end effector is visible rather than anvil jaw (18). Alternatively, end effector (12) could be rotated such that when the user views end effector (12), anvil jaw (18) is visible by the user. It may be desirable to provide visibility of the surgical site for the user beyond what is possible in instrument (10) of FIG. 1.

For instance, in the case of some surgical procedures where fluid carrying vessels are transected and stapled, it may be desirable to have visual confirmation that anvil jaw (18) and lower jaw (16) completely cover the vessel to be cut, such that the vessel may be fully cut and stapled in one single actuation. In other words, the user may wish to avoid cutting and stapling only a portion of a vessel. Thus, some means of visual monitoring and/or feedback may be desirable so that the user will know that end effector (12) has been positioned properly within the surgical site for anvil jaw (18) and lower jaw (16) to fully clamp the vessel. One potential way of monitoring the surgical site may include improving visualization of the area adjacent to the distal tip of lower jaw (16) and anvil jaw (18). Furthermore, not only visualization of the distal end of end effector (12) may be desirable, but also it may be desirable to construct end effector (12) such that the distal end of anvil jaw (18) is configured to urge tissue (e.g., a large vessel) proximally into the space between anvil jaw (18) and lower jaw (16) as anvil jaw (18) closes toward lower jaw (16).

Figure 8:
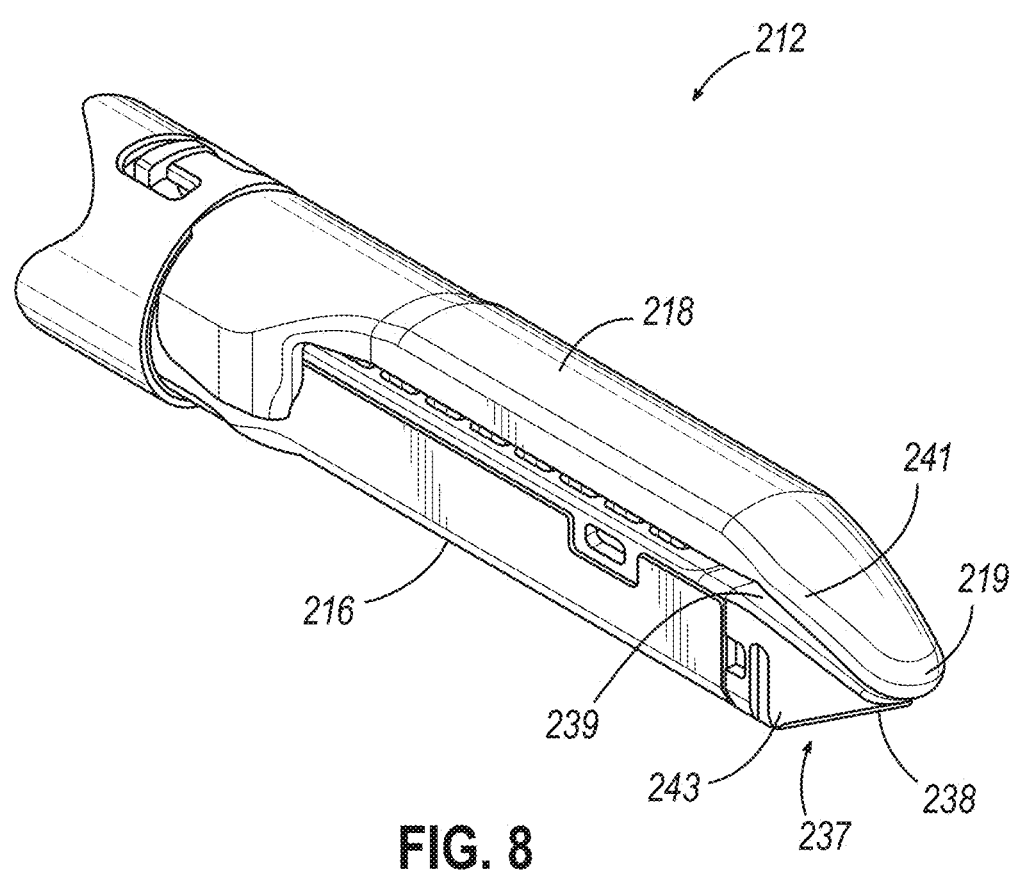
FIG. 8 depicts a perspective view of an alternative version of an end effector with an angled anvil jaw and an angled cartridge.

FIG. 8 depicts an example of an end effector (212) comprising an anvil jaw (218) and a lower jaw (216). It will be appreciated that end effector (212) may be used in place of end effector (12) of instrument (10). End effector (212) may be integrally formed with instrument (10) or in the alternative may be interchangeable with end effector (12) of instrument (10).

Anvil jaw (218) is operable to pivot relative to lower jaw (216). Anvil jaw (218) and lower jaw (216) may clamp tissue (90) similarly to clamping performed by anvil jaw (18) and lower jaw (16) shown in FIG. 1. End effector (212) further includes a cartridge (237) operable to be placed in lower jaw (216) similarly to cartridge (37) shown in FIG. 3.

Figure 9:
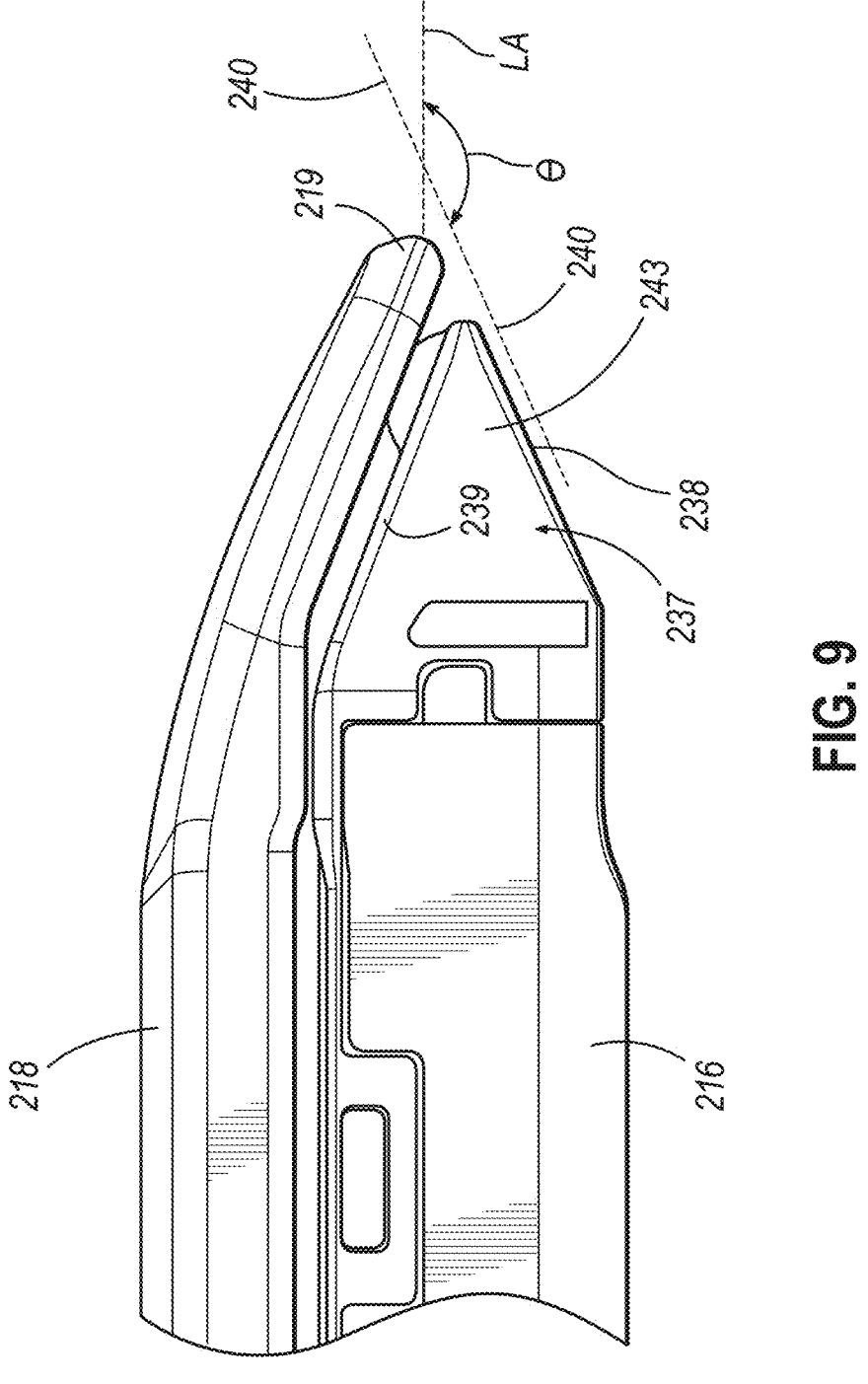
FIG. 9 depicts an enlarged, side view of the end effector of FIG. 8.
Figure 10:
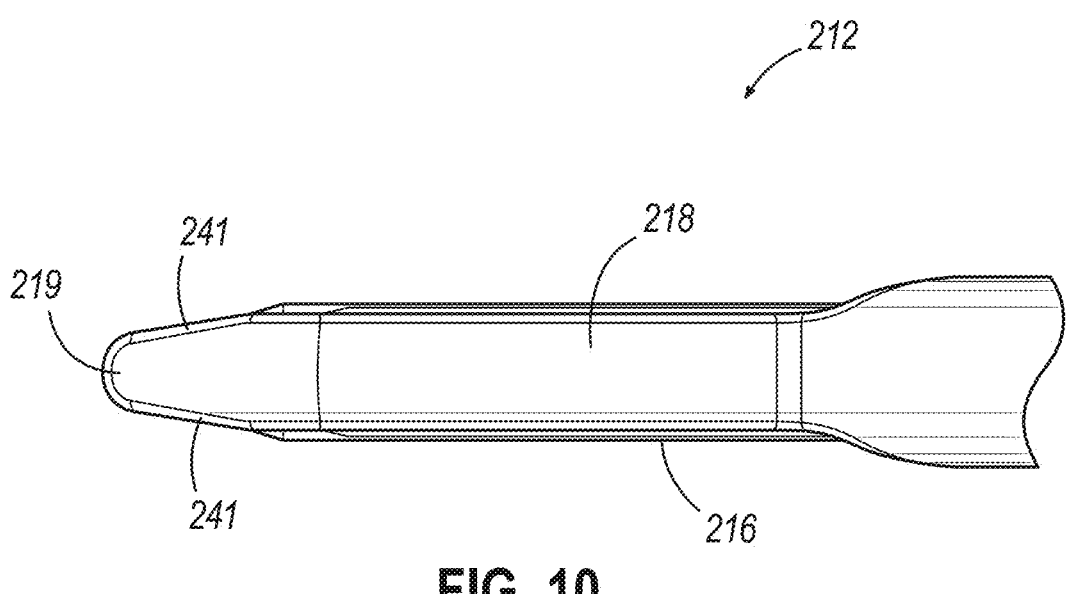
FIG. 10 depicts an enlarged top view of the end effector of FIG. 8.

Anvil jaw (218) as can be seen in FIGS. 8-10 has an elongated shape where the distal portion of anvil jaw (218) angles toward cartridge (237). The distal portion of anvil jaw (218) angles toward cartridge (237) such that the distal most distal tip (219) of anvil jaw (218) extends distally longitudinally further than cartridge (237). Though in some versions, distal tip (219) may extend to a distance longitudinally equal to cartridge (237) or proximal relative to the distal most point on cartridge (237). Furthermore, anvil jaw (218) angles toward cartridge (237) through a gentle slope. As seen best in FIG. 10, anvil jaw (218) includes sides (241) that taper as they approach the distal most distal tip (219) of anvil jaw (218). By way of example, anvil jaw (218) is shaped in FIG. 8 similarly to an inverted ski tip. The angled shape of anvil jaw (218) may provide easier insertion of end effector (212) into a surgical site. For instance, the gentle slope or inverted ski tip shape of anvil jaw (218) may provide an atraumatic tissue deflection surface as anvil jaw (218) contacts or moves through tissue. Such atraumatic tissue deflection may include urging tissue (e.g., a large vessel) proximally into the space between anvil jaw (218) and lower jaw (216) as anvil jaw (218) closes toward lower jaw (216). Once placed into a surgical site, the angled shape of anvil jaw (218) may also provide better maneuverability of end effector (212) and better visibility of the distal end of end effector (212) in relation to anatomical structures at the surgical site. Other suitable variations of anvil jaw (218) will be apparent to one of ordinary skill in the art in view of the teachings herein.

Cartridge (237) is operable to hold staples similar to staples (47) shown in FIG. 4A for driving into tissue. As shown in FIG. 9, the distal end of cartridge (237) has a triangular profile. In particular, the distal end of cartridge (237) includes an upper tapered surface (239) and a lower tapered surface (238). Additionally, the distal end of cartridge (237) includes a tapered side surface (243) on each side. In the present example, each tapered side surface (243) of cartridge (237) generally aligns with the taper presented by sides (241) of anvil jaw (218). Thus, as shown in FIG. 10, side surfaces (243) of cartridge (237) do not extend outwardly from longitudinal axis (LA) of end effector (212) past sides (241) of anvil jaw (218). Upper tapered surface (239) and lower tapered surface (238) lead to the distal most end of cartridge (237). Lower tapered surface (238) defines a sight line (240) such that once end effector (212) is inserted into a surgical site, the user can see along sight line (240). Sight line (240) extends along the edge of lower tapered surface (238). It will be appreciated that the planar shape of lower tapered surface (238) may be operable to allow the user to visualize and/or nearly visualize the distal tip (219) of anvil jaw (218). In particular, sight line (240) intersects longitudinal axis (LA), which extends longitudinally through end effector (212), to form a viewing angle (θ).

Viewing angle (θ) may establish the relative visibility that a user has regarding distal tip (219). In particular, the user can see in front of distal tip (219) along any line of sight that passes through the intersection of sight line (240) and longitudinal axis (LA) within viewing angle (θ). For instance, as viewing angle (θ) increases, the user would have greater visibility of the area immediately in front of distal tip (219) from proximal vantage points; whereas as viewing angle (θ) decreases, the user has less visibility of the area in front of distal tip (219) from proximal vantage points. In some versions, viewing angle (θ) defines an angle greater than 90 degrees. Additionally, in some versions, viewing angle (θ) defines an angle greater than 135 degrees. Other suitable angles for viewing angle (θ) will be apparent to one of ordinary skill in the art in view of the teachings herein. In the illustrated version, the user generally looks along sight line (240) or along some other line of sight within viewing angle (θ), thus, the user has visibility along sight line as well as any area within viewing angle (θ). The underside of distal tip (219) is further slightly rounded to aid in the visibility of the intersection of longitudinal axis (LA) and sight line (240).

When tissue (90) is clamped between a closed cartridge (237) and anvil jaw (218), the user can look along sight line (240) or elsewhere within viewing angle (θ) to see, for instance, precisely where anvil jaw (218) has clamped tissue (90). Furthermore, the user would be able to determine whether the tissue is completely clamped between anvil jaw (218) and cartridge (237) such that tissue does not spill over the end of end effector (212). The user may be able to also visualize the quality of the clamp between anvil jaw (218) and cartridge (237) against tissue (90). It will be appreciated that in some instances, end effector (212) may be rotated before, during, or after clamping tissue (90). As a result, the tapered shape of anvil jaw (218) may also provide more accessible viewing of distal tip (219) or substantially adjacent distal tip (219). The taper of anvil jaw (218) along with lower tapered surface (238) of cartridge (237) may further promote easy insertion of end effector (212) into tissue in an atraumatic manner. Furthermore, it may be easier to fit end effector (212) through a trocar or other devices operable to introduce end effector (212) into a surgical site due to the tapered end of end effector (212). For instance, once distal tip (219) is fit into a trocar, lower tapered surface (238) and the tapered shape of anvil jaw (218) may provide a lead-in, guiding the rest of end effector (212) into the trocar. In view of the teachings herein, those of ordinary skill in the art will further appreciate that visibility and maneuverability can be enhanced by the tapered design for both sides (241) of anvil jaw (218) and each side (243) of cartridge (237).

In addition to the foregoing, end effector (212) and versions of instrument (10) incorporating end effector (212) may be configured and operable in accordance with at least some of the teachings of U.S. Pat. No. 9,186,142, entitled "Surgical Instrument End Effector Articulation Drive with Pinion and Opposing Racks," issued Nov. 17, 2015, the disclosure of which is incorporated by reference herein; U.S. Pat. No. 9,717,497, entitled "Lockout Feature for Movable Cutting Member of Surgical Instrument," issued Aug. 1, 2017, the disclosure of which is incorporated by reference herein; U.S. Pat. No. 9,517,065, entitled "Integrated Tissue Positioning and Jaw Alignment Features for Surgical Stapler," issued Dec. 13, 2016, the disclosure of which is incorporated by reference herein; U.S. Pat. No. 9,839,421, entitled "Jaw Closure Feature for End Effector of Surgical Instrument," issued Dec. 12, 2017, the disclosure of which is incorporated by reference herein; U.S. Pat. No. 9,622,746, entitled "Distal Tip Features for End Effector of Surgical Instrument," issued Apr. 18, 2017, the disclosure of which is incorporated by reference herein; U.S. Pat. No. 10,092,292, entitled "Staple Forming Features for Surgical Stapling Instrument," Oct. 9, 2018, the disclosure of which is incorporated by reference herein; U.S. Pat. No. 9,795,379, entitled "Surgical Instrument with Multi-Diameter Shaft," issued Oct. 24, 2017, the disclosure of which is incorporated by reference herein; and/or U.S. Pat. No. 9,808,248, entitled "Installation Features for Surgical Instrument End Effector Cartridge," issued Nov. 7, 2017, the disclosure of which is incorporated by reference herein. Further modifications that may be incorporated into end effector (212) will be described in greater detail below.

III. End Effectors with Angled Elastically Deformable Distal Tips

As can be seen in FIGS. 4A-4B and FIG. 7, the distal end configuration of end effector (12) provides a gap between the distal end of anvil jaw (18) and the distal end of cartridge (37). This gap may facilitate marching by providing an atraumatic space for tissue to enter the distal end of end effector (12) at the beginning of each marching step.

As noted above, the distal end configuration of end effector (212) is different from the distal end configuration of end effector (12); with the different configuration of end effector (212) providing different potential advantages. In particular, the distal end configuration of end effector (212) may provide improved maneuverability and improved visibility of the relationship between the distal end of end effector (212) and adjacent anatomical structures. In addition, the distal end configuration of end effector (212) may provide tissue-gathering effects by urging tissue proximally into the space between anvil jaw (218) and lower jaw (216) as anvil jaw (218) is closed toward lower jaw (216). However, in versions where all the structures of end effector (212) are rigid, the bent configuration of distal tip (219) of anvil jaw (218) may not lend itself well to marching operations, as distal tip (219) may impart trauma to tissue that is not gathered into the space between anvil jaw (218) and lower jaw (216) as anvil jaw (218) is closed toward lower jaw (216). Thus, in versions where all the structures of end effector (212) are rigid, end effector (212) may be best suited for cutting and stapling operations (e.g., vessel transection) where all of the tissue that is to be cut and stapled is gathered proximal to distal tip (219).

In view of the foregoing, it may be desirable to provide a variation of end effectors (12, 212) that provides the marching capabilities of end effector (12), the improved visibility associated with end effector (212), and the tissue gathering capabilities of end effector (212), without providing an increased risk of trauma that might otherwise be associated with fully rigid versions of end effector (212). The following describes several merely illustrative examples of such variations of end effectors (12, 212). In the following examples, an anvil jaw has a distal tip that is resiliently biased to assume a bent or angled configuration like distal tip (219); yet the resiliently biased distal tip is deflectable away from the lower jaw in response to a sufficient load on the distal tip. It will be understood in view of the teachings herein that providing an anvil jaw with an elastically deformable angled distal tip portion can provide an additional level of maneuverability benefits in terms of navigating through tissue to a surgical site. In this manner, the deformable distal tip portion may deflect or deform to promote smooth and atraumatic movement of the end effector through tissue, particularly during marching operations. Additionally, with an anvil jaw having a bias to an angled position when not in a loaded state or contacted by surrounding tissue, enhanced visualization during tissue capture and cutting can be achieved compared to using end effectors with a straight or non-angled anvil jaw. Moreover, an anvil jaw with a distal tip that is biased to an angled position may provide some degree of tissue gathering effects up until reaching a load point that would be associated with marching rather than being associated with simply gathering a relatively small tissue structure between the anvil jaw and lower jaw.

Figure 11:
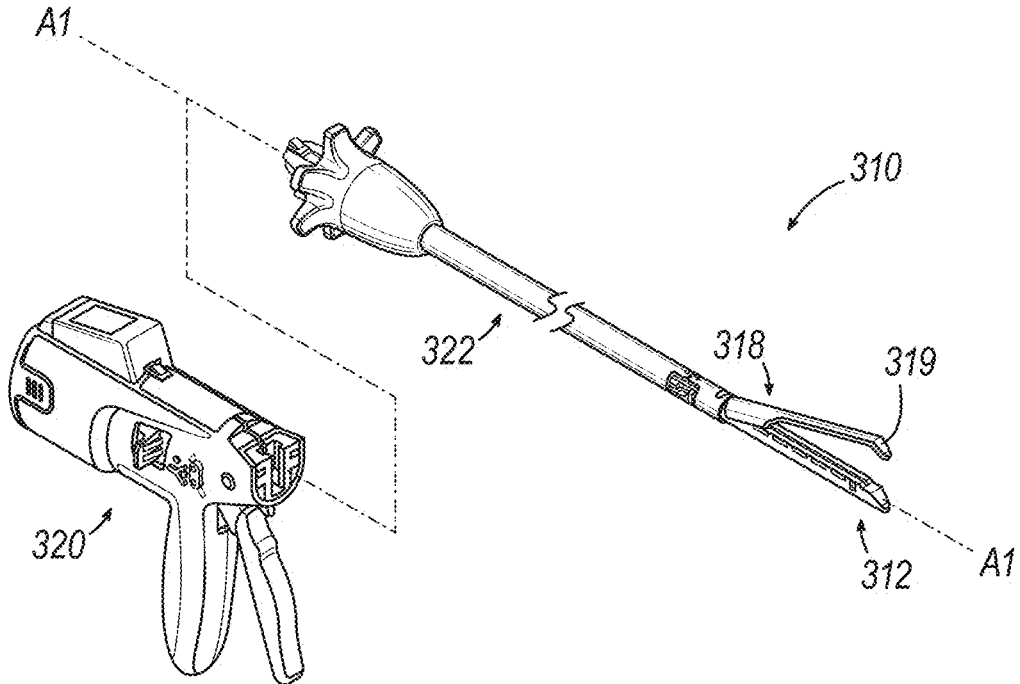
FIG. 11 depicts a perspective view of an example of a surgical stapling instrument having an end effector with a curved elastically deformable tip section.

FIG. 11 shows another example of an instrument (310) configured as a surgical stapler. Instrument (310) includes a handle portion (320) and a shaft (322). Instrument (310) has a modular configuration such that shaft (322) is selectively removable from, and attachable to, handle portion (320). Instrument (310) is configured similarly to instrument (10) such that the operability and use of instrument (310) is the same as described above for instrument (10) with the added feature of instrument (310) being a modular configuration. With its modular configuration, instrument (310) provides a way to change the end effector. Such a change in the end effector may be made to replace an otherwise worn end effector, or to provide for a different end effector configuration based on the procedure or user preference. In addition to or in lieu of the foregoing, features operable for providing the modular configuration of instrument (310) may be configured in accordance with at least some of the teachings of U.S. Pat. No. 10,182,813, entitled "Surgical Stapling Instrument with Shaft Release, Powered Firing, and Powered Articulation," issued Jan. 22, 2019, the disclosure of which is incorporated by reference herein. Other suitable components, features, and configurations for providing instrument (310) with a modular configuration will be apparent to those of ordinary skill in the art in view of the teachings herein. Moreover, it will be understood by those of ordinary skill in the art in view of the teachings herein, that instrument (10) may be modified to incorporate a modular configuration as shown and described with respect to instrument (310) or other instruments incorporated by reference herein.

In the illustrated example of FIG. 11, instrument (310) includes an end effector (312) having an anvil jaw (318) that has an angled distal tip (319). Furthermore, distal tip (319) of anvil jaw (318) is elastically deformable. In this manner, and as shown best in FIGS. 12A and 12B, angled distal tip (319) is operable to elastically deform from a first angled position to a second position. The second position for angled distal tip (319) may be substantially straight in some versions, but may be angled to a degree (e.g., slightly above or slightly below the longitudinal axis (A1)) in other versions. It should be understood that the second position for angled distal tip (319) may be defined by the characteristics (e.g., thickness, density, etc.) of the tissue that is being captured between anvil jaw (318) and lower jaw (16). In the present example, end effector (312) is provided on shaft (322) that is detachable from handle portion (320). By way of example only, shaft (322) may be detachable from handle portion (320) in accordance with at least some of the teachings of U.S. Pat. No. 9,913,642, entitled "Surgical Instrument Comprising a Sensor System," issued Mar. 13, 2018, the disclosure of which is incorporated by reference herein. In some other versions, shaft (322) is not detachable from handle portion (320).

It will be appreciated that end effector (312) may be used in place of end effector (12) shown in FIG. 1. In some versions, end effector (312) may be integrally formed with shaft (22) or alternatively may be separately formed and then combined. In some versions, end effector (312) may be provided for use in robotic systems. In such robotic systems, modular shaft (322) having end effector (312) may be attachable to a portion of the robotic system for use such that handle portion (320) is replaced by components of the robotic system. Still in other examples, end effector (312) may be adapted for use with a robotic system in a manner where end effector (312) connects with the robotic system without necessarily connecting the entire modular shaft (322). In view of the teachings herein, other ways to incorporate an end effector having an angled elastically deformable anvil tip into a user operated or robotic operated instrument will be apparent to those of ordinary skill in the art.

Figure 12A:
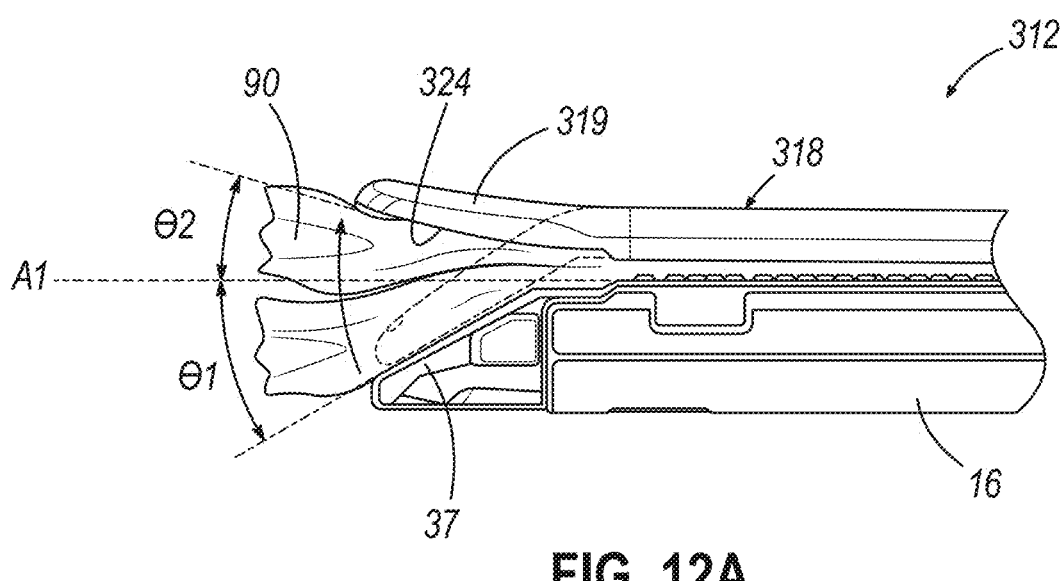
FIG. 12A depicts an enlarged side view of a distal portion of the end effector of FIG. 11.

FIG. 12A shows an enlarged side view of the distal end of end effector (312). End effector (312) includes anvil jaw (318) and lower jaw (16) that accepts cartridge (37) as described above with respect to instrument (10). Anvil jaw (318) pivotably rotates toward lower jaw (16) in the same manner as anvil jaw (18) as described above with respect to instrument (10). In this configuration, end effector (312) is similar to end effector (12), however, anvil jaw (318) includes angled distal tip (319) that is elastically deformable. As shown in FIG. 12A, distal tip (319) is imparted with a bias to an angled position that is shown in FIG. 11 and in phantom in FIG. 12A. Distal tip (319) assumes this angled position when end effector (312) is not clamping tissue and is open, as shown in FIG. 11; or closed without clamping tissue, as shown in phantom in FIG. 12A. In instances when end effector (312) is in this angled state or position, end effector (312) can be considered not loaded or in a non-loaded state or position. Conversely when end effector (312) is clamping tissue, end effector (312) can be considered loaded or in a loaded state or position.

When closed and not clamping tissue between anvil jaw (318) and lower jaw (16), distal tip (319) contacts cartridge (37). In this position, an underside surface (324) of distal tip (319) defines a plane that intersects a longitudinal axis (A1) defined by shaft (322) to form an angle (01). When closed and clamping tissue (90) between anvil jaw (318) and lower jaw (16), underside surface (324) of distal tip (319) contacts tissue (90). In this position, underside surface (324) of distal tip (319) defines a plane that intersects longitudinal axis (A1) to form an angle (02). In the illustrated example of FIG. 12A, angles (01, 02) are relative to longitudinal axis (A1), and the sum of angles (01, 02) represent the range of motion distal tip (319) undergoes. By way of example only, and not limitation, in some examples angle (01) is between about 20 and about 70 degrees, or more particularly between about 30 degrees and about 50 degrees, in a downward direction from longitudinal axis (A1) toward cartridge (37). By way of example only, and not limitation, in some examples angle (02) is between about 0 and about 90 degrees in an upward direction from longitudinal axis (A1) away from cartridge (37). By way of example only, and not limitation, in some examples the range of motion undergone by distal tip (319) is between about 20 degrees and about 110 degrees. The angles described for angles (01, 02) are examples only and not limiting. Other suitable angles will be apparent to those of ordinary skill in the art in view of the teachings herein.

Additionally, in some instances longitudinal axis (A1) represents a zero-degree reference and angles relative thereto may be positive or negative. For instance, where an angle is in a downward direction from longitudinal axis (A1) toward cartridge (37), the angle may be characterized as a negative angle. Similarly, where an angle is in an upward direction from longitudinal axis (A1) away from cartridge (37), the angle may be characterized as a positive angle. When using these conventions, the range of motion of distal tip (319) due to deformation can be understood as the sum of the absolute value of the angle when distal tip (319) is in the position contacting cartridge (37), and the angle when distal tip (319) is in the deformed state when clamping tissue.

Figure 12B:
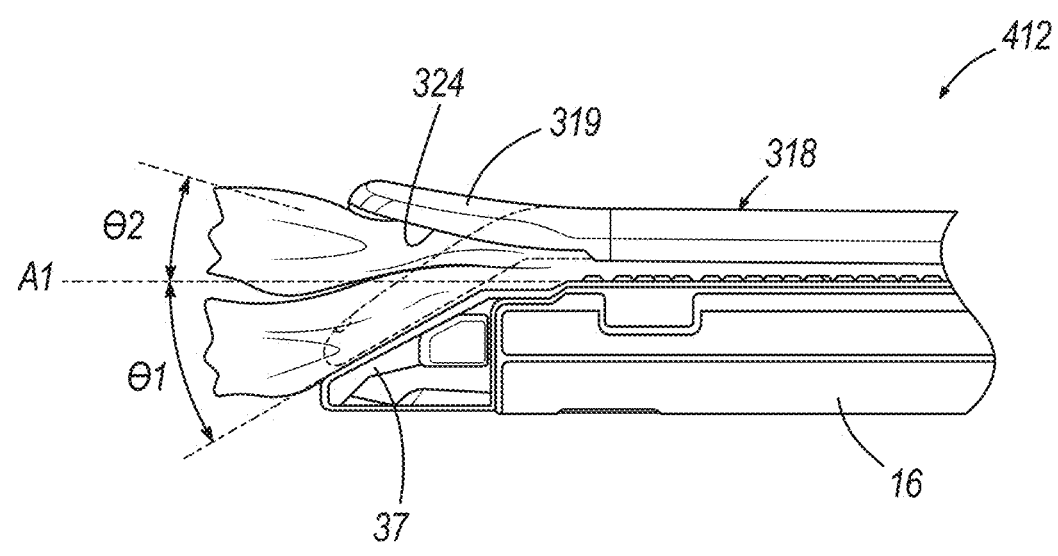
FIG. 12B depicts an enlarged side view of a distal portion of an alternate end effector similar to that of FIG. 11.

FIG. 12B shows another side view of an alternate end effector (412) similar to end effector (312) of FIG. 12A. With end effector (312), when anvil jaw (318) is in its angled and non-deformed state (as seen in phantom in the view of FIG. 12A), anvil jaw (318) extends to a point even with or proximal to the distal most end of cartridge (37). When anvil jaw (318) is deformed such that it is deflected upwardly, the end of distal tip (319) extends to a point just distal to the distal most end of cartridge (37). With end effector (412), as shown in FIG. 12B, when anvil jaw (318) is in its angled and non-deformed state (as seen in phantom in the view of FIG. 12B), anvil jaw (318) extends to a point even with or proximal to the distal most end of cartridge (37). When anvil jaw (318) is deformed such that it is deflected upwardly, the end of a distal tip (319) of anvil jaw (318) extends to a point even with or proximal to the distal most end of cartridge (37). In this manner, anvil jaw (318) of end effector (412) remains even with or proximal to the distal most end of cartridge (37) when anvil jaw (318) is in its angled state or deformed state such that anvil jaw (318) does not extend past the distal most end of cartridge (37) whether anvil jaw (318) is in its angled and non-deformed state or in its deformed state. In some instances, this can be achieved by modifying anvil jaw (318) such that distal tip (319) of anvil jaw is shortened in length. In other instances, instruments (10, 310) may be modified to provide for a slight proximal retraction of anvil jaw (318) when clamping. In view of the teachings herein, other ways to modify end effector (412) as it relates to control of anvil jaw (318) position, will be apparent to those of ordinary skill in the art.

IV. End Effector Jaws with Discretely Positionable Distal Tips

In some instances, it may be desirable to provide a clinician with a versatile end effector jaw having a distal tip that can assume multiple discrete positions relative to the jaw body to accommodate various needs during a surgical procedure. In that regard, it may be desirable to a user to have an end effector with an angled (or "bent") distal tip that provides visualization and placement benefits as described above, or that more effectively urges tissue (e.g., a large vessel) proximally into the space between the anvil jaw and the cartridge jaw as the end effector closes. In other circumstances, it may be desirable to a user to use an end effector with a substantially straight distal tip to better facilitate marching as described above, or to reduce the pressure exerted on tissue positioned under the distal tip.

Each of the illustrative end effector jaws described below in connection with FIGS. 14-39B is configured for use with any of the surgical stapling instruments described herein and includes a distal tip configured to move (e.g., pivot or rotate) relative to the jaw body between at least a first discrete position and a second discrete position to adjust an orientation of the longitudinal distal tip axis relative to the longitudinal jaw body axis, and maintain that discrete position. Transition between such discrete positions occurs in response to an external input force intentionally applied to the distal tip by, for example, the clinician directly or indirectly via patient anatomy in contact with the distal tip. Additionally, each end effector jaw is suitably configured such that its distal tip will maintain its current discrete position until acted upon by an external input force intentionally applied to the distal tip by, for example, the clinician, directly or indirectly.

While such end effector jaws of the present versions are shown in the form of anvil jaws each having an anvil jaw body with a plurality of staple forming pockets, in other versions such discretely positionable distal tips may be applied to a cartridge jaw that is configured to receive a replaceable staple cartridge or otherwise support a stapling assembly that houses a plurality of staples. Additionally, while the first discrete position of each end effector jaw described below is presented in the form of a straight position in which the distal tip axis extends substantially parallel to the jaw body axis, in other versions the first discrete position may include an angled position in which the distal tip axis is angled relative to the jaw body axis, for example in a direction away from the opposing end effector jaw. Additionally, in other versions the end effector jaws may include more than two discrete positions for their distal tips.

Figure 14:
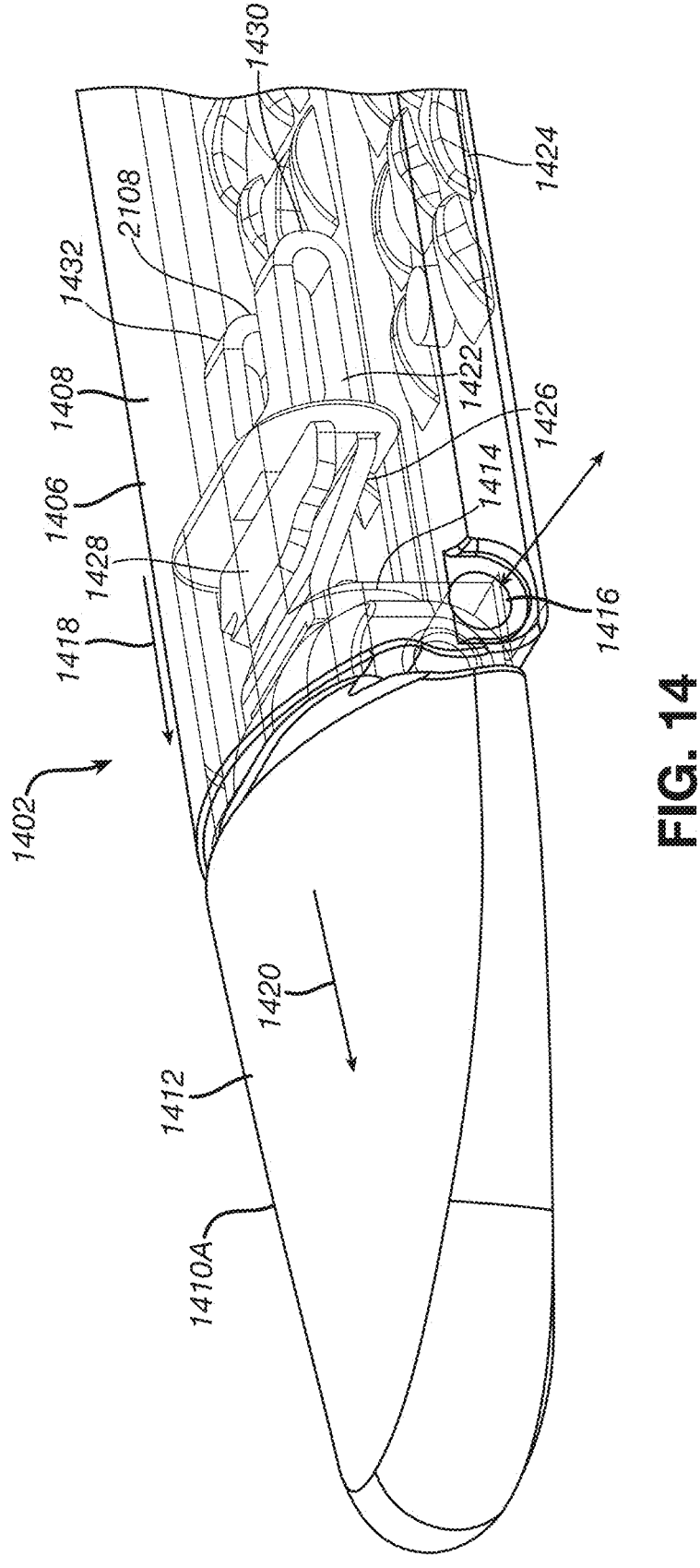
FIG. 14 depicts a perspective view of a distal portion of another anvil jaw configured for use with the surgical instruments described herein with a distal tip shown in a straight orientation.

Furthermore, while distal tips with bodies, i.e., portions which extend distally from the distal jaw end, having particular shapes or profiles are depicted, other distal tip body shapes or profiles may also be used with the disclosed embodiments. For example, FIG. 14 depicts a distal tip 1410A with a body 1412 having a rounded tapered shape/profile. FIG. 22 depicts an elongated distal tip 14010B with a body 1412 having a rounded and/or tapered shape/profile as well as a recessed portions. The embodiments discussed below may be used with any distal tip body shape or profile, e.g., having varying degree of roundness, varying thickness, varying length and made with various materials including rigid or resilient materials throughout or over-molded over an internal structure, etc. such as the distal tips disclosed in U.S. Pat. No. 11,564,687 entitled "METHOD OF SURGICAL STAPLING WITH END EFFECTOR COMPONENT HAVING A CURVED TIP," incorporated by reference herein.

The term "discrete" and variations thereof as used herein in connection with the discretely positionable distal tips shown in FIGS. 14-39B means predefined, where each discrete position of a distal tip relative to its respective jaw body is predefined by specific structural features of the distal tip and/or other portions of the respective end effector jaw. "Discrete" and variations thereof as used herein are not intended to encompass configurations in which a distal tip is configured to transition between various positions relative to a respective jaw body purely by elastic or plastic deformation of the distal tip.

A. Anvil Jaw Having Continuously Loaded Spring and Toggle Tip

Figure 15:
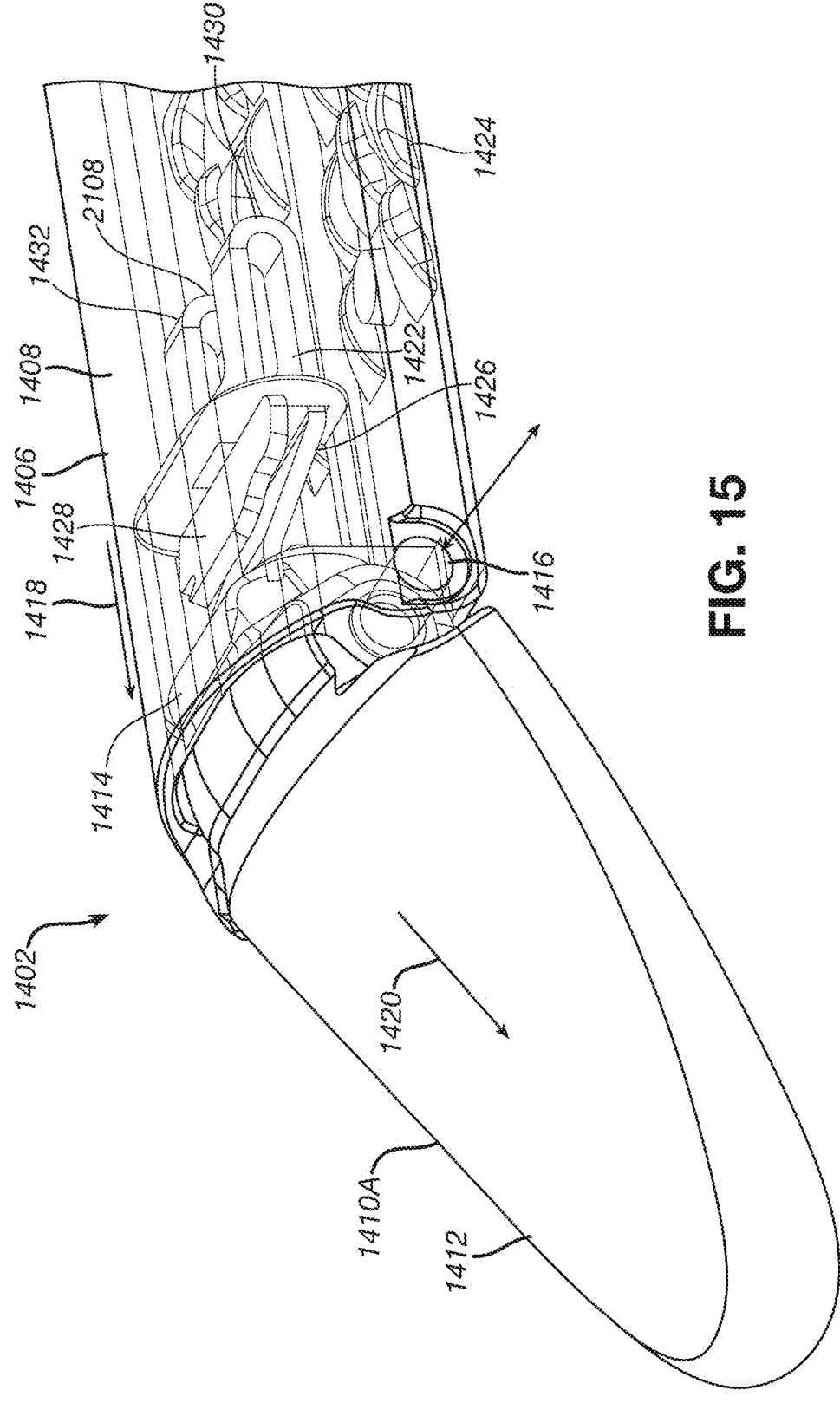
FIG. 15 depicts the anvil jaw of FIG. 14 with the distal tip shown in an angled orientation.
Figures 44A, 44B, 44C:
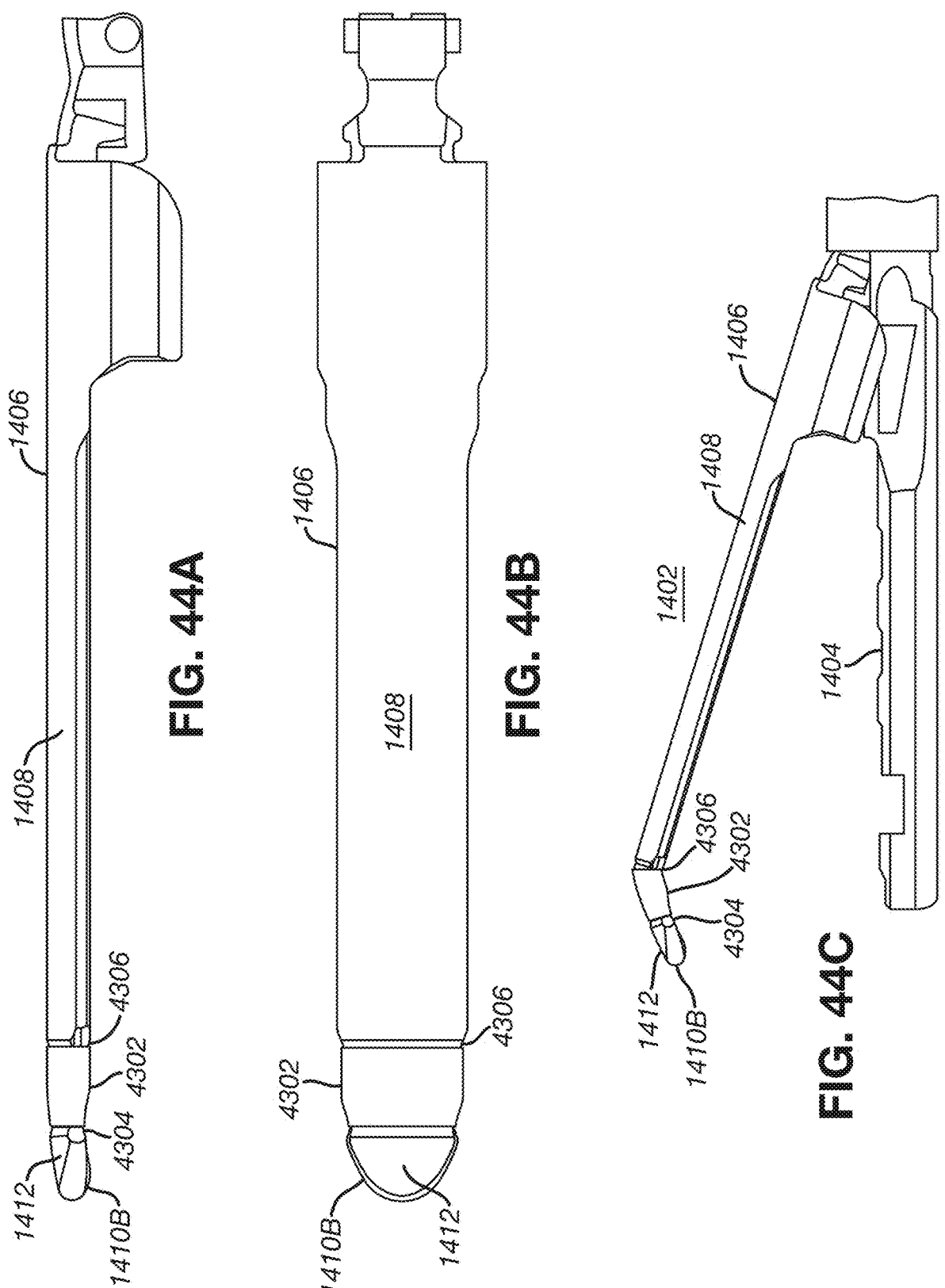
FIG. 44A depicts a side view of an anvil jaw with a cover according to one embodiment.
FIG. 44B depicts a top down view of an anvil jaw with a cover according to one embodiment.
FIG. 44C depicts a perspective view of an end effector with a cover according to one embodiment.
Figure 45:
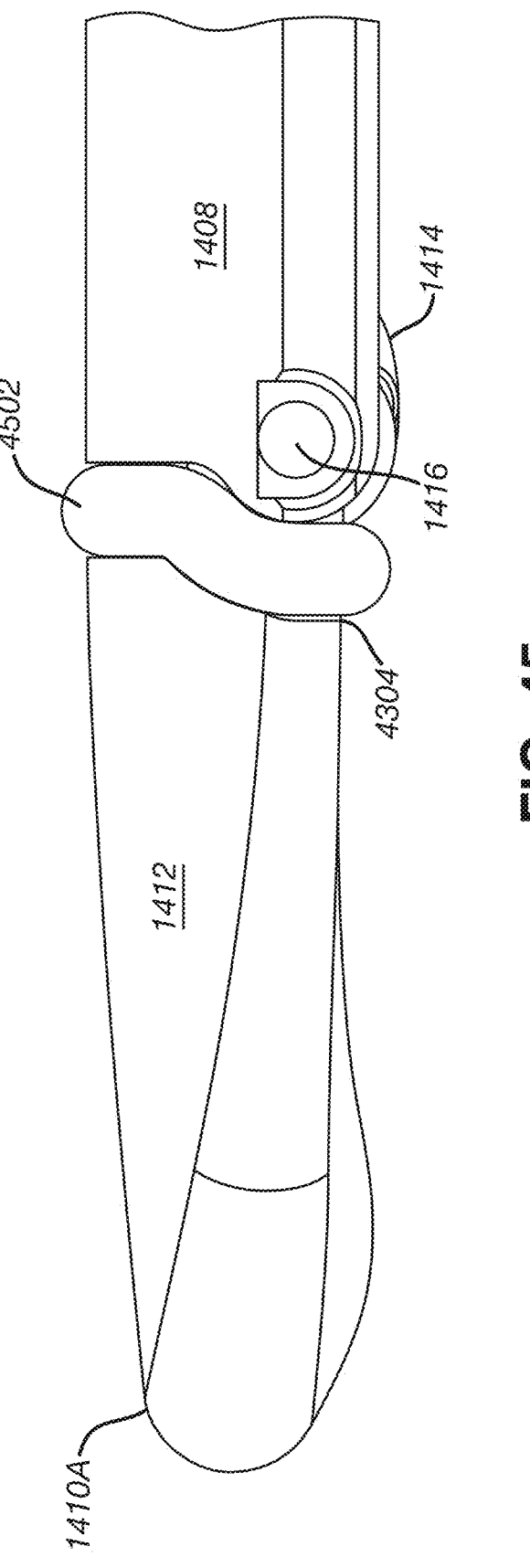
FIG. 45 depicts a side view of a distal end of an anvil jaw with an o-ring according one embodiment.
Figure 46:
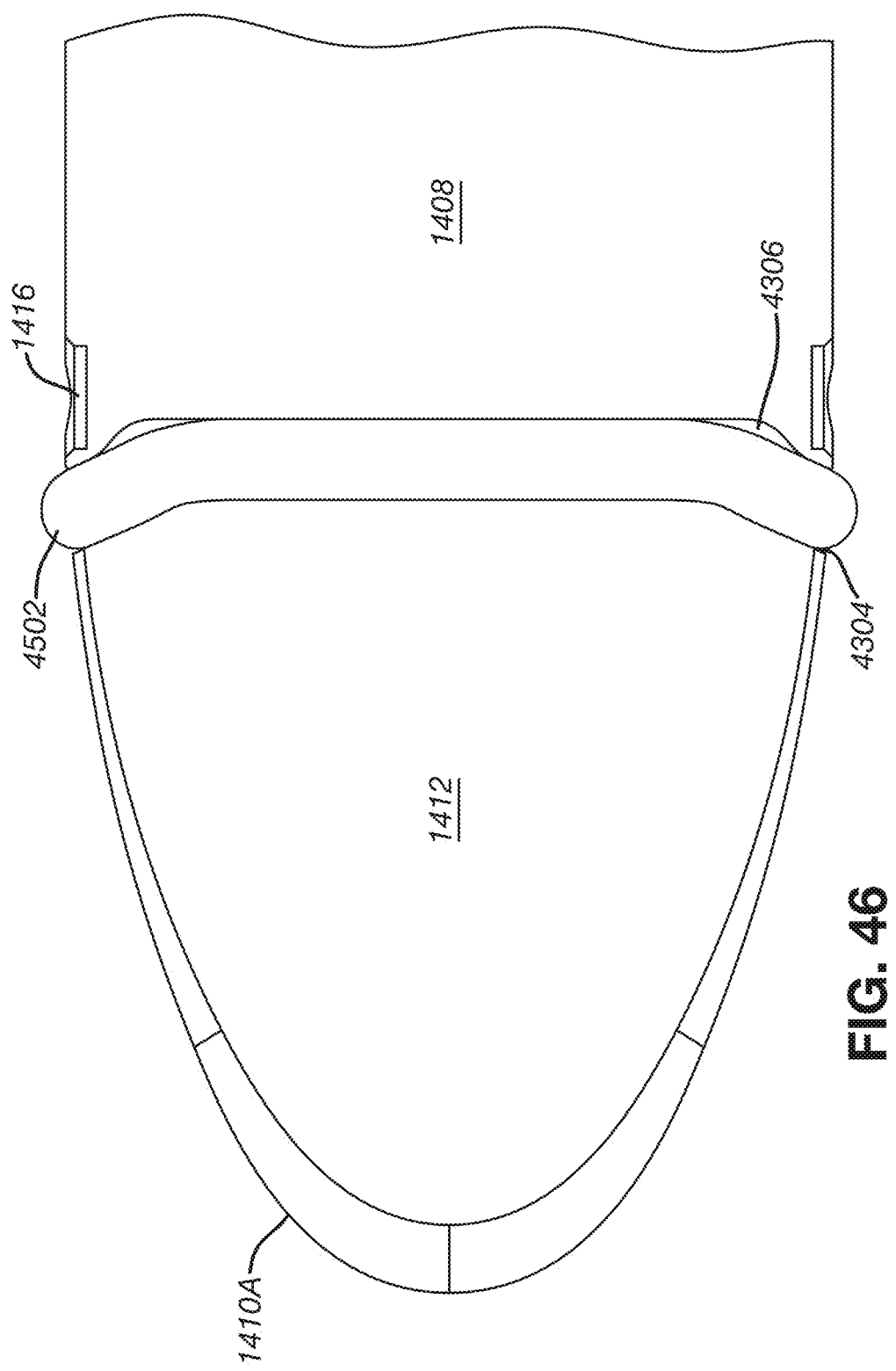
FIG. 46 depicts a top down view of the distal end of the anvil jaw of FIG. 45.
Figure 47:
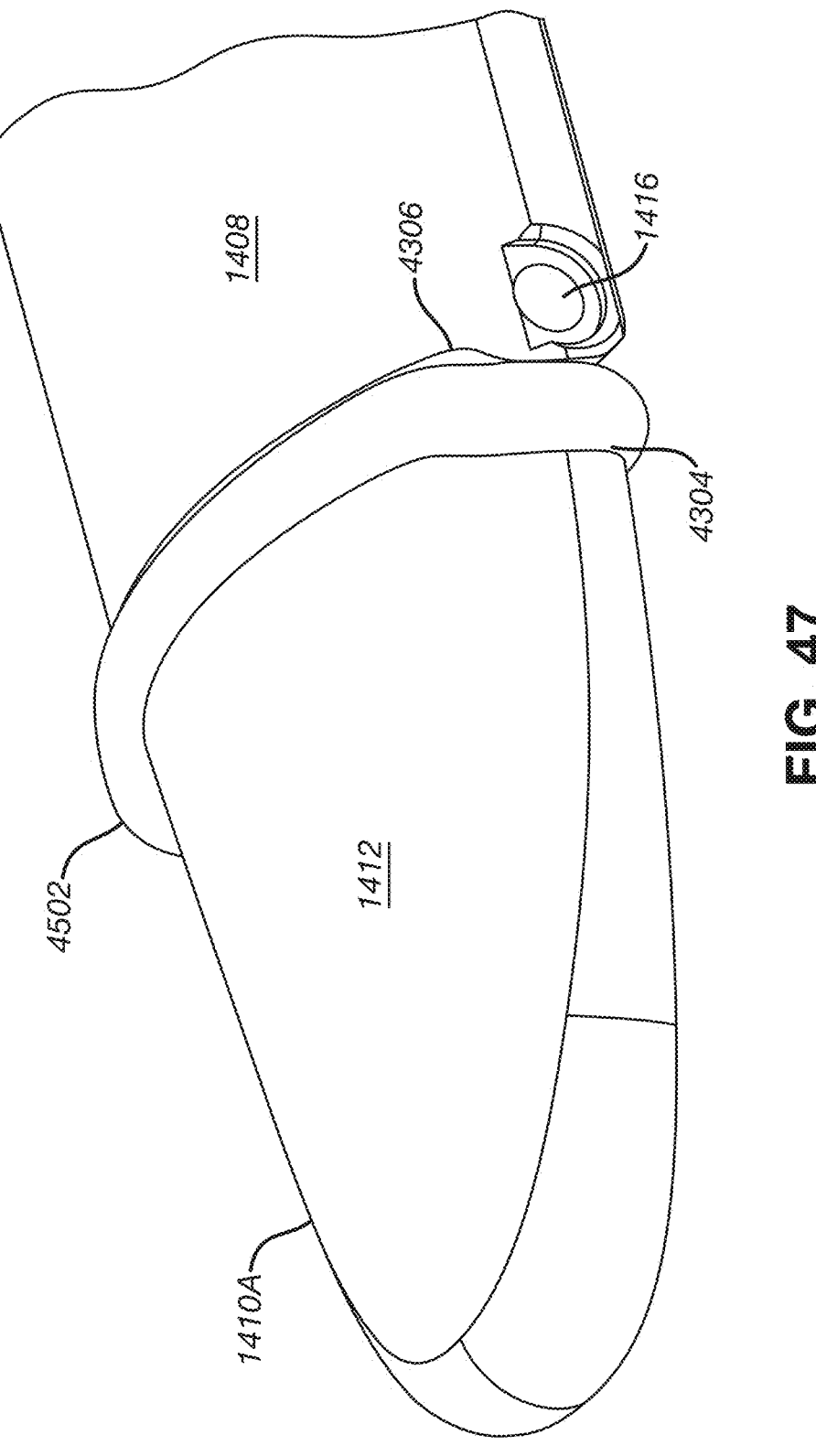
FIG. 47 depicts a front perspective view of the distal end of the anvil jaw of FIG. 45.
Figure 48:
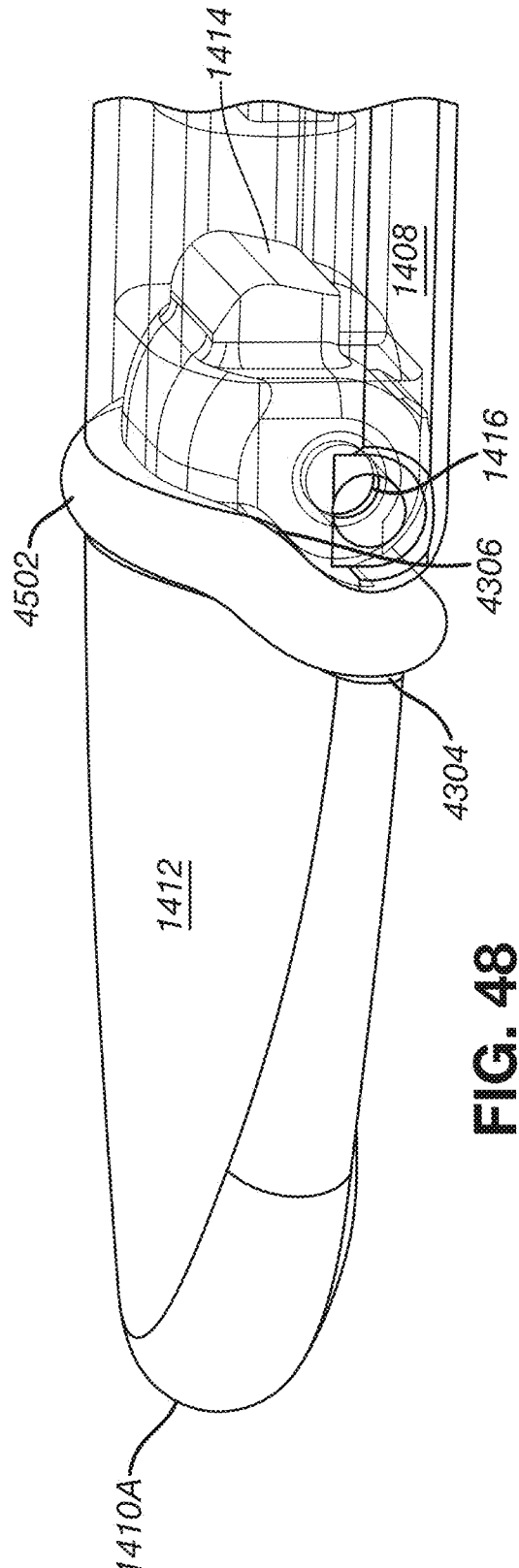
FIG. 48 depicts a side perspective view of the distal end of the anvil jaw of FIG. 45.

FIGS. 14-21 show a distal end of a portion of an end effector (1402), shown in FIG. 44C, comprising a first jaw (1404) and a second jaw (1406) configured to cooperate with the first jaw (1404) to clamp and staple tissue with a plurality of staples as described herein. The second jaw (1406), e.g., an anvil jaw, includes a jaw body (1408) extending longitudinally along a jaw body axis (1418). A distal tip (1410A, 1410B) is movably/pivotably disposed distal to the jaw body (1408) and extends longitudinally along a distal tip axis (1420). The distal tip (1410A, 1410B) is pivotable, about a pivot axis (1416) that extends transversely to the jaw body axis (1418), between a first discrete position and a second discrete position different from the first discrete position, wherein, as shown in FIG. 14, in the first discrete position the distal tip axis (1420) assumes a first orientation relative to the jaw body axis (1418), e.g., parallel thereto or straight, and, as shown in FIG. 15, in the second discrete position the distal tip axis (1420) assumes a second orientation relative to the jaw body axis (1418) different from the first orientation, e.g., non-parallel thereto or angled. The distal tip (1410A, 1410B) includes a body (1412) which extends distal to the pivot axis (1416) and a protrusion (1414) which extends proximal to the pivot axis (1416) and wherein the body (1412) and protrusion (1414) move in opposing directions about the pivot axis (1416).

The pivot axis (1416) may comprise a pivot or hinge structure or clevis/shackle, e.g., a U-shaped or forked connector formed in either the distal end of the anvil jaw (1406) body (1408) or proximal portion of the distal tip (1410A, 1410B) within which the distal tip (1410A, 1410B) can be fastened by means of a pin passing through the ends of the connector, wherein the distal end of the jaw body (1408) and an intermediate portion of the distal tip (1410A, 1410B) between the body (1412) and proximal protrusion (1414) each include bore holes which are coaxially aligned when the distal tip (1410A, 1410B) is assembled to the jaw body (1408) and through which a pin is inserted to pivotably affix the distal tip (1410A, 1410B) thereto.

For example, the distal end of the jaw body (1408) includes a pair of arms that extend distally. The arms include bores that are configured to align coaxially with a corresponding bore formed in a proximal end portion of distal tip (1410A, 1410B) to receive a pivot pin and thereby pivotably couple distal tip (1410A, 1410B) with the jaw body (1408). In this manner, the bores and pivot pin define a longitudinally fixed pivot axis, or axis of rotation, about which distal tip (1410A, 1410B) is configured to pivot (or "toggle") between the first and second discrete positions/orientations, and which extends transversely relative to a longitudinal axis (1418) of jaw body (1408). The pivot pin may be press fit, threaded, or glued, for example, to the distal tip (1410A, 1410B) and, in some versions, may be removable.

As described, in one implementation, the first jaw (1404) comprises a staple cartridge (2102) that houses a plurality of staples and the second jaw (1406) is an anvil jaw and comprises a plurality of staple forming pockets (1424) configured to form the staples, wherein the first and second jaws (1404, 1406) are configured to transition from an open state, wherein the first and second jaws (1404, 1406) are non-parallel, to a closed state, wherein the first and second jaws (1404, 1406) are nominally parallel, to clamp and staple tissue with the staples.

One of the first and second discrete positions may be configured for marching the first and second jaws (1404, 1406) through tissue and the other of the first and second discrete positions may be configured for gathering tissue between the first and second jaws (1404, 1406) when the first and second jaws (1404, 1406) are transitioned from the open state to the closed state. For example, when the distal tip is (1410A, 14010B) in the first orientation, the distal tip (1410A, 14010B) is nominally parallel to the jaw body axis (1418) and when in the second orientation, the distal tip (1410A, 14010B) is at an acute angle relative to the jaw body axis (1418). In the second orientation, the angle of the distal tip (1410A, 1410B) may be parallel to a distal end, i.e., nose, of a staple cartridge (2102) inserted in the first jaw (1404). In one implementation, in the second orientation, the distal tip (1410A, 1410B) may remain spaced apart from the distal end of the first jaw (1404) or the distal end of the staple cartridge (2102) inserted therein, regardless of whether tissue is present between the jaws (1404, 1406) or not. In an alternative implementation at least a portion of the distal tip (1410A, 1410B), i.e., a portion of the underside thereof, may contact the distal end of the first jaw (1404) or the distal end of the staple cartridge (2102) inserted therein when in the second orientation with no tissue present between and/or extending from the jaws (1404, 1406).

In one embodiment, the jaw body (1408) includes at least first and second stops (1602, 1702A, 1702B, 1702C), also referred to as stop surfaces, configured to constrain the pivotable motion of the distal tip (1410A, 1410B), i.e., to constrain the distal tip (1410A, 1410B) to a predefined range of angular motion relative to the jaw body (1408). In one implementation, the first stop (1602) positioned to abut a first portion (1604) of the distal tip when in the first discrete position and the second stop (1702A, 1702B, 1702C) is positioned to abut a second portion (1704A, 1704B, 1704C) of the distal tip when in the second discrete position. In one implementation the stops (1602, 1704A, 1704B, 1704C) are integrally formed in the jaw body (1408), e.g., at a time of manufacture thereof. In an alternative implementation, the stops (1602, 1702A, 1702B, 1702C) are formed in or otherwise added to the jaw body (1408) subsequent to the manufacture thereof. The stops (1602, 1702A, 1702B, 1702C) may take the form of protrusions or surfaces configured to interfere with the movement of the distal protrusion by impeding or otherwise limiting or restricting the extent of travel/movement of the first and second portions (1604, 1704A, 1704B, 1704C). It will be appreciated that the number and arrangement of stops is implementation dependent and fewer or additional stops may be implemented. In one implementation, the number and placement of stops is used to control the tactile rigidity of distal tip (1410A, 1410B) when in one of the discrete positions and to provide tactile feedback to a user as to the limits/range of the motion of the distal tip (1410A, 1410B) in either direction of movement.

Figure 16:
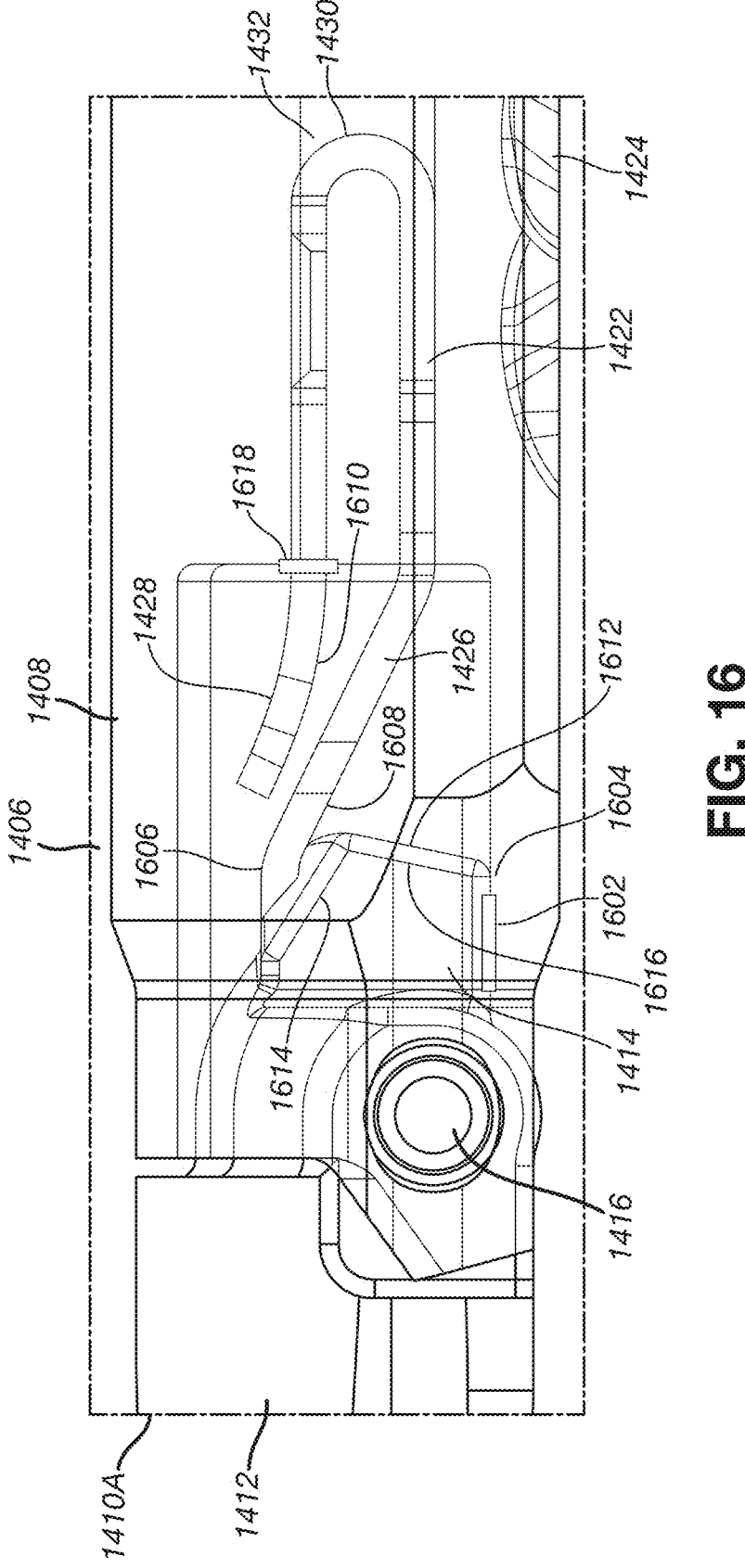
FIG. 16 depicts a side view of the anvil jaw of FIGS. 14 and 15 according to one embodiment.
Figures 17A, 17B:
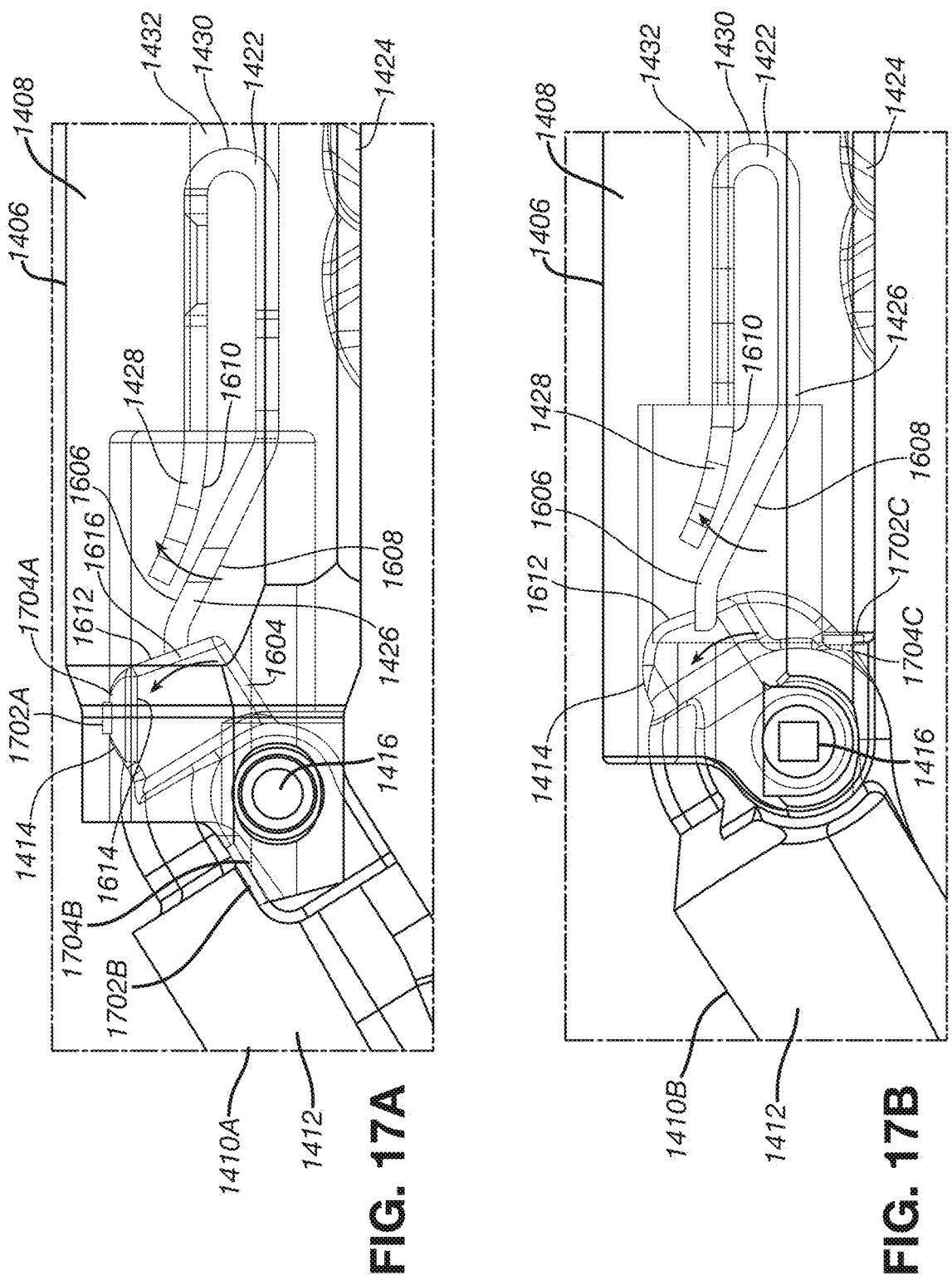
FIG. 17A depicts a side view of the anvil jaw of FIGS. 14 and 15 according to one embodiment.
FIG. 17B depicts a side view of the anvil jaw of FIGS. 14 and 15 according to one embodiment.
Figure 18:
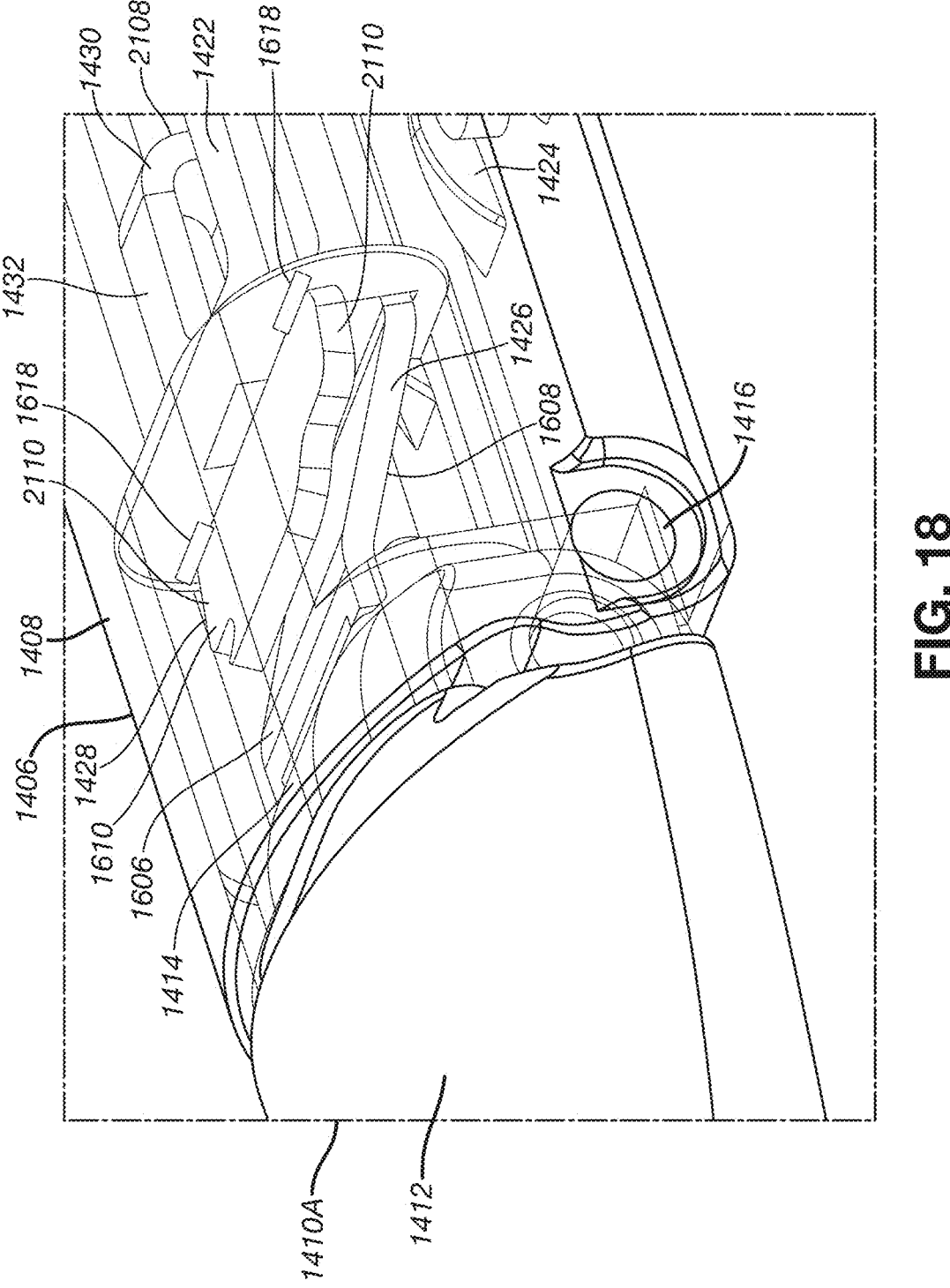
FIG. 18 depicts a distal end the anvil jaw of FIG. 14 with the distal tip shown in a straight orientation according to one embodiment.
Figures 20A, 20B:
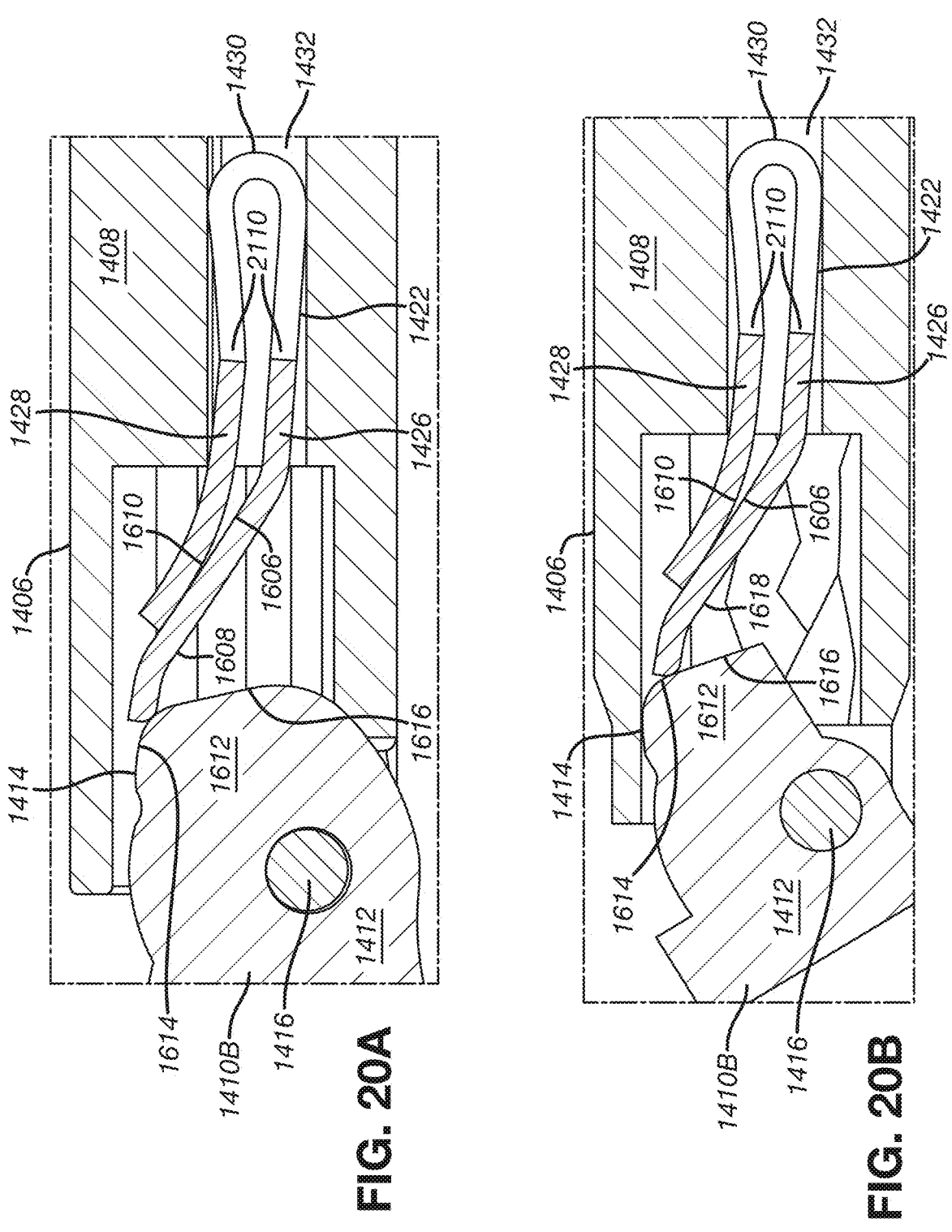
FIGS. 20A and 20B depicts a distal end the anvil jaw of FIG. 14 with the distal tip shown in an installed position according to one embodiment.
Figure 21:
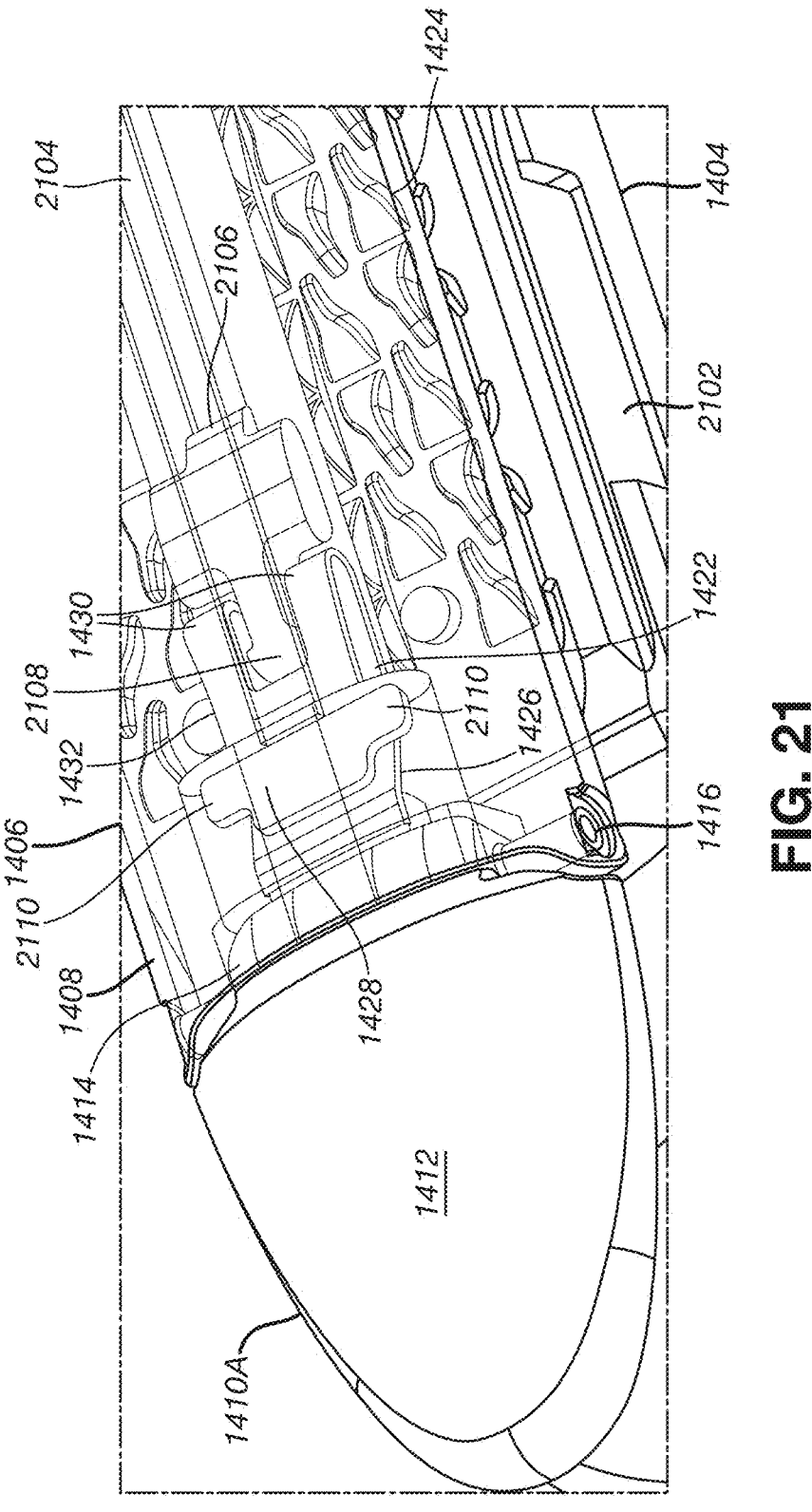
FIG. 21 depicts a distal end the anvil jaw of FIG. 14 with the distal tip shown in a straight orientation according to one embodiment.
Figure 32A:
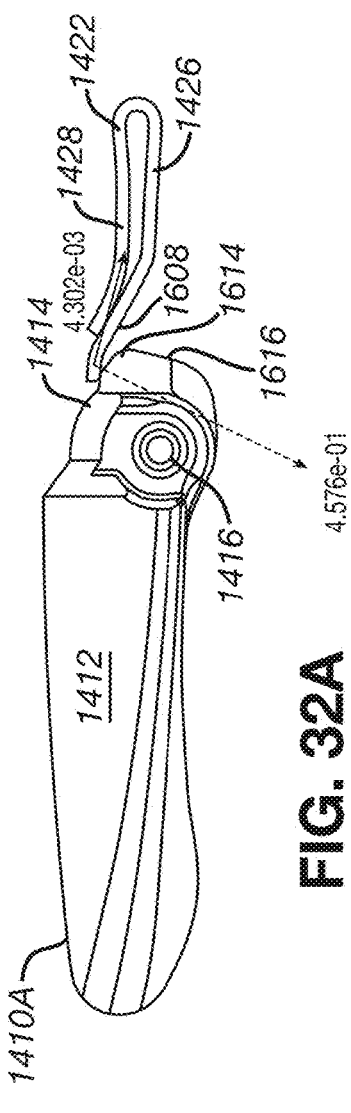
FIG. 32A depicts a diagram showing direction of forces exerted on a proximal protrusion of a distal tip by a spring at a first time of a time period over which the distal tip is transitioned from a straight to an angled orientation and back according to one embodiment.
Figure 32B:
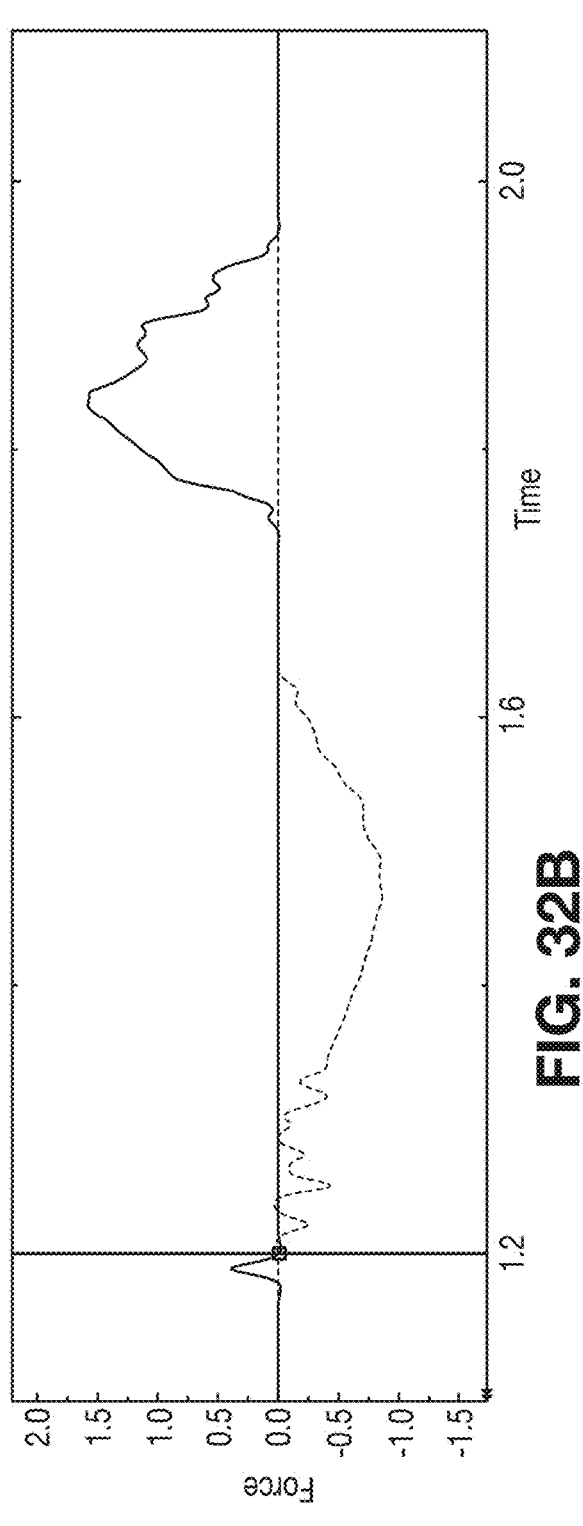
FIG. 32B depicts a graph, including an indicator coordinated with the orientation of the distal tip shown in FIG. 32A, of the amount of force exerted by the spring on a proximal protrusion of the distal tip over a time period over which the distal tip is transitioned from a straight to an angled orientation and back according to one embodiment.
Figure 33A:
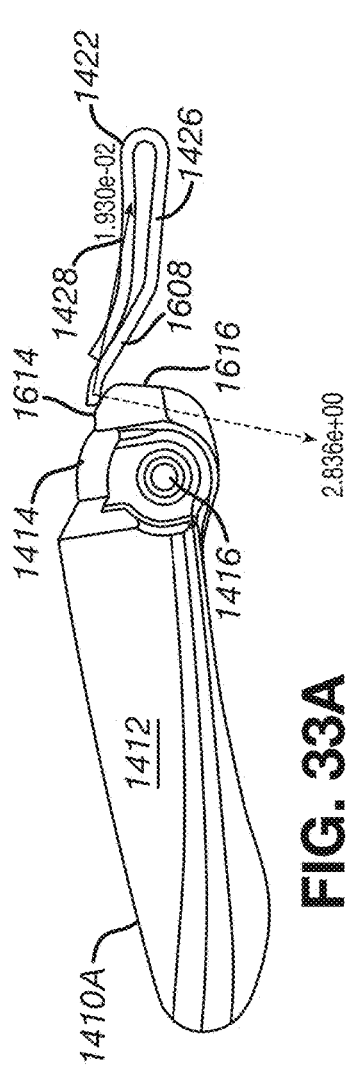
FIG. 33A depicts a diagram showing direction of forces exerted on a proximal protrusion of a distal tip by a spring at a second time of a time period over which the distal tip is transitioned from a straight to an angled orientation and back according to one embodiment.
Figure 33B:
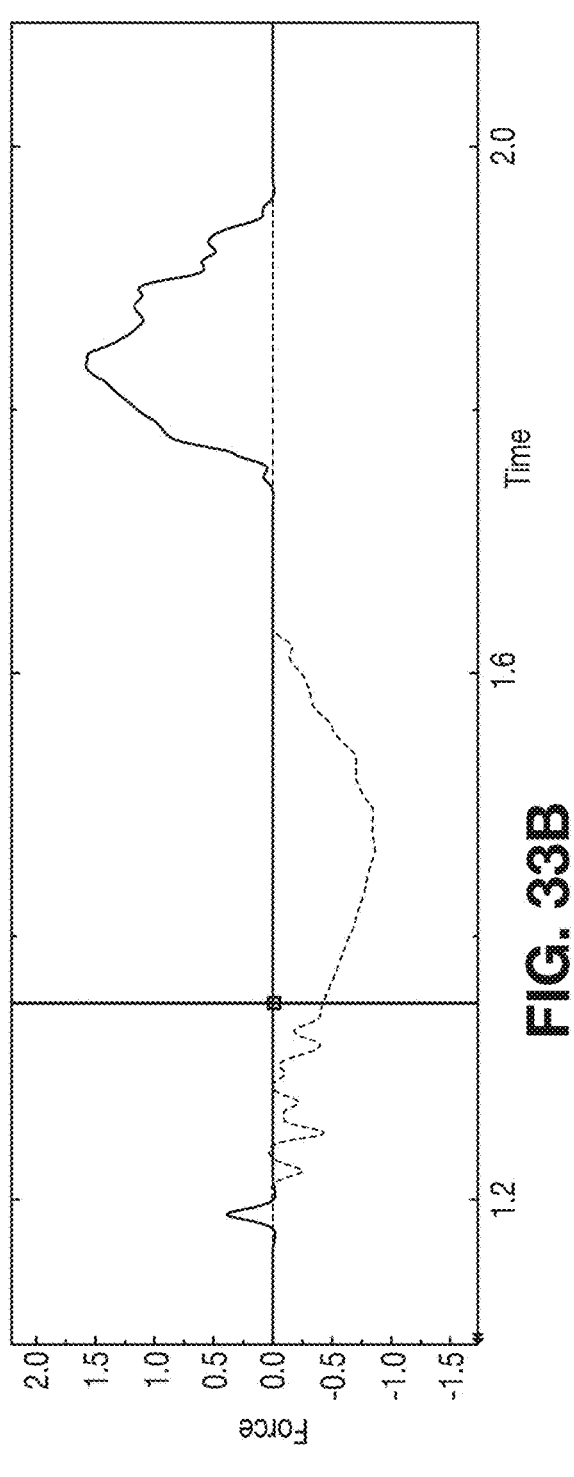
FIG. 33B depicts a graph, including an indicator coordinated with the orientation of the distal tip shown in FIG. 33A, of the amount of force exerted by the spring on a proximal protrusion of the distal tip over a time period over which the distal tip is transitioned from a straight to an angled orientation and back according to one embodiment.
Figure 34A:
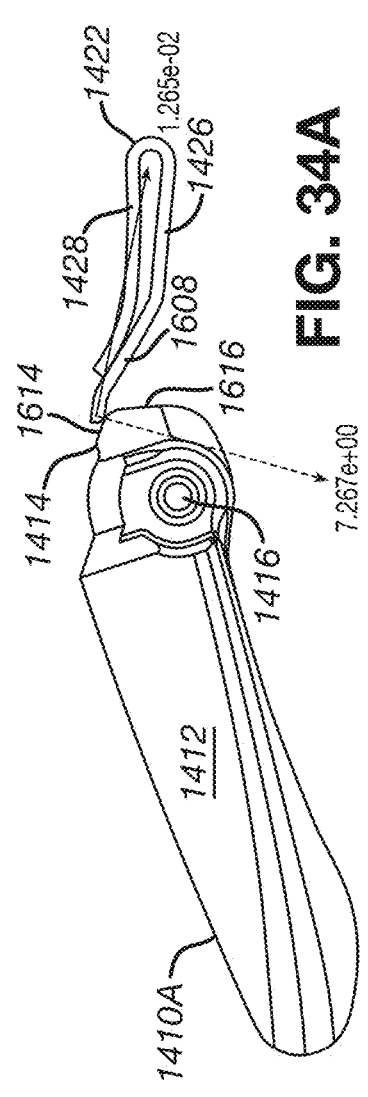
FIG. 34A depicts a diagram showing direction of forces exerted on a proximal protrusion of a distal tip by a spring at a third time of a time period over which the distal tip is transitioned from a straight to an angled orientation and back according to one embodiment.
Figure 34B:
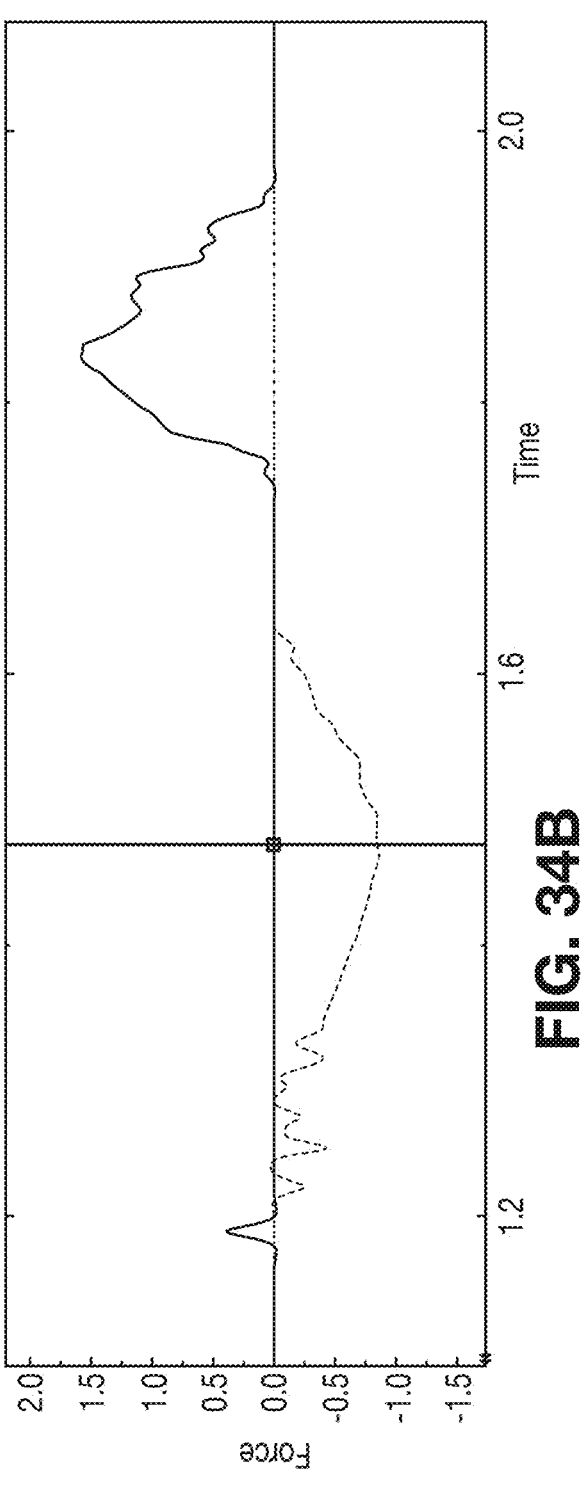
FIG. 34B depicts a graph, including an indicator coordinated with the orientation of the distal tip shown in FIG. 34A, of the amount of force exerted by the spring on a proximal protrusion of the distal tip over a time period over which the distal tip is transitioned from a straight to an angled orientation and back according to one embodiment.
Figure 35A:
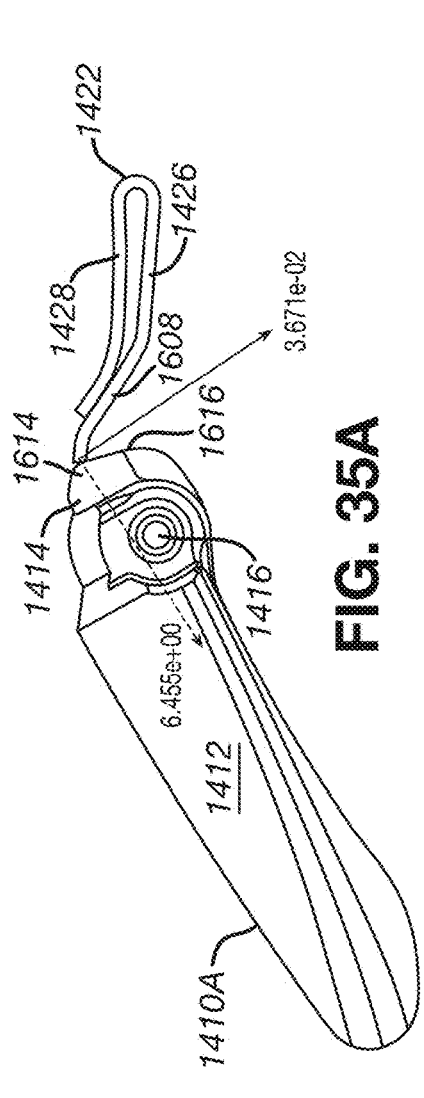
FIG. 35A depicts a diagram showing direction of forces exerted on a proximal protrusion of a distal tip by a spring at a fourth time of a time period over which the distal tip is transitioned from a straight to an angled orientation and back according to one embodiment.
Figure 35B:
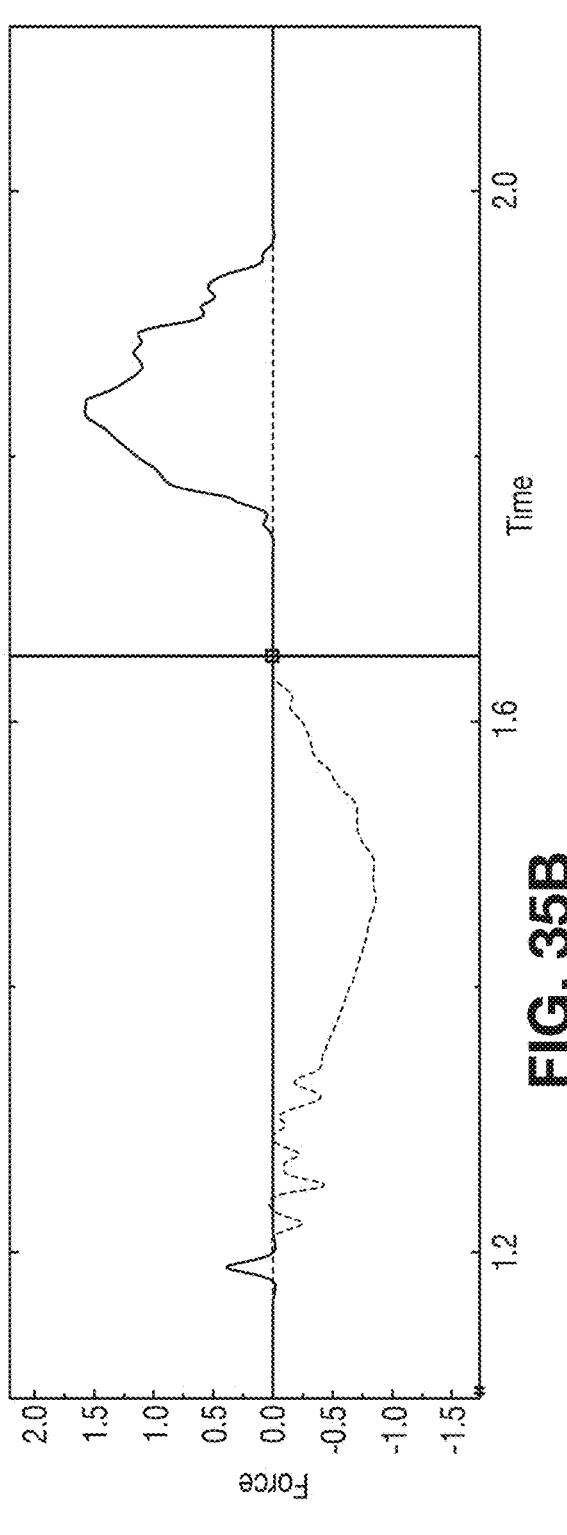
FIG. 35B depicts a graph, including an indicator coordinated with the orientation of the distal tip shown in FIG. 35A, of the amount of force exerted by the spring on a proximal protrusion of the distal tip over a time period over which the distal tip is transitioned from a straight to an angled orientation and back according to one embodiment.
Figures 36A, 36B:
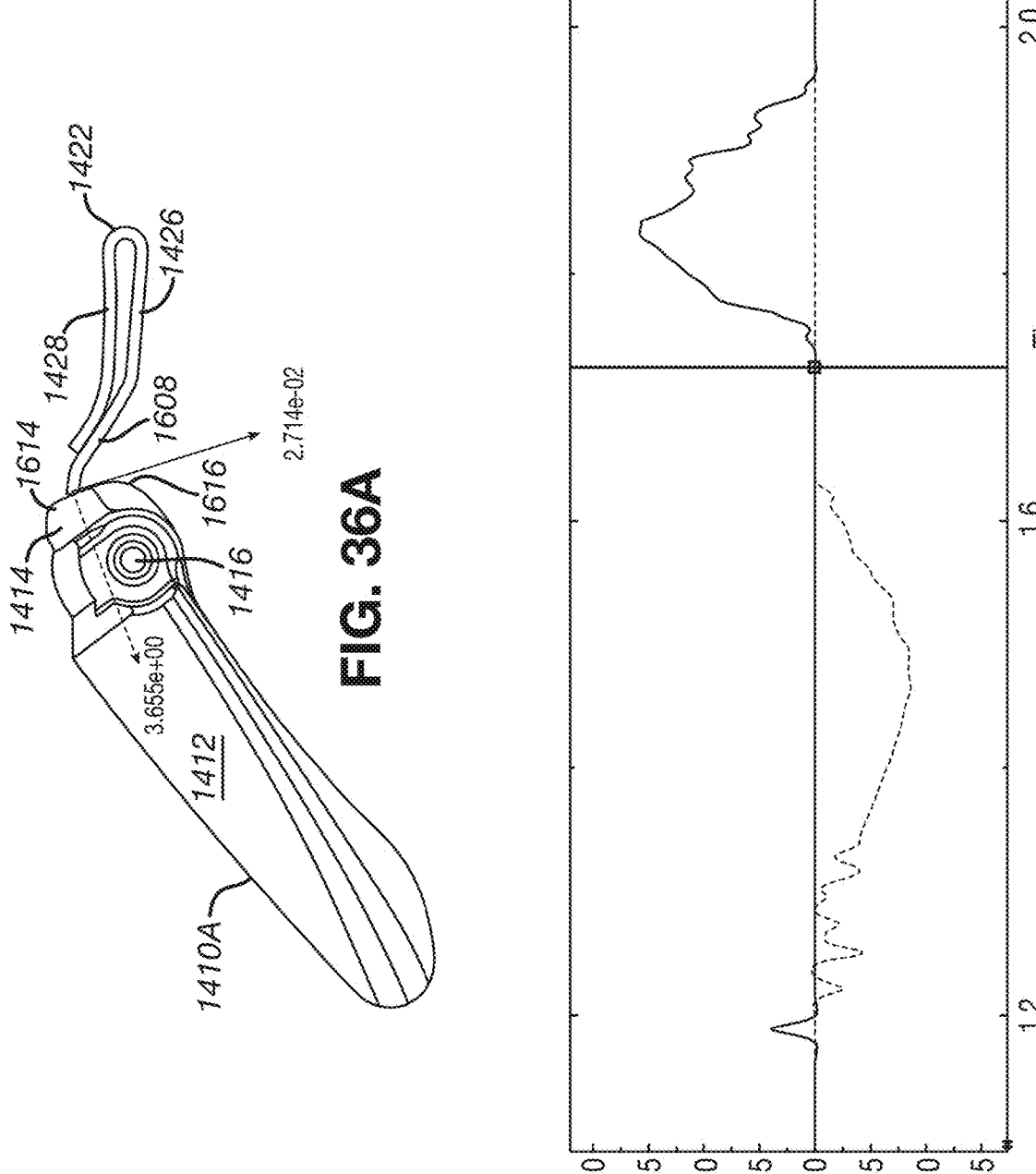
FIG. 36A depicts a diagram showing direction of forces exerted on a proximal protrusion of a distal tip by a spring at a fifth time of a time period over which the distal tip is transitioned from a straight to an angled orientation and back according to one embodiment.
FIG. 36B depicts a graph, including an indicator coordinated with the orientation of the distal tip shown in FIG. 36A, of the amount of force exerted by the spring on a proximal protrusion of the distal tip over a time period over which the distal tip is transitioned from a straight to an angled orientation and back according to one embodiment.
Figure 37A:
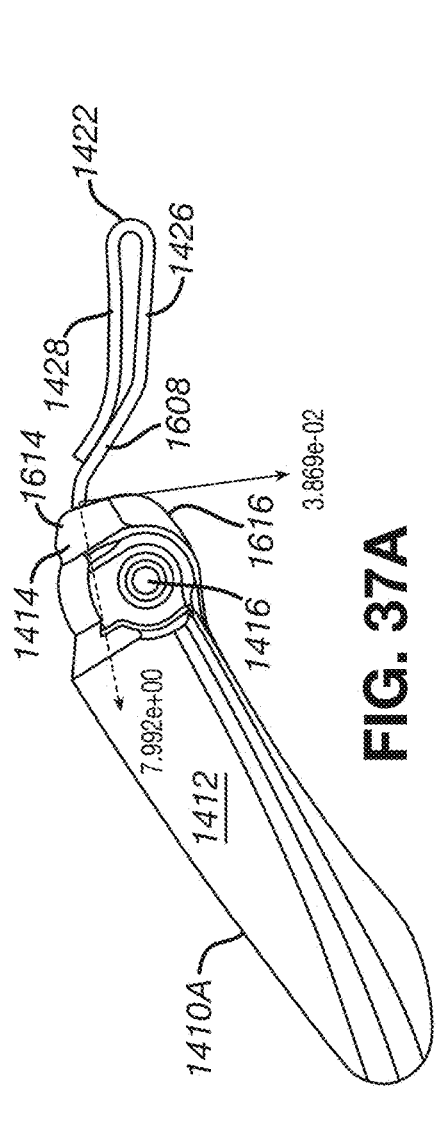
FIG. 37A depicts a diagram showing direction of forces exerted on a proximal protrusion of a distal tip by a spring at a sixth time of a time period over which the distal tip is transitioned from a straight to an angled orientation and back according to one embodiment.
Figure 37B:
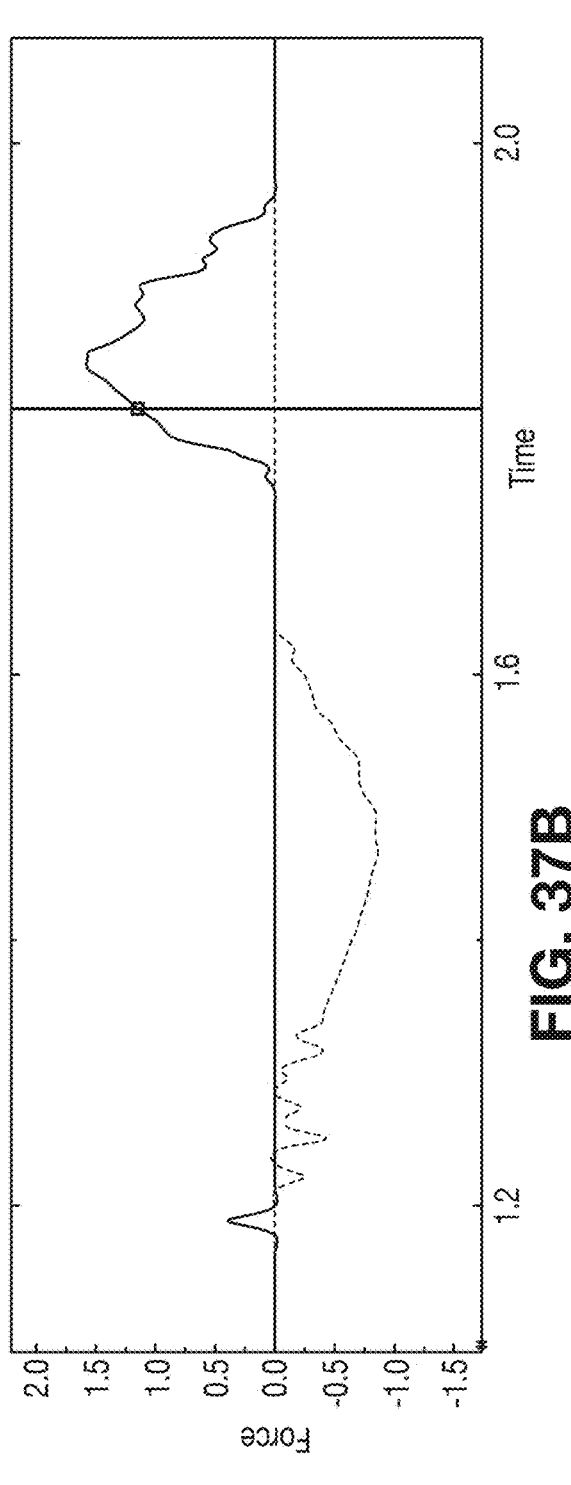
FIG. 37B depicts a graph, including an indicator coordinated with the orientation of the distal tip shown in FIG. 37A, of the amount of force exerted by the spring on a proximal protrusion of the distal tip over a time period over which the distal tip is transitioned from a straight to an angled orientation and back according to one embodiment.
Figure 38A:
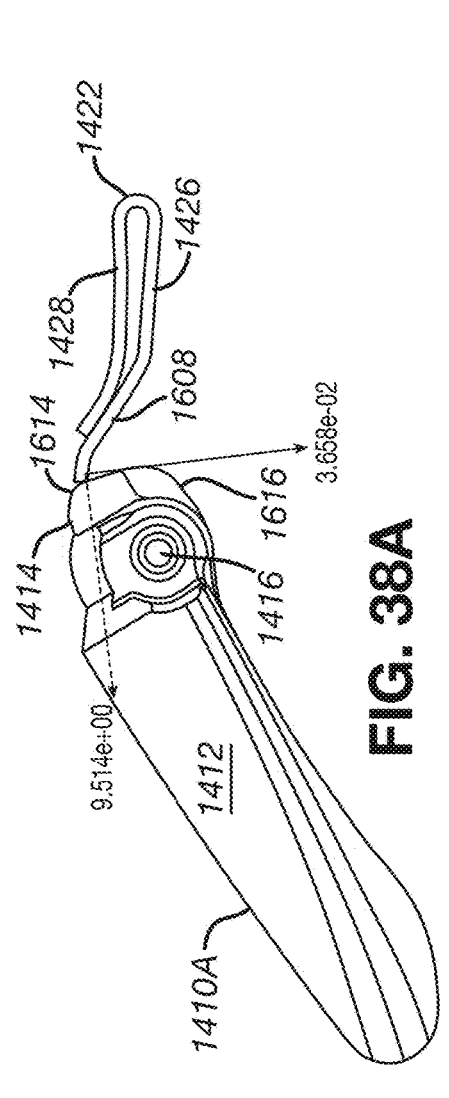
FIG. 38A depicts a diagram showing direction of forces exerted on a proximal protrusion of a distal tip by a spring at a seventh time of a time period over which the distal tip is transitioned from a straight to an angled orientation and back according to one embodiment.
Figure 38B:
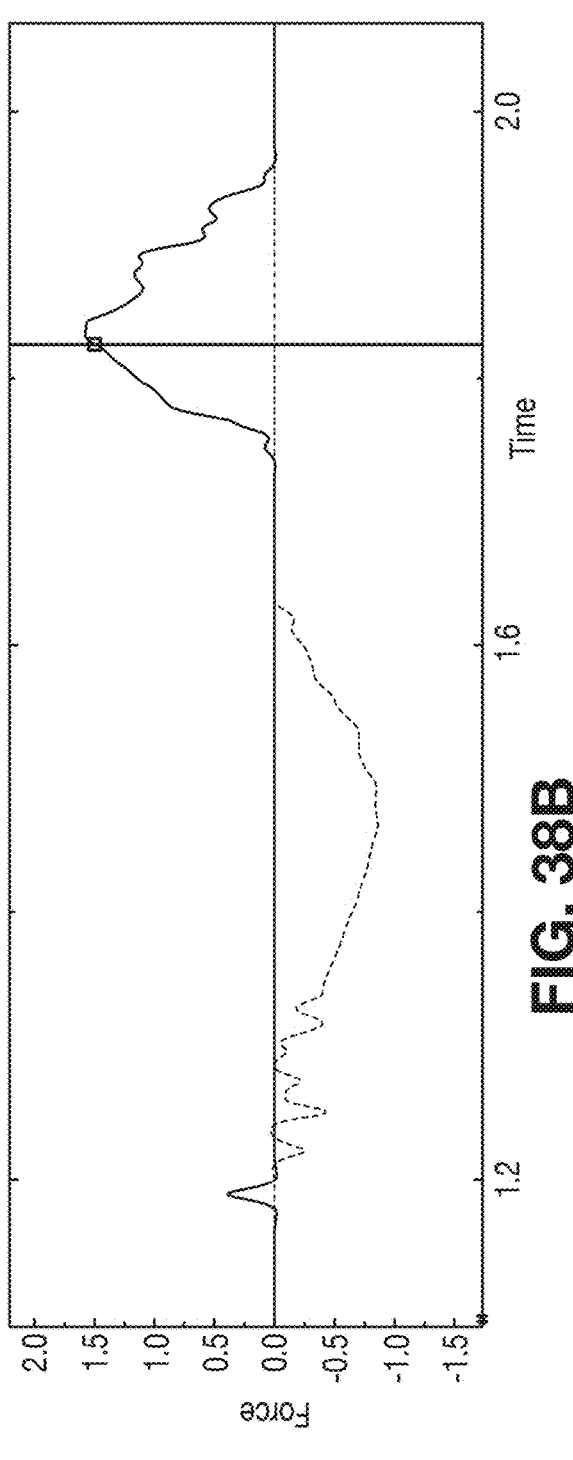
FIG. 38B depicts a graph, including an indicator coordinated with the orientation of the distal tip shown in FIG. 38A, of the amount of force exerted by the spring on a proximal protrusion of the distal tip over a time period over which the distal tip is transitioned from a straight to an angled orientation and back according to one embodiment.
Figure 39A:
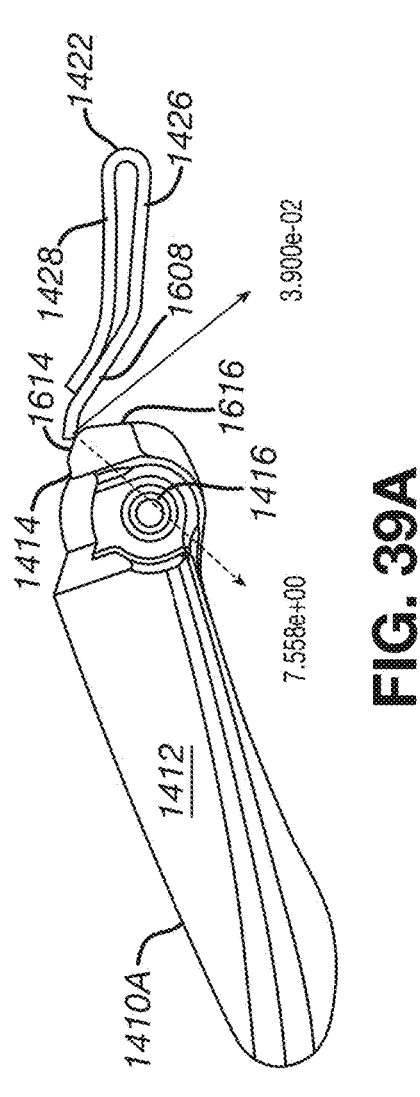
FIG. 39A depicts a diagram showing direction of forces exerted on a proximal protrusion of a distal tip by a spring at an eighth time of a time period over which the distal tip is transitioned from a straight to an angled orientation and back according to one embodiment.
Figure 39B:
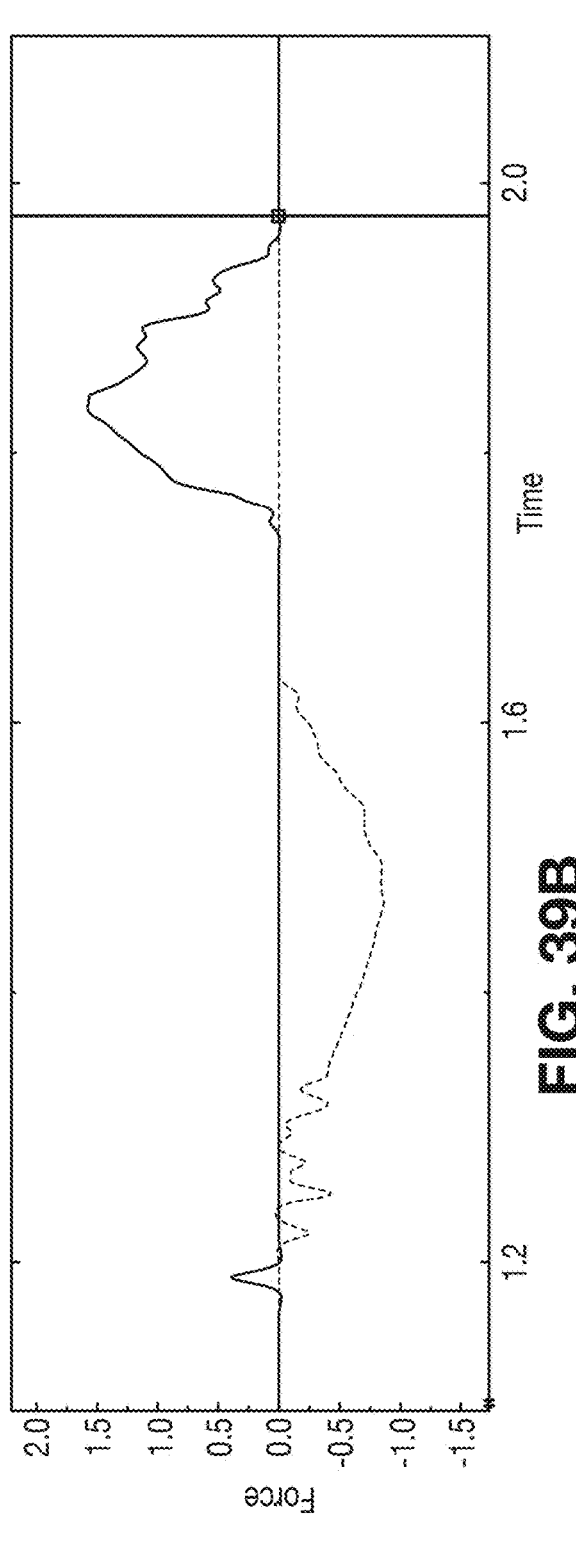
FIG. 39B depicts a graph, including an indicator coordinated with the orientation of the distal tip shown in FIG. 39A, of the amount of force exerted by the spring on a proximal protrusion of the distal tip over a time period over which the distal tip is transitioned from a straight to an angled orientation and back according to one embodiment.

In one implementation, as shown in FIG. 16, the first stop (1602) is located on the bottom of a cavity (1432) formed in the jaw body (1408) to receive the spring (1422) and proximal protrusion (1414) of the distal tip (1410A, 1410B). Wherein the first portion (1604) of the proximal protrusion (1414) is a lower surface thereof, the first stop (1602) is arranged to abut the first portion (1604), and prevent further downward movement thereof and thereby prevent further upward movement of the distal tip body (1412), when the distal tip (1410A, 1410B) is in the first, e.g., straight/parallel, orientation. While not accurately represented in FIG. 16, the spring (1422) deflection, when the distal tip (1410A, 1410B) is in the first, e.g., straight/parallel, orientation, is shown in FIGS. 20A, 32A and 32B. In one implementation, as shown in FIGS. 17A and 17B, one or more additional second stops (1702A, 1702B, 1702C) are formed in the cavity (1432) to abut one or more second portions (1704A, 1704B, 1704C) of the proximal protrusion (1414) when the distal tip (1410A, 1410B) is in the second, e.g., angled/non-parallel, orientation, to prevent further upward movement thereof and thereby prevent further downward movement of the distal tip body (1412). While not accurately represented in FIGS. 17A and 17B, the spring (1422) deflection, when the distal tip (1410A, 1410B) is in the second, e.g., angled/non-parallel, orientation, is shown in FIGS. 20B, 35A-37B. It will be appreciated then that the location of the first and second stops (1602, 1702A, 1702B, 1702C), in concert with the location of the first and second portions (1604, 1704A, 1704B, 1704C) and/or dimensions of the proximal protrusion, may define the range of motion of the distal tip (1410A, 1410B). Further, the number of stops (1602, 1702A, 1702B, 1702C) used to define each of the first and second orientations may vary depending upon the implementation, with fewer or additional stops added, e.g., to improve the rigid feel of the distal tip (1410A, 1410B) when in one of the first or second orientations, and/or enhance the tactile "snap" feel and/or audible indication, as the distal tip (1410A, 1410B) transitions to one of the first or second orientations.

In one implementation, a stop (1702A) is positioned on a bottom surface of an upper portion of the jaw body (1408) above the proximal protrusion (1414), as shown in FIG. 17A, to abut a surface (1704A) of the proximal protrusion (1414) and thereby impede the further upward motion, or distal rotation of the upper portion, of the proximal protrusion (1414) when the distal tip (1410A, 1410B) is in the second/angled orientation. Another stop (1702B) may be used instead or, or in addition to, stop (1702A), and may be referred to as a secondary stop, and positioned on the arm of the jaw body (1408) distal to the pivot (1416) and configured to abut a surface (1704B) of the distal tip body (1412) and thereby further impede downward movement, or proximal rotation of a portion, of the distal tip (1410A, 1410B) when in the second/angled orientation. Alternatively, or in addition thereto, as shown in FIG. 17B, a stop (1702C) may be located on the distal end of the jaw body (1408) proximal to the pivot (1416) and configured to abut a surface (1704C) of the proximal protrusion (1414) and thereby impede the further, e.g., proximal rotation of at least a lower portion of the proximal protrusion (1414) when in the second/angled orientation.

Figure 26:
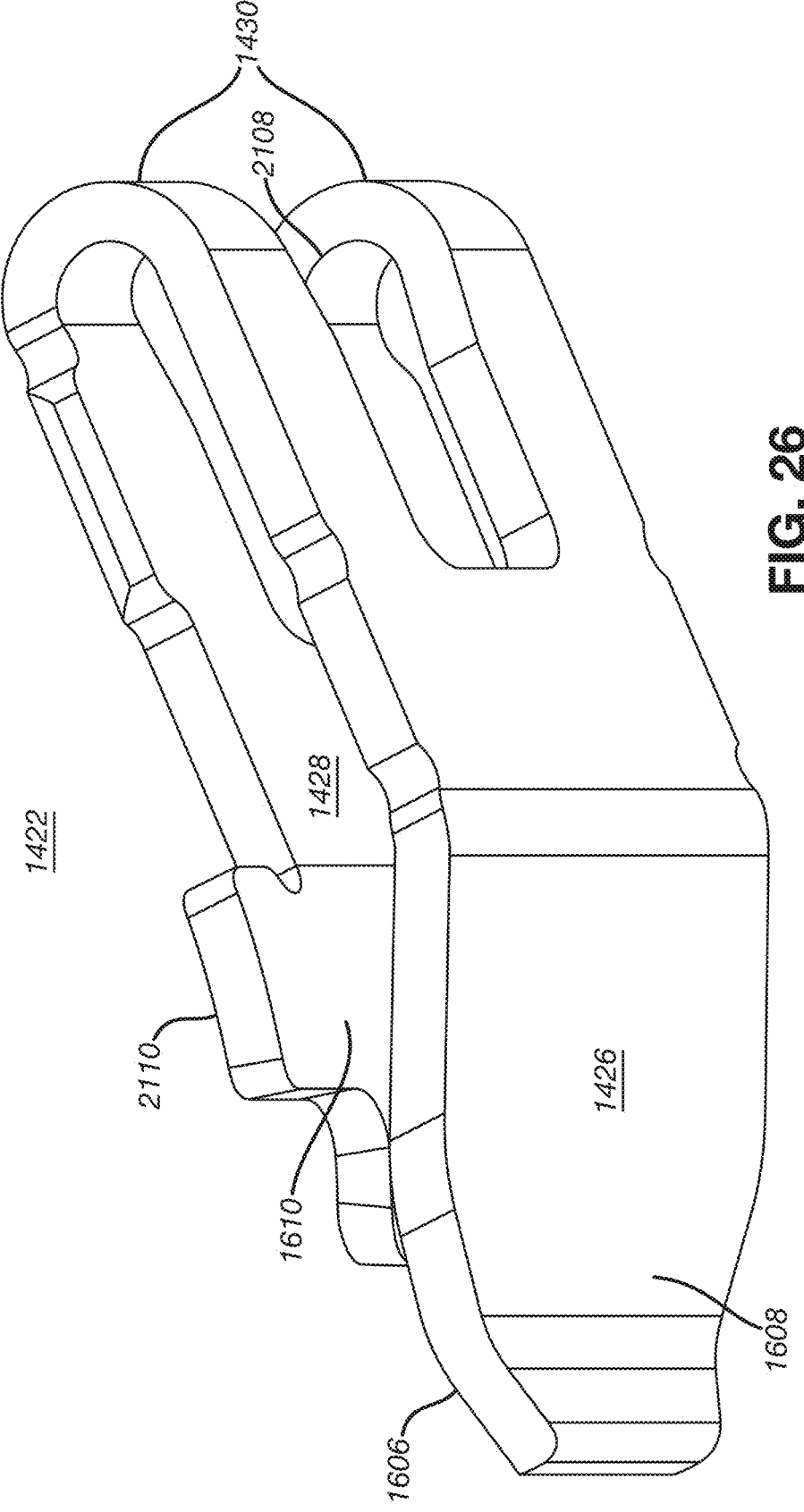
FIG. 26 depicts a bottom perspective view of a spring according to one embodiment.
Figure 27A:
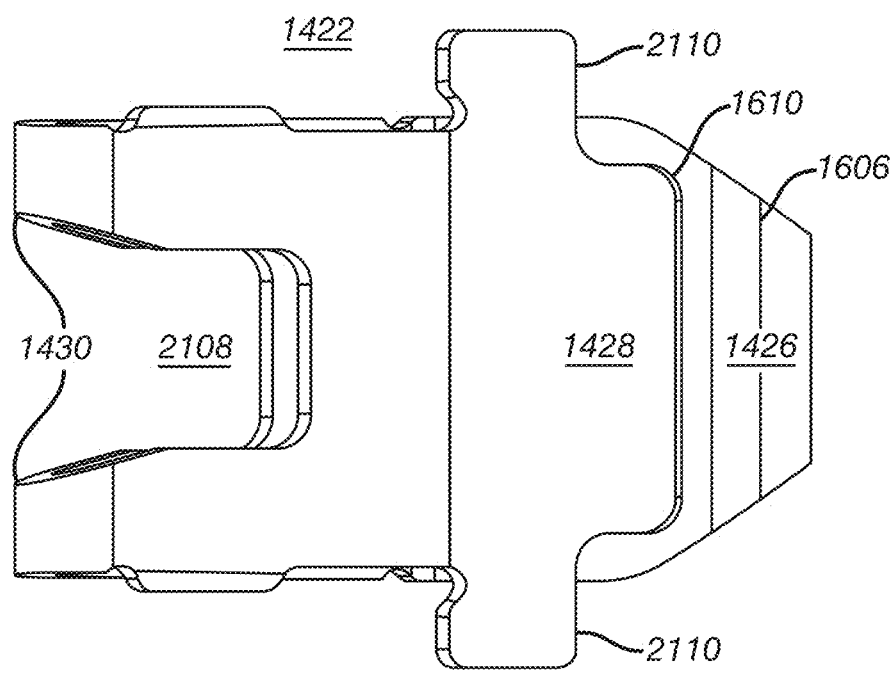
FIG. 27A depicts a top view of the spring of FIG. 26 according to one embodiment.

In one embodiment, the jaw body (1408) further includes a spring (1422), shown in more detail in FIGS. 26-28, proximal to the proximal protrusion (1414) and configured, as shown in FIGS. 24, 25, and 32A-39B, to exert a resilient force, e.g., a spring force or bias, against the proximal protrusion (1414) in a first direction so as to releasably bias the first portion (1604) of the distal tip (1410A, 1410B) against the first stop (1602) when in the first discrete position and exert the resilient force against the proximal protrusion (1414) in a second direction, different from the first direction, so as to releasably bias the second portion (1704A, 1704B, 1704C) against the second stop (1702A, 1702B, 1702C) when in the second discrete position. In one embodiment, the spring (1422) exerts a continuous resilient force, which may be constant or varying in amount, against the proximal protrusion (1414). As the distal tip (1410A, 1410B) is transitioned, e.g., via the application of an external force to the body (1412) in an opposing direction, from one of the first or second discrete positions to the other of the first or second discrete positions, the direction of the resilient force of the spring (1422) exerted against the proximal protrusion (1414) transitions from one of the first and second directions to the other of the first and second directions. The continuous exertion of the resilient force against the proximal protrusion (1414) when the distal tip (1410A, 1410AB) is either the first or second discrete positions, as well as during transitions therebetween, creates a tactile rigid feel to the distal tip (1410A, 1401B) and prevents the distal tip (1410A, 1410B) from having a sloppy or loose feel or otherwise wiggling. In one embodiment, the spring is formed from 301 stainless steel full hard.

FIGS. 32A-39B depict diagrams, and corresponding graphs, showing the direction of forces exerted on the proximal protrusion (1414) of the distal tip (1410A, 1410B) by the spring (1422) at various times of a time period over which the distal tip is transitioned from a straight to an angled orientation and back according to one embodiment. As shown in FIGS. 34A-36B, as the maximum force is applied, the over center point is reached causing the exertion of force to change direction, e.g., from pushing the proximal protrusion (1414) downward to pushing the proximal protrusion (1414) forward, i.e., in the direction of the downward pointing distal tip body (1412).

In one implementation, the spring (1422) is further configured to, when the distal tip (1410A, 14010B) is positioned between the first and second discrete positions, i.e., preceding or following the over center point, rotatably bias the distal tip (1410A, 14010B) toward the closer of the first discrete position or the second discrete position.

Figure 19:
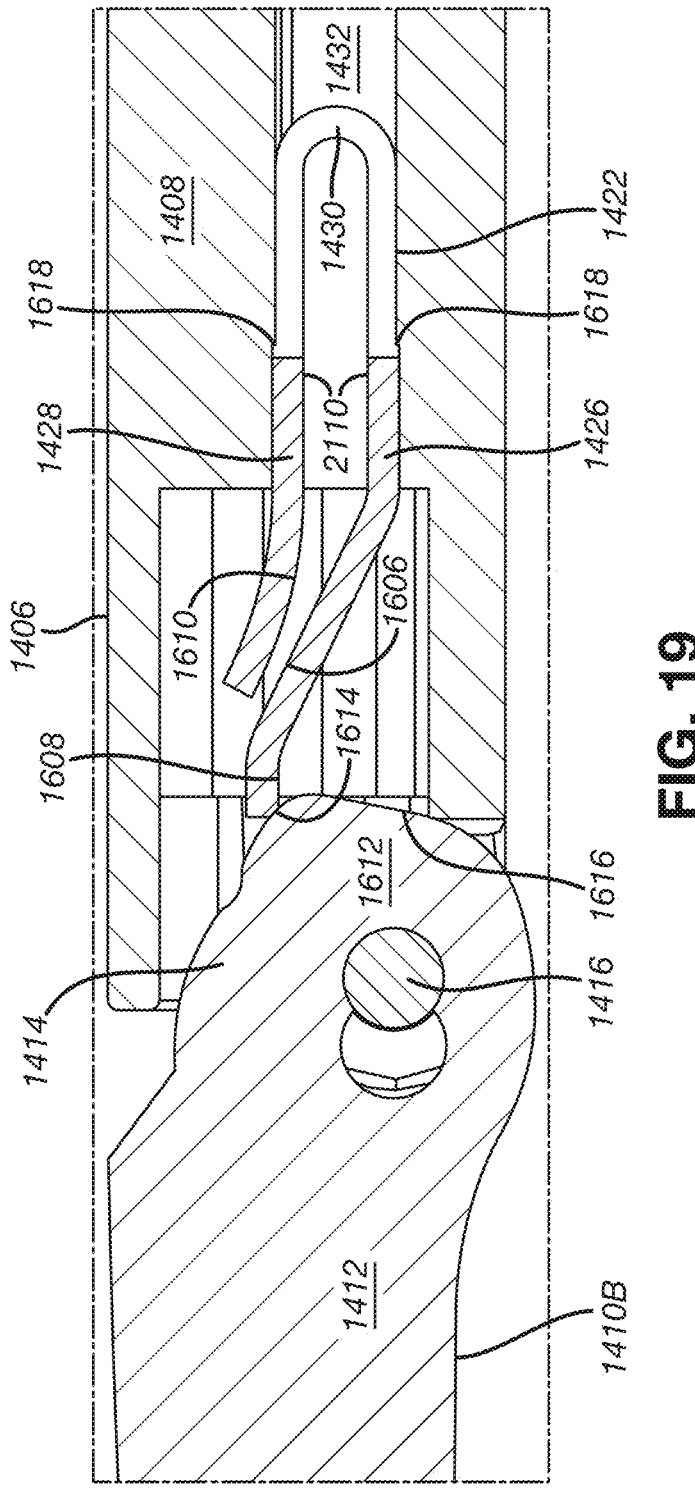
FIG. 19 depicts a distal end the anvil jaw of FIG. 14 with the distal tip shown in a pre-load position according to one embodiment.

As will be appreciated, the disclosed spring (1422) continuously exerts at least some amount of the resilient force against the proximal protrusion (1414), i.e., as shown in FIGS. 19-20B, when assembled to the jaw body (1408), the proximal protrusion (1414) interferes with and deflects the distal end of the spring (1422) such that the spring (1422) is always in a compressed/preloaded state regardless of the distal tip (1410A, 1410B) orientation.

As shown in FIGS. 32A-39B, the spring (1422) and proximal protrusion (1414) form a bistable mechanical system where the spring (1422) is configured to exert the resilient force against the proximal protrusion (1414) in the current direction until the distal tip (1410A, 14010B) is displaced, via the application of an external force to the body (1412) thereof, from its current orientation by a threshold amount, i.e., over center, to change the system state.

It will be appreciated that the exertion of force by the spring (1422) against the proximal protrusion (1414) creates a resistance to the displacement of the distal tip (1410A, 14010B) and defines the threshold amount of external force and the transition of the direction of the resilient force exerted against the proximal protrusion (1414) between the first and second directions may occur abruptly upon the external force exceeding the threshold amount, i.e. going over center, as the bistable mechanical system transitions from one stable position to the other and the first or second portions (1604, 1704A, 1704B, 1704C) of the proximal protrusion (1414) come into contact, impact or are otherwise impeded from further movement by the first or second stops (1602, 1702A, 1702B, 1702C). This may provide a tactile and/or audible response, i.e., where the distal tip (1410A, 1410B) snaps into the particular orientation, causing vibrations which can be felt by the user. Further, this snapping action may create an audible "click" sound, which can be heard by the user. The tactile and/or audible confirmations can be very advantageous in a hospital environment, where the user may be working in darkened or dimly lit rooms, or where the end effector may be visually obscured, e.g., by the patient's anatomy or other instruments, such that the user cannot easily see the distal tip (1410A, 1410B).

As shown in FIGS. 14-21 and 24-28, the spring (1422) comprises at least a first spring arm (1426), also referred to as a plate or leaf, having a proximal portion retained by the jaw body (1408) and a distal portion in contact with the proximal protrusion (1414). In one implementation, the spring (1422) includes two at least partially overlapping spring arms (1426, 1428). In one implementation, the spring (1422) further comprises a proximal portion (1430) which movably/flexibly couples proximal ends of the first and second spring arms (1426, 1428) together. The spring (1422) may be formed by bending and folding one spring arm, i.e., the second or upper spring arm (1428) over the other spring arm, i.e., the first or lower spring arm (1426). Alternatively, the spring (1422) may comprise a leaf spring having at least two stacked leaves, a lower surface of a lower leaf being in contact with the proximal protrusion (1414).

In particular, the first spring arm (1426) comprises an upper surface (1606) and a lower surface (1608), a distal portion of the lower surface (1608) being in contact with the proximal protrusion (1414), the spring (1422) further comprising a second spring arm (1428) having a lower surface (1610), a distal portion of which contacts a distal portion of the upper surface (1606) of the first spring arm (1426) under load, the first and second spring arms (1426, 1428) exerting a combined spring force against the proximal protrusion (1414). It will be appreciated that, via the described overlapping or folded design of the spring (1422), the deflection, and the corresponding spring force, exerted by the spring (1422) is maximized for the available space.

In one implementation, the upper surface (1606) of the first spring arm (1426) is not in contact with the lower surface (1610) of the second spring arm (1428) when not under load. That is, a small gap may be left when the spring (1422) is not under load for manufacturability, i.e., to enable over bending and/or installation. Once pre-loaded, via affixing of the distal tip (1410A, 1410B), as described herein, the pre-loading of the spring (1422) deflects the first spring arm (1426) into contact with the second spring arm (1428) further deflecting the second spring arm (1428).

Figure 27B:
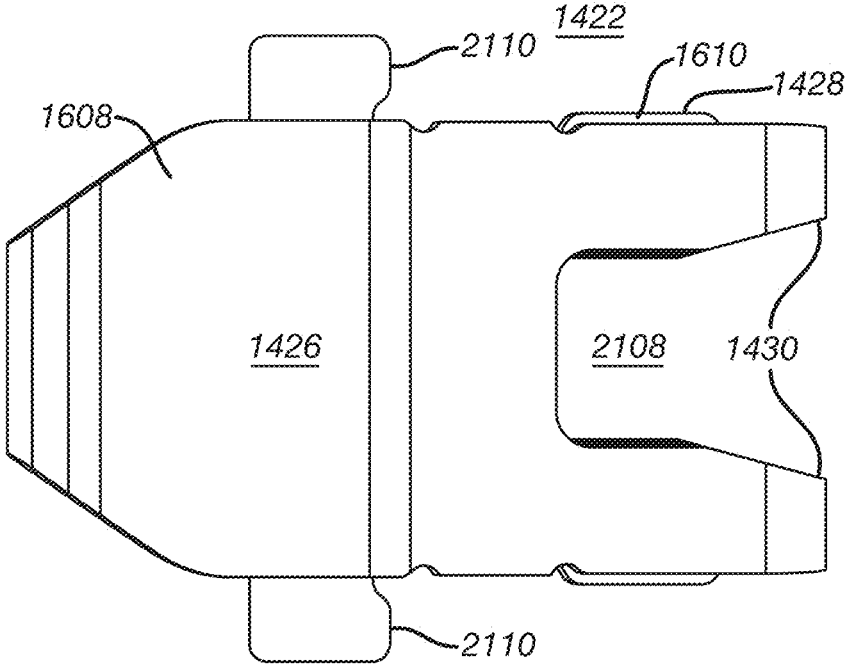
FIG. 27B depicts a bottom view of the spring of FIG. 26 according to one embodiment.
Figures 28A, 28B:
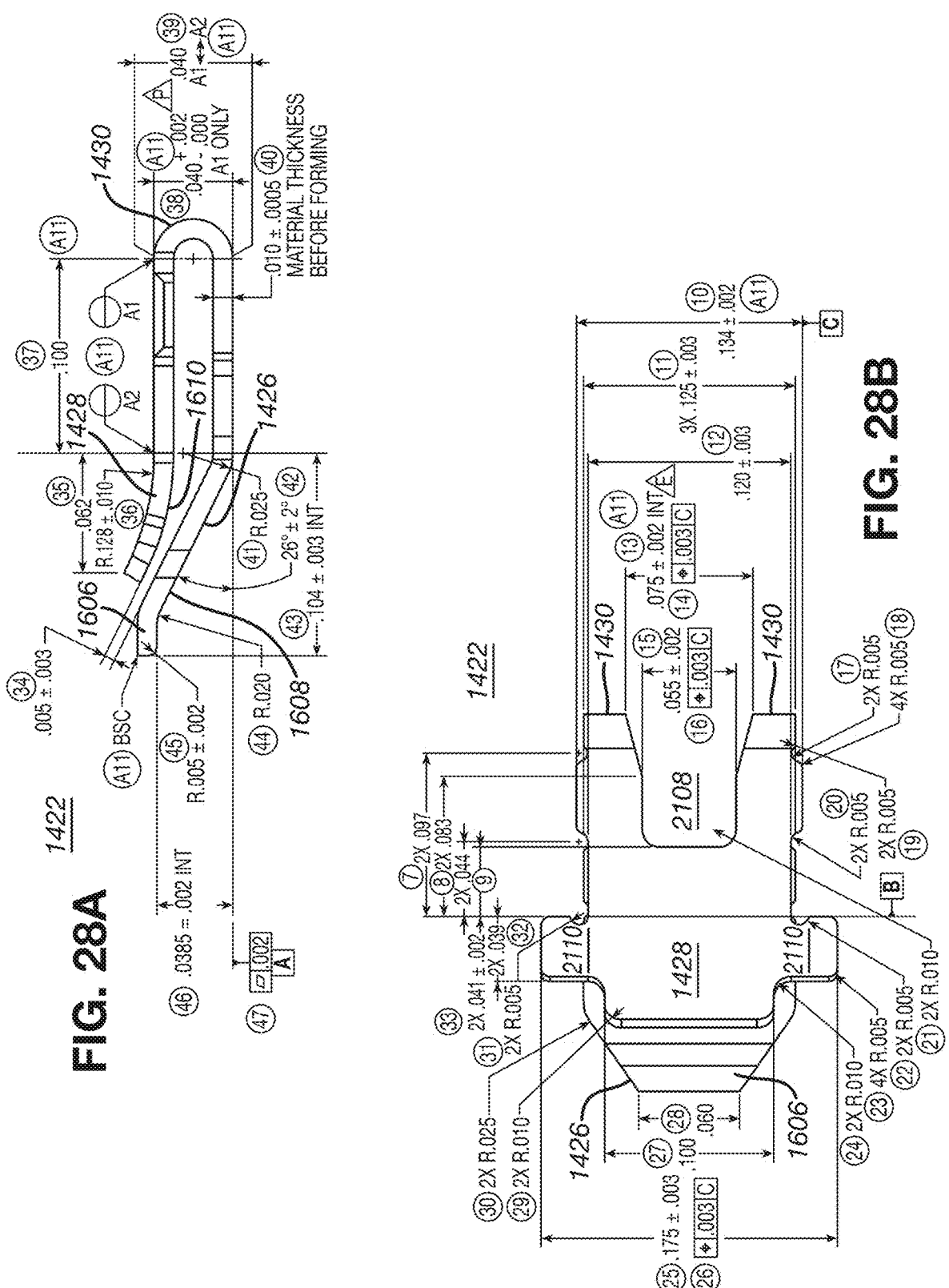
FIGS. 28A and 28B depict side and top views of the spring of FIGS. 26-27B showing example dimensions according to one embodiment.

FIGS. 28A and 28B depict side and top views of the spring (1422) of FIGS. 26-27B showing example dimensions (lengths shown in inches, radii shown in degrees) according to one embodiment. It will be appreciated that the dimensions of the spring (1422) are implementation dependent and may depend on the dimensions of the cam profile (1612), desired range of articulation of the distal tip (1410A, 1410B), desired rigidity or user feel/experience, or other factors as described herein.

As shown in FIGS. 16-17B, 19, 20A, 20B, 22A-25 and 32A-39B, the proximal protrusion (1414) of the distal tip (1410A, 1410B) is characterized by a cam profile (1612), e.g., an irregular shape, which controls the direction in which the spring (1422) exerts the resilient force against the proximal protrusion (1414). That is, as the distal tip body (1412) rotates between the first and second orientations, the proximal protrusion (1414) rotates in the opposite direction against the spring (1422). The cam profile (1612) of the proximal protrusion (1414) defines the direction in which the force is exerted by the spring (1422) against the proximal protrusion (1414) by altering the relative displacement of the proximal protrusion (1414) with respect to the spring (1422), wherein the resilient force of the spring (1422) is exerted opposite and anti-parallel (parallel but moving or oriented in opposite directions) to the displacement of the distal protrusion (1414). Accordingly, the motion of the proximal protrusion (1414) caused by the transition of the distal tip (1710A, 1710B) between the first and second discrete positions causes the direction of the exertion of the resilient force against the proximal protrusion (1414) to change between the first and second directions.

In one implementation, the cam profile (1612) comprises first and second portions (1614, 1616), the first portion (1614) engaging the spring (1422) when the distal tip (1710A, 1710B) is in the first discrete position to cause the exertion of the resilient force against the proximal protrusion (1414) to be in the first direction, and the second portion (1616) engaging the spring (1422) when the distal tip (1710A, 1710B) is in the second discrete position to cause the exertion of the resilient force against the proximal protrusion (1414) to be in the second direction.

In one implementations, the first and second portions (1614, 1616) comprises substantially flat facets arranged at angles on a proximal face of the proximal protrusion (1414) and defining a specific radius from the pivot point (1416) to create different displacements relative to the spring (1422) upon engagement therewith. The facets may meet at a rounded or sharp intermediate portion. In another implementation, the first and second portions (1614, 1616) may be different areas of an elliptical, lobed, oblong or curved proximal face of the proximal protrusion (1414), the specific curvature of each portion (1614, 1616), i.e., the radius therebetween and the pivot (1416) creating different displacements relative to the spring (1422) upon engagement therewith.

Figure 22A:
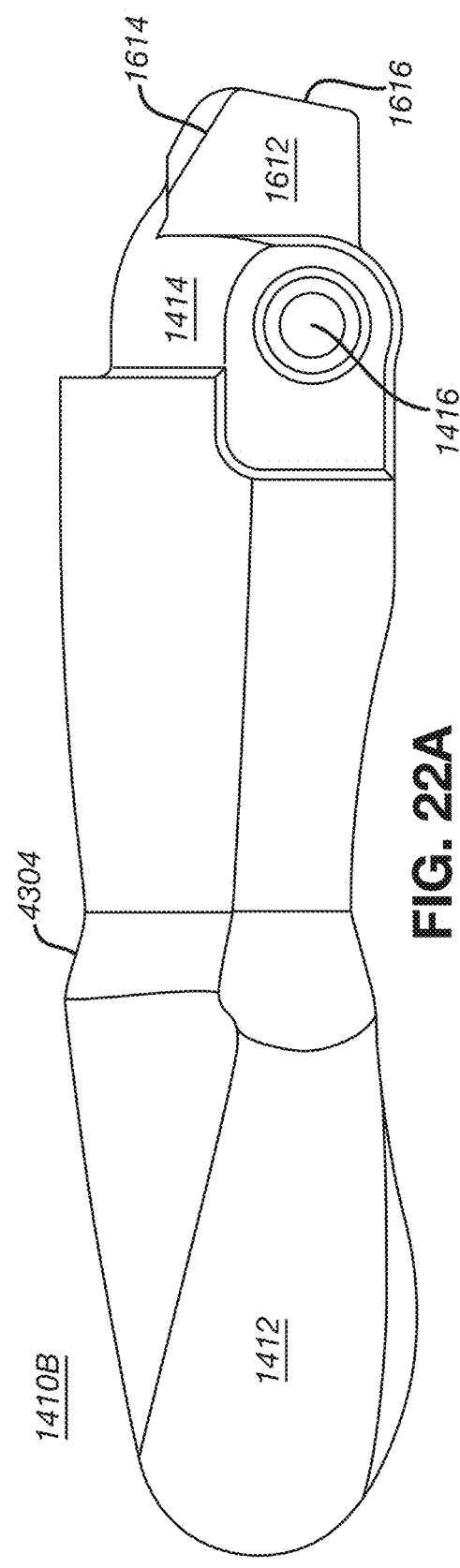
FIG. 22A depicts a side view of a distal tip according to one embodiment.
Figure 22B:
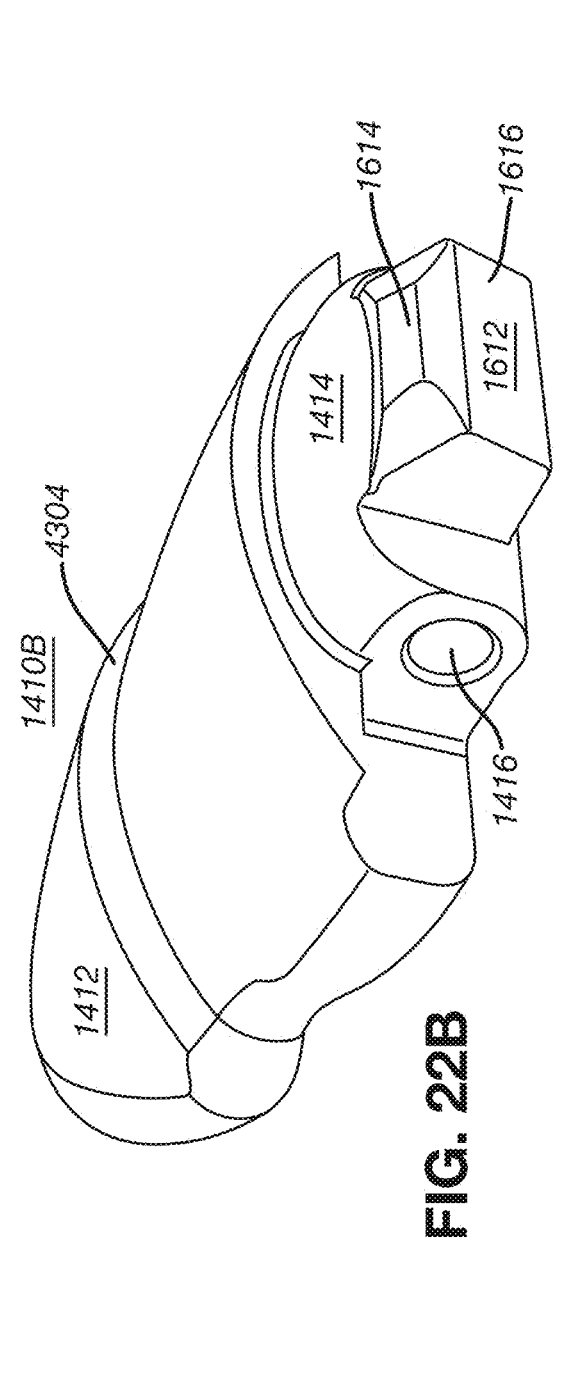
FIG. 22B depicts a rear perspective view of the distal tip of FIG. 22 according to one embodiment.
Figure 23:
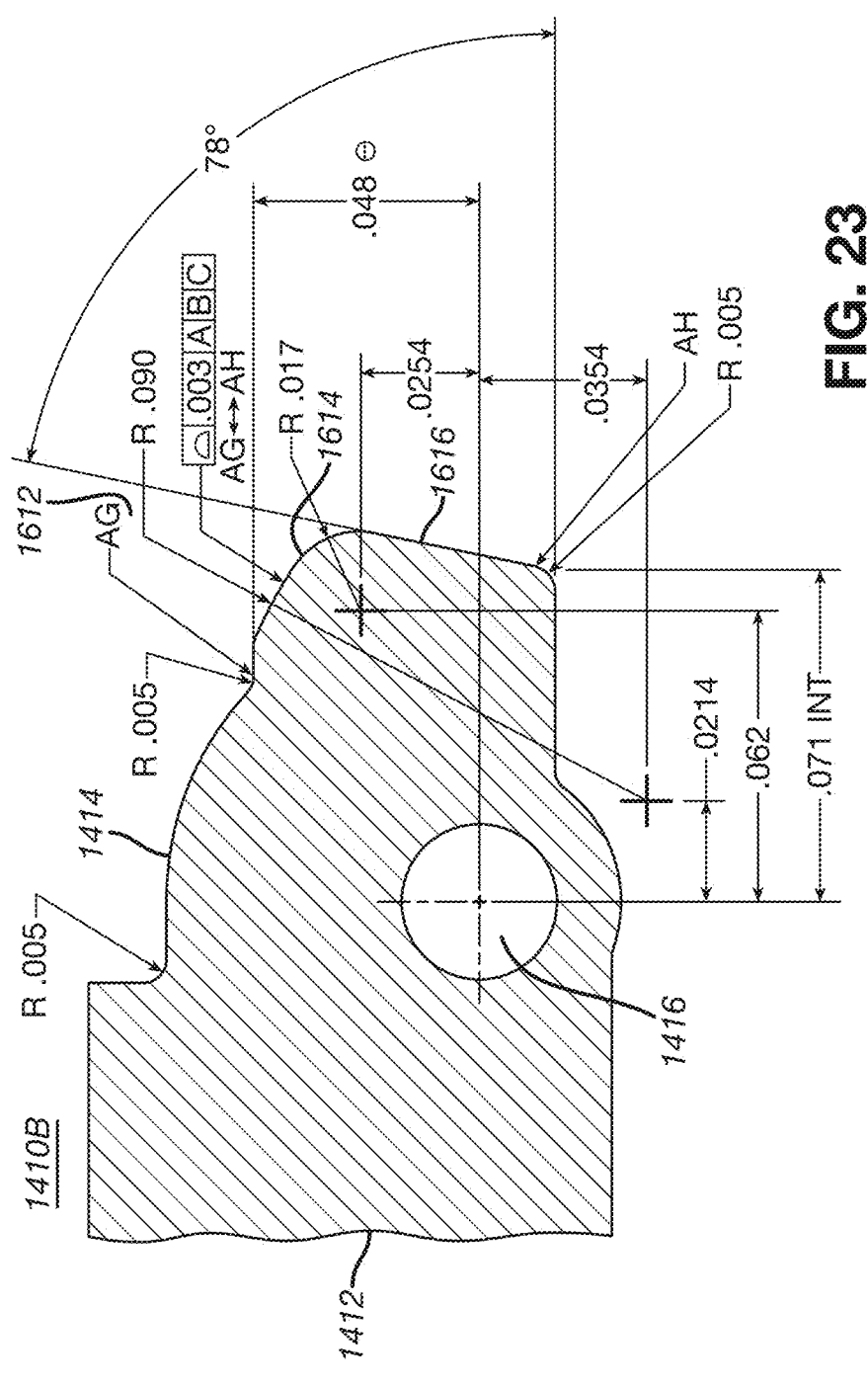
FIG. 23 depicts a cross sectional view of the proximal portion of the distal tip of FIGS. 22A and 22B according to one embodiment.
Figure 24:
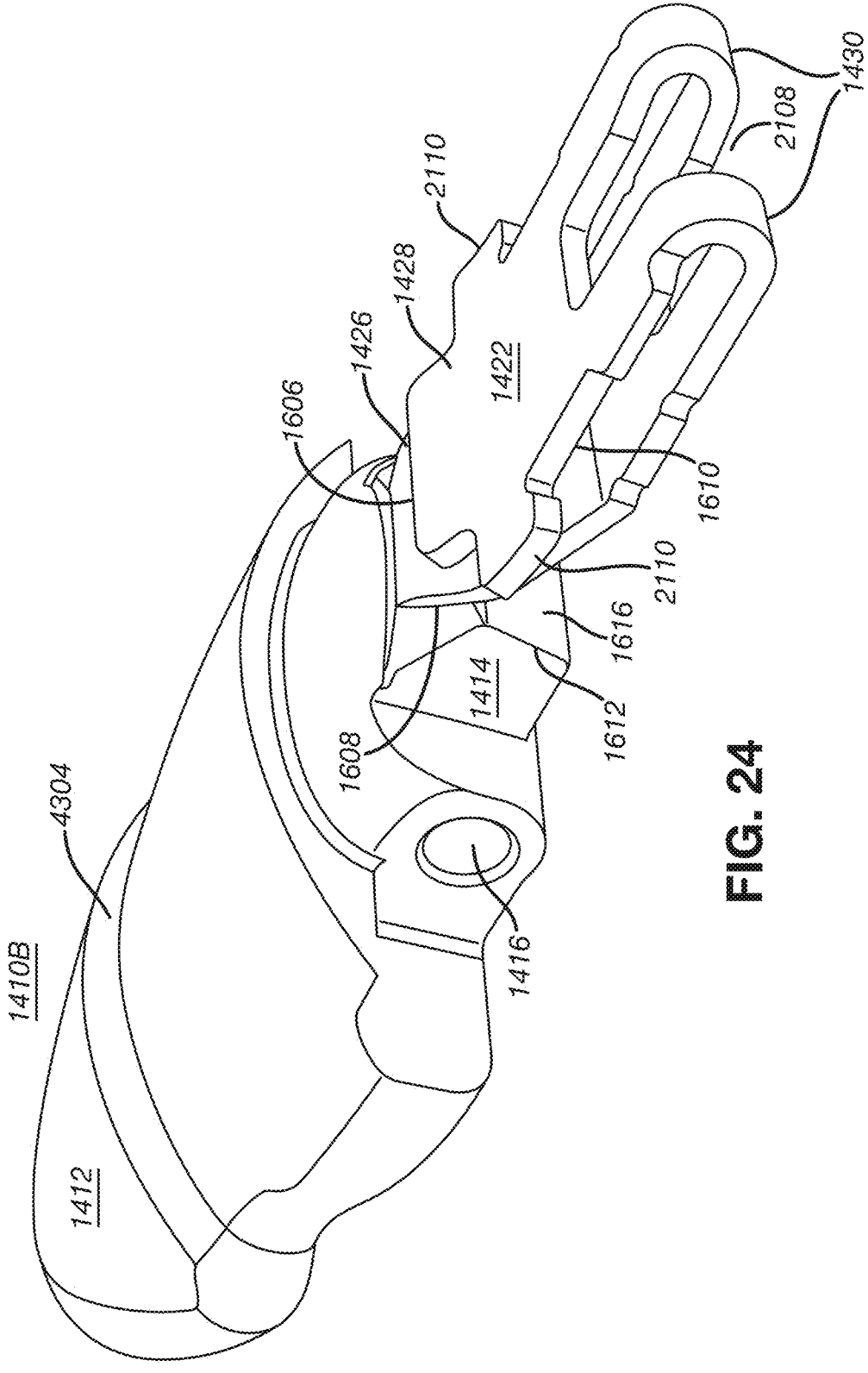
FIG. 24 depicts a rear perspective view of the distal tip of FIG. 22 in a straight orientation relative to a spring according to one embodiment.
Figure 25:
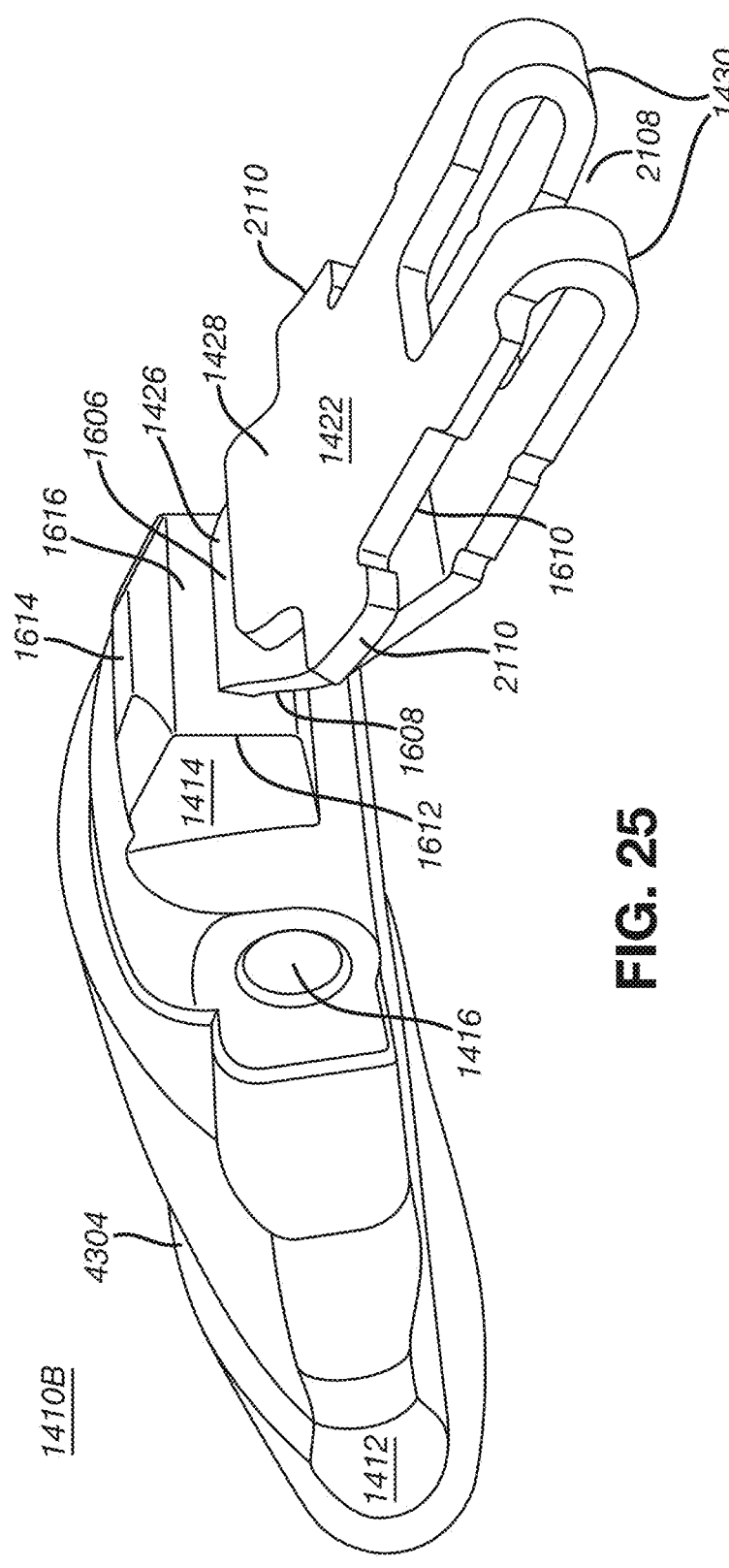
FIG. 25 depicts a rear perspective view of the distal tip of FIG. 22 in an angled orientation relative to a spring according to one embodiment.

FIG. 23 depicts a cross sectional view of the proximal portion of the distal tip of FIGS. 22A and 22B showing example dimensions (lengths shown in inches, radii shown in degrees) of the cam profile (1612). It will be appreciated that the dimensions of the cam profile (1612) are implementation dependent and may depend on the dimensions of the spring (1422), desired range of articulation of the distal tip (1410A, 1410B), desired rigidity or user feel/experience, or other factors as described herein.

As shown in FIGS. 14, 15, 21 and 30 and described elsewhere, the jaw body (1408) further comprises a longitudinal channel (2104) along which at least a portion of a knife (2106) travels from a proximal end to a distal end of the jaw body (1408) so as to transect tissue during operation of the end effector (1402) to cut and staple tissue, the spring (1422) being positioned at the distal end of the jaw body (1408) and comprising a gap (2108) therein so that the travel of the knife (2106) to the distal end is not impeded thereby.

As shown in FIGS. 14-21, 30 and 31, in one implementation, the distal end of the jaw body (1408) includes a cavity (1432) in which the spring (1422) is removably or nonremovably inserted, the spring (1422) including at least one portion (2110), referred to as a wing, which defines the extent of the insertion, i.e., by abutting a stop (1618), also referred to as a stop surface, formed in the jaw cavity (1432). In one implementation, two wings (2110) are formed on opposing sides of the spring (1422) which abut corresponding stops (1618) formed in the jaw cavity (1432).

Figure 13:
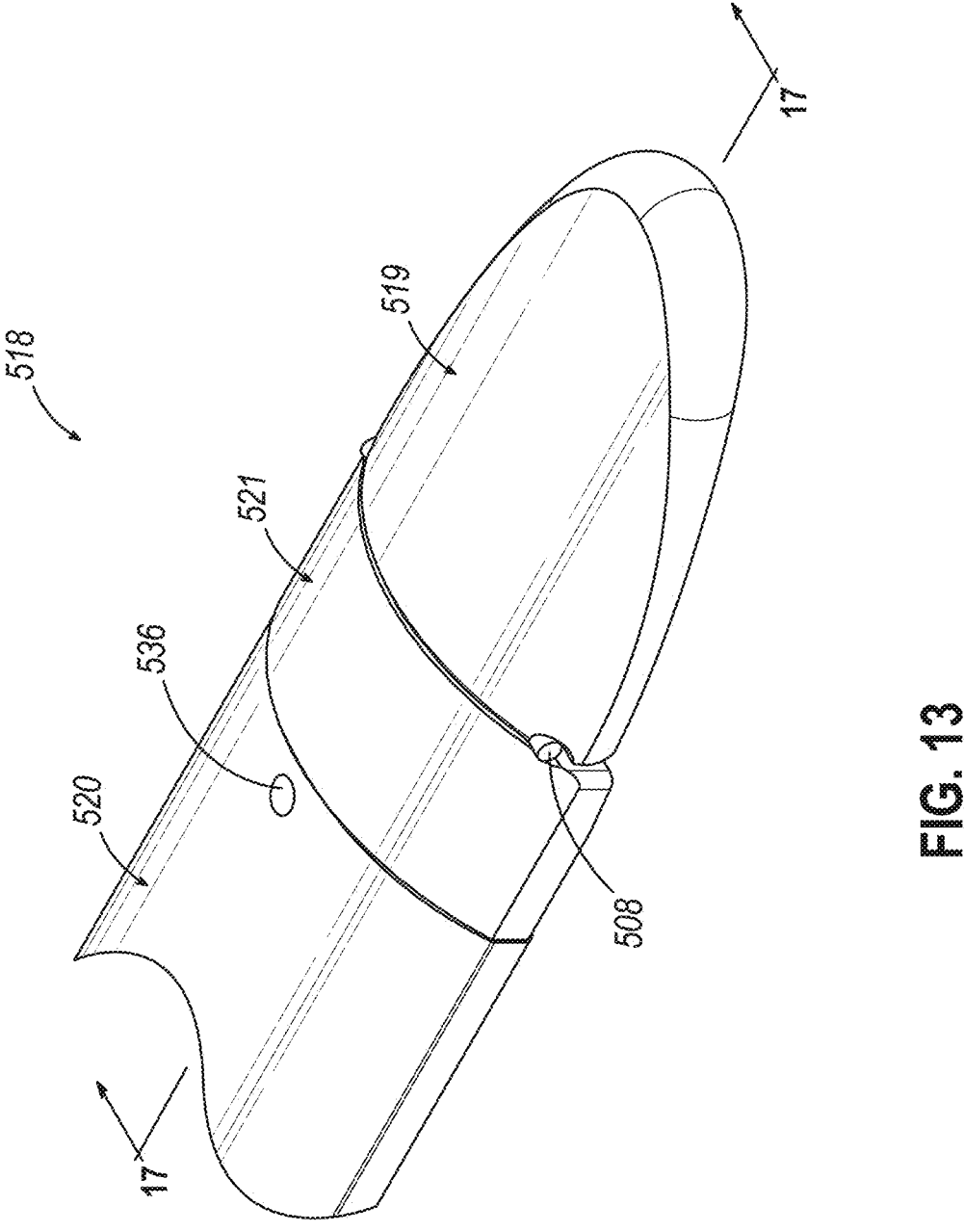
FIG. 13 depicts a perspective view of a distal portion of another anvil jaw configured for use with the surgical instruments described herein.

As shown in FIG. 13, as opposed to affixing the distal tip (1410A, 1410B) to the distal end of the jaw body (1408), an intermediate connector (521) can be used wherein the distal tip (1410A, 1410B) is affixed to the connector (521) as described above and the connector (521) is then affixed to the distal end of the jaw body (1408). In particular, the anvil jaw (518) includes an elongate jaw body (520) having a stapling surface with a plurality of staple forming pockets similar to pockets (53) shown in FIG. 3, a distal tip (519) located distal to jaw body (520), a connector (521) that interconnects distal tip (519) with jaw body (520), and a spring plate (1422) housed within connector (521). As described in greater detail below, the connector (521) is affixed to a distal end of jaw body (520), and the distal tip (519) is pivotably coupled with the connector (521) and is configured to pivot relative to the jaw body (520) between a first discrete position to assume a straight tip orientation, and a second discrete position to assume an angled tip orientation, as described above. In the present version, the connector (521) is configured to be press-fit to the jaw body (520). In particular, the connector (521) includes a proximal protrusion (not shown) that inserts into a slot (not shown) formed in the distal end of the jaw body (520), and this connection is then pinned using a pin (536). Other ways of attaching the connector (521) with the jaw body (520) of the anvil jaw (518) will be apparent to those of ordinary skill in the art. In other versions of the anvil jaw (518), the features of the connector (521) may be integrally formed with the jaw body (520) so as to define an integral connector portion at the distal end of jaw body (520), as noted below.

Connector (521) includes a pair of arms (529) that extend distally. Arms (529) include bores (531) that are configured to align coaxially with a corresponding bore formed in a proximal end portion of distal tip (519) to receive a pivot pin (508) and thereby pivotably couple distal tip (519) with connector (521). In this manner, bores (531) and pivot pin (508) define a longitudinally fixed pivot axis, or axis of rotation, about which distal tip (519) is configured to pivot (or "toggle") between the first and second discrete positions, and which extends transversely relative to a longitudinal axis of jaw body (520). In some alternative versions, the pivot axis may be permitted to slidably translate longitudinally by a minimal distance before, during, or after pivotal motion about the pivot axis, for example by providing bores (531) of connector (521) or the bore of distal tip (519) with an elongate cross-sectional shape rather than a circular cross-sectional shape. Pivot pin (508) may be press fit, threaded, or glued, for example, to either connector (521) or distal tip (519) and, in some versions, may be removable. Connector (521) further includes a longitudinally extending slot (527) (which may also be referred to as a cavity) that houses and restrains the spring (1422) as was described above.

In one implementation, as shown in FIGS. 19, 20A and 20B, the jaw (1406) of the end effector (1402) may be manufactured by inserting a spring (1422) into a cavity (1432) formed in a distal end of the jaw body (1408); and affixing, pivotably, a distal tip (1410A, 1410B) to the distal end of the jaw body (1408), the distal tip (1410A, 1410B) comprising a protrusion (1414) proximal to a pivot axis (1416) which abuts, interferes with and preloads the spring (1422) upon affixation of the distal tip (1410A, 1410B) to the distal end of the jaw body (1408), the spring (1422) thereafter exerting a resilient force against the proximal protrusion (1414) in a first direction so as to releasably bias a first portion (1604) of the distal tip (1410A, 1410B) against a first stop (1602) formed in the jaw body (1408) when in a first discrete position and exert the resilient force against the proximal protrusion (1414) in a second direction, different from the first direction, so as to releasably bias a second portion (1704A, 1704B, 1704C) against a second stop (1702A, 1702B, 1702C) formed in the jaw body (1408), different from the first stop (1602), when in a second discrete position. In one implementation, the proximal protrusion (1414) is configured to interfere with the distal portion of the spring (1422) by 0.10 inches when assembled.

In one implementation, the manufacturing of the jaw (1406) may further include forming, prior to the inserting, the spring (1422) by folding a first spring arm (1426) over a second spring arm (1428) such that the first spring arm (1426) overlaps the second spring arm (1428), wherein upon the affixing, a portion of a lower surface (1608) of the first spring arm (1426) is in contact with the proximal protrusion (1414), and a portion of a lower surface (1610) of the second spring arm (1428) contacts a portion of an upper surface (1606) of the first spring arm (1426), the first and second spring arms (1426, 1428) exerting a combined spring force against the proximal protrusion (1414).

In one implementation, the manufacturing of the jaw (1406) may further include forming, prior to the affixing, a cam profile (1612) on the proximal protrusion (1414) of the distal tip (1410A, 1410B) which controls the direction in which the spring (1422) exerts the resilient force against the proximal protrusion (1414).

B. Anvil Jaw Having a Covered Tip

As noted above, the pivot axis (1416) of the above described distal tip (1410A, 1410B) may comprise a pivot or hinge structure or clevis/shackle, e.g., a U-shaped or forked connector formed in either the distal end of the anvil jaw (1406) body (1408) or proximal portion of the distal tip (1410A, 1410B) within which the distal tip (1410A, 1410B) can be fastened by means of a pin passing through the ends of the connector, wherein the distal end of the jaw body (1408) and an intermediate portion of the distal tip (1410A, 1410B) between the body (1412) and proximal protrusion (1414) each include bore holes (1416) which are coaxially aligned when the distal tip (1410A, 1410B) is assembled to the jaw body (1408) and through which a pin is inserted to pivotably affix the distal tip (1410A, 1410B) thereto. For example, the distal end of the jaw body (1408) includes a pair of arms that extend distally. The arms include bores that are configured to align coaxially with a corresponding bore formed in a proximal end portion of distal tip (1410A, 1410B) to receive a pivot pin and thereby pivotably coupling (1416) the distal tip (1410A, 1410B) with the jaw body (1408).

Figure 40A:
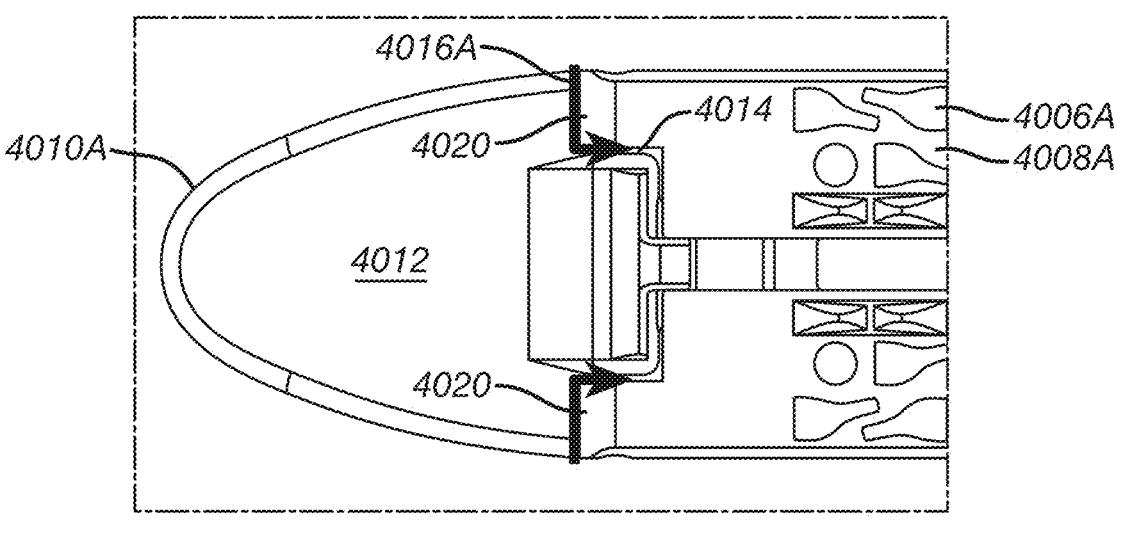
FIG. 40A depicts a bottom view of a distal end of an end effector having a distal tip affixed thereto according to one implementation.
Figure 40B:
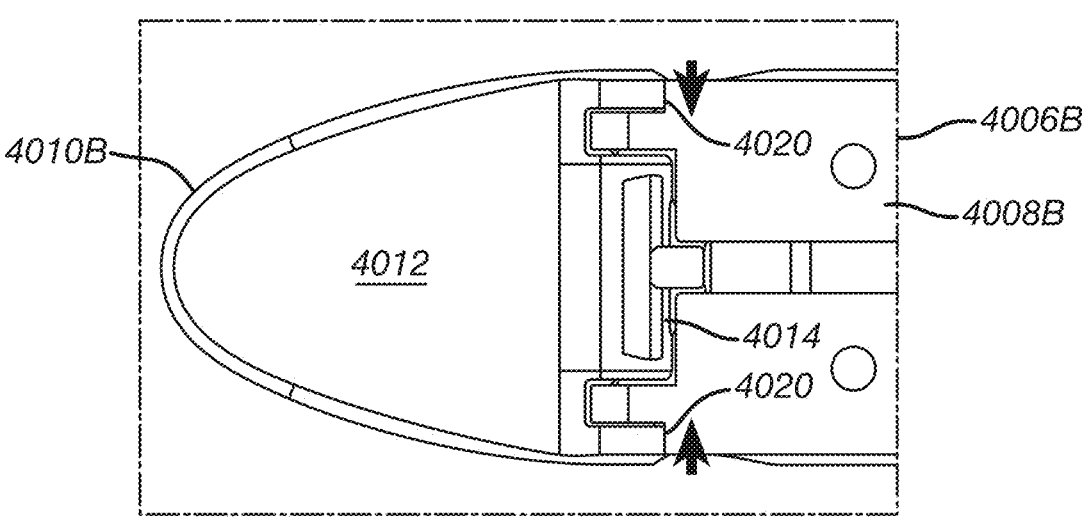
FIG. 40B depicts a bottom view of an distal end of an end effector having a distal tip affixed thereto according to another implementation.
Figure 41:
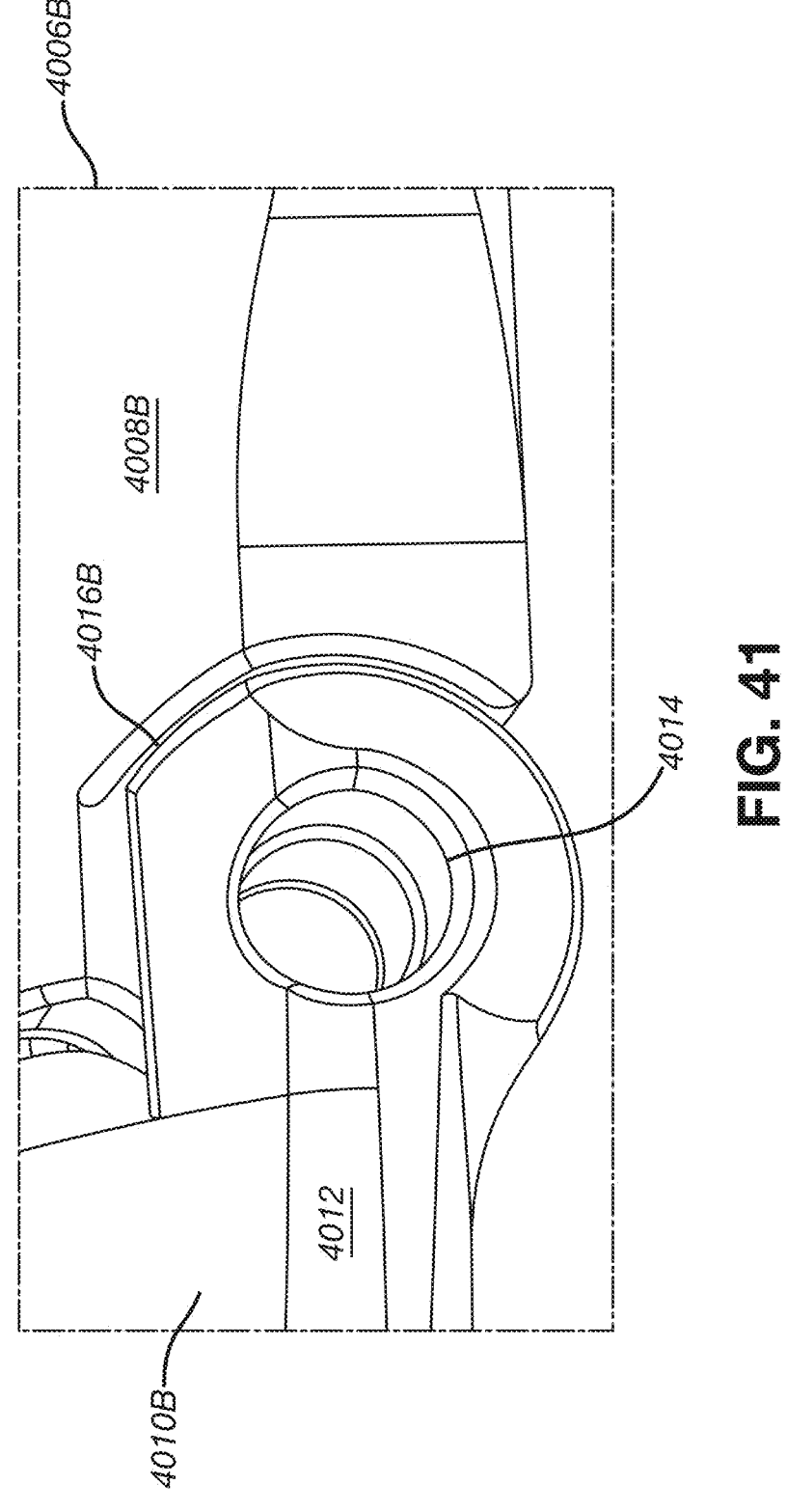
FIG. 41 depicts close up perspective side view of a pivot joint of the end effector of FIG. 40A.

FIGS. 40A-41 show examples of distal tips (4010A, 4010B) similar to distal tips (1410A, 1410B) discussed above, having tip bodies (4012) and assembled to jaw bodies (4008A, 4008B) of anvil jaws (4006A, 4006B) similar to those discussed above, having staple forming cavities, etc., in a similar pivotable manner as described above. Where the distal tip (4010A, 4010B) pivotably meets and is affixed to the distal end of the jaw body (4008A, 4008B) via pin and coaxial bore holes (4016) as described, it will be appreciated that a gap (4016A, 4016B), also referred to as a space or separation, occurs or is otherwise formed therebetween, i.e., at the interface thereof. This gap (4016A, 4016B) may be such that the affixed portions actually touch and rub against one another during movement or may be wider such that the affixed portions do not touch. The gap (4016A, 4016B) may include both portions transverse to the jaw body axis and parallel thereto depending upon the structure/architecture/ arrangement of the hinge/pivot mechanism, e.g., arms and other coaxially aligned portions, used to affix the distal tip (4010A, 4010B) to the jaw body (4008A, 4008B). In particular, at least a portion of the gap (4016A, 4016B) may extend to the outer edges of the jaw body (4008A, 4008B) or otherwise be exposed to tissue when the end effector is inserted into a patient.

Where such gaps (4016A, 4016B) are exposed to tissue as the end effector 4002 is navigated through tissue and/or operated as described herein, it is possible for tissue to intrude in and get caught, pinched or otherwise snagged, by at least a portion of the gap (4016A, 4016B).

FIG. 40B shows one solution to prevent such tissue intrusion, i.e., to minimize the length of the gap, i.e., the transverse portion thereof open to the sides of the jaw body 4008B. This is accomplished by implementing a pivot/hinge (4014) which interleaves arms extending distally from the jaw body (4008B) with arms extending proximally from the distal tip body (4012). However, even a shorter length gap (4016B) has the potential to catch tissue.

Figure 42:
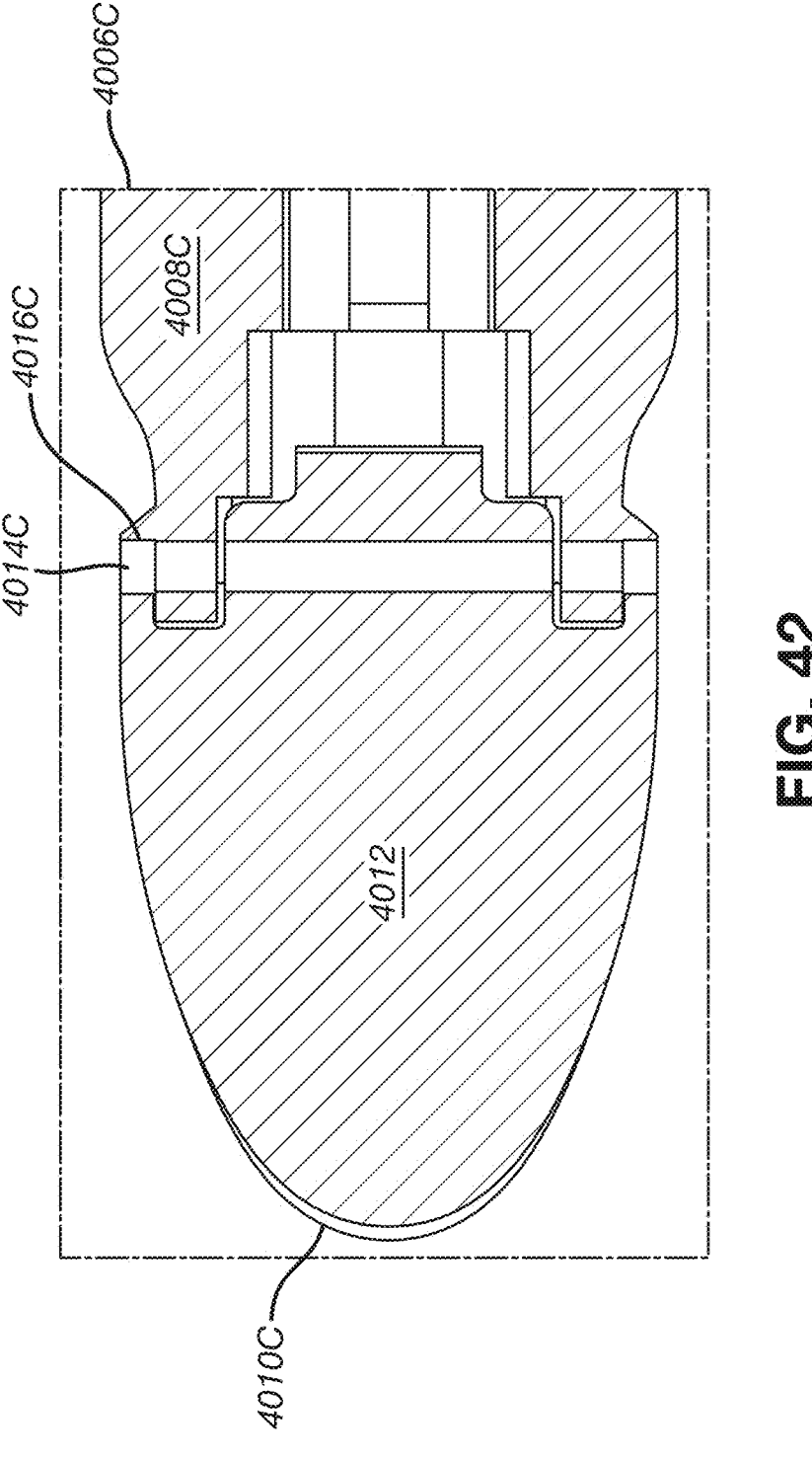
FIG. 42 depicts a bottom view of a distal end of an end effector having a distal tip affixed thereto according to another implementation.

FIG. 42 shows another solution to prevent such tissue intrusion, i.e., to minimize the size of the gap (4016C) by creating an interference fit, also referred to as a friction or pressed fit, e.g., a fit between two parts in which the external dimension of one part slightly exceeds the internal dimension of the part into which it has to fit, between the distal tip (4010C) and the distal end of the jaw body (4008C) such that tissue may be prevented from ingress into the gap (4016C) and getting caught. It will be appreciated however, that any affixation that eliminates tissue ingress by reducing the size of the gap (4016C) may also interfere with movement of the distal tip (4010C) as described herein.

Accordingly, FIGS. 43A-50 show alternative implementations for preventing tissue ingress and snagging and which can be used with the articulating distal tips described above or with other end effectors having articulating distal tips where similar gaps may be present.

Referring to FIGS. 43A-50, there is shown an apparatus, i.e., a portion of an end effector 1402 comprising a first jaw (1404), e.g., a cartridge jaw, and a second jaw (1406), e.g., an anvil jaw, configured to cooperate with the first jaw (1404) to clamp and staple tissue with a plurality of staples. The second jaw (1406) includes a jaw body (1408) extending longitudinally along a jaw body axis (1418) and a distal tip (1410B) movably disposed distal to the jaw body (1408) and extending longitudinally along a distal tip axis (1420). The distal tip (1401B) is pivotable about a pivot axis (1416) which extends transversely to the jaw body axis (1418), the distal tip (1410B) being pivotable between at least a first discrete position and a second discrete position different from the first discrete position, wherein in the first discrete position the distal tip axis (1420) assumes a first orientation relative to the jaw body axis (1418), and in the second discrete position the distal tip axis (1420) assumes a second orientation relative to the jaw body axis (1418) different from the first orientation, wherein the distal tip (1410B) includes a body (1412) which extends distal to the pivot axis (1416).

The second jaw (1406) further includes a joint (4014) which pivotably connects a proximal portion of the distal tip (1410B), or otherwise enables articulation thereof, to a distal end of the jaw body (1408), as described elsewhere herein, and defines the pivot axis (1416), the joint characterized by a gap (4016A), into which tissue may ingress, between at least a portion the proximal portion of the distal tip (1410B) and at least a portion of the distal end of the jaw body (1408), the gap (4016A) having at least portion (4018) which is aligned with the jaw body axis (1408). As discussed above, the gap (4016A) is formed by, or occurs as a consequence of, the hinge/pivot mechanisms described above. In one implementation, the gap (4016A) comprises a further portion (4020) which is transverse to the jaw body axis (1408), which may be defined by the width of the proximal portion of the tip body (1412) vs the width of the jaw body (1408).

The second jaw (1406) further includes a cover (4302) which at least obstructs the gap (4016A) to prevent or otherwise minimize tissue ingress/intrusion therein regardless of the position of the distal tip (1410B). That is, in one implementation, at a time of manufacture of the end effector (1402) or thereafter, the gap (4016A) may be obstructed with the cover (4302).

Figure 43A:
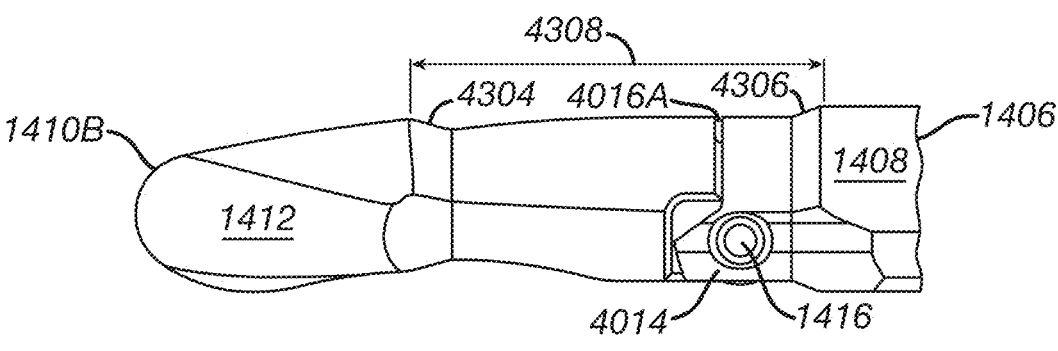
FIG. 43A depicts a side view of a distal end of an anvil jaw according one embodiment.
Figure 43B:
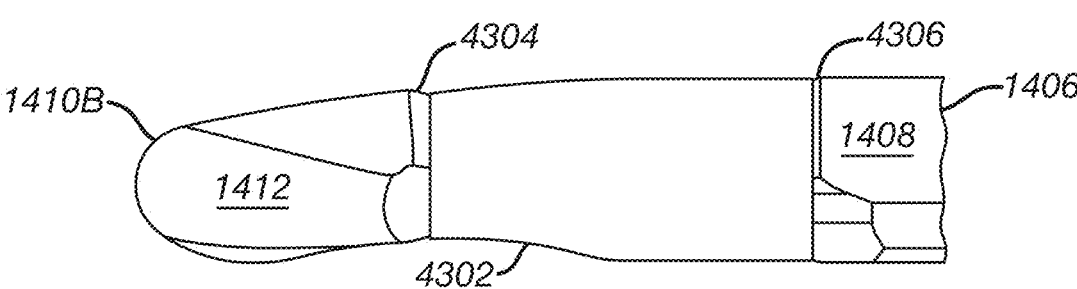
FIG. 43B depicts a side view of the distal end of the anvil jaw of FIG. 43A with a cover and distal tip in a straight orientation according one embodiment.
Figure 43C:
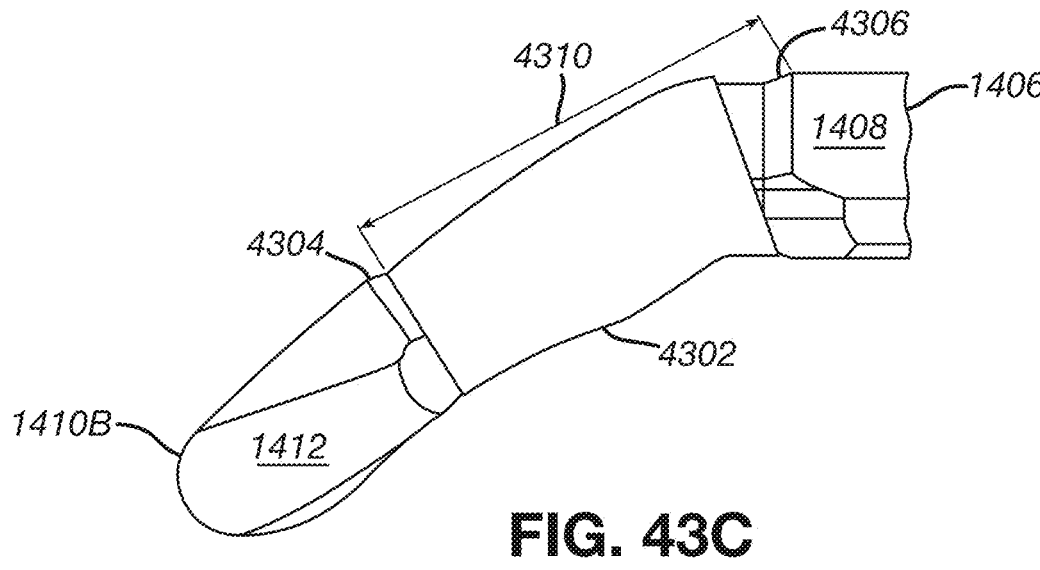
FIG. 43C depicts a side view of the distal end of the anvil jaw of FIG. 43A with a cover and distal tip in an angled orientation according one embodiment.

In one implementation, the cover (4302) is configured to resist displacement during movement/articulation of the distal tip (14010B), as shown in FIGS. 43B and 43C, between the first and second orientations.

In one implementation, the cover (4302) covers the joint (4014).

In one implementation, as shown in FIGS. 43B-44C, the cover (4302) extends distally to cover a proximal portion of the distal tip body (1412) and proximally to cover a distal portion of the jaw body (1408). In one implementation, the cover (4302) comprises a heat shrinkable material wrapped or otherwise applied, at a time of manufacture of the end effector (1402) or thereafter, around the proximal portion of the distal tip body (1412) and distal portion of the jaw body (1408). In one implementation, the cover (4302) is made of Altera Medical-Grade, USP Class VI, High Shrink Ratio, Polyolefin Tubing, manufactured by RayChem™ Tubing Products, a division of TE Connectivity LTD., located in Berwyn, PA. It will be appreciated that any suitably flexible/elastic material which may be rolled on, sprayed on, wrapped, or otherwise applied to cover the joint (4014) may be used, including rubber, silicone or other bio-compatible, non-reactive, sterilization compatible, or otherwise tear resistant material. In one implementation, the cover (4302) may be affixed and, subsequently, any excess material may be trimmed or otherwise removed, e.g., via mechanical or laser cutter, etc., so as to fit within the recesses (4304, 4306) as described below.

In one implementation, as shown in FIGS. 22-25 and 43A, the proximal portion of the distal tip body (1412) includes a recess formed by a chamfer (4304) in which the cover (4302) is affixed, at a time of manufacture of the end effector (1402) or thereafter, or otherwise sits, e.g., a distal portion thereof, i.e., in the case of a heat shrinkable material, once heat has been applied to shrink the cover.

Figures 29A, 29B:
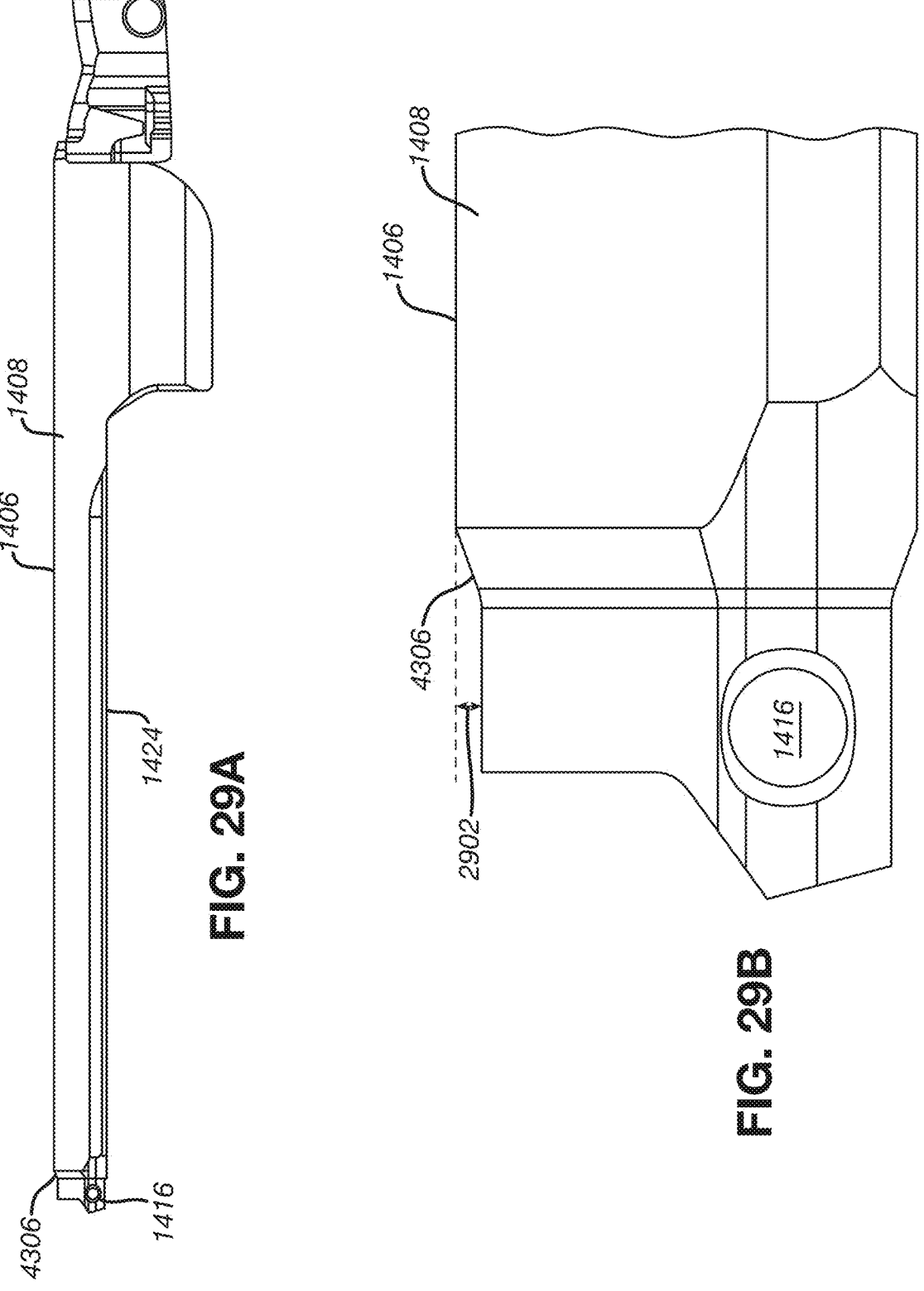
FIG. 29A depicts an anvil jaw according to one embodiment.
FIG. 29B depicts a distal end of the anvil jaw of FIG. 29A according to one embodiment.
Figure 30:
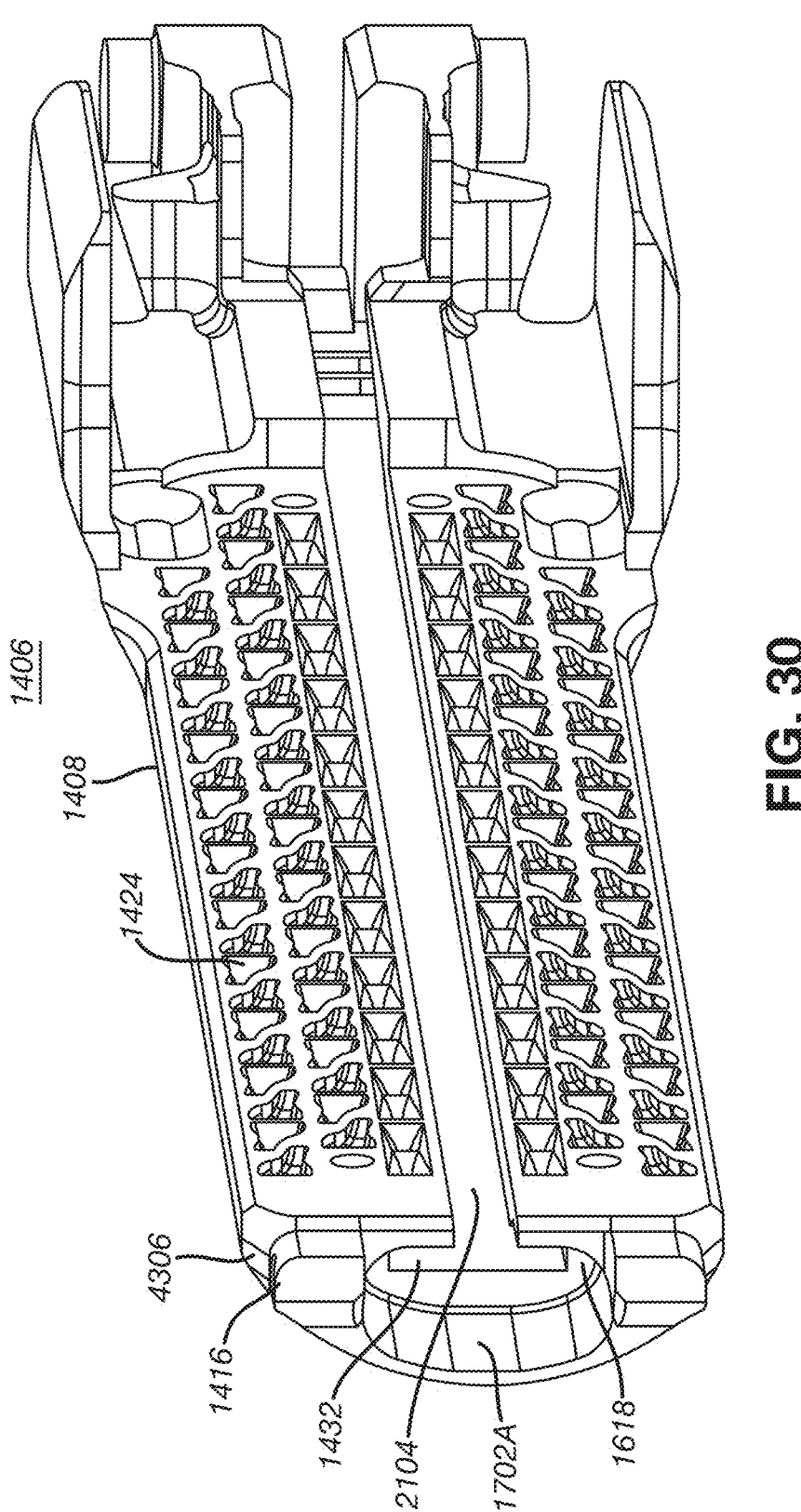
FIG. 30 depicts a bottom perspective view of the anvil jaw of FIG. 29A according to one embodiment.
Figure 31:
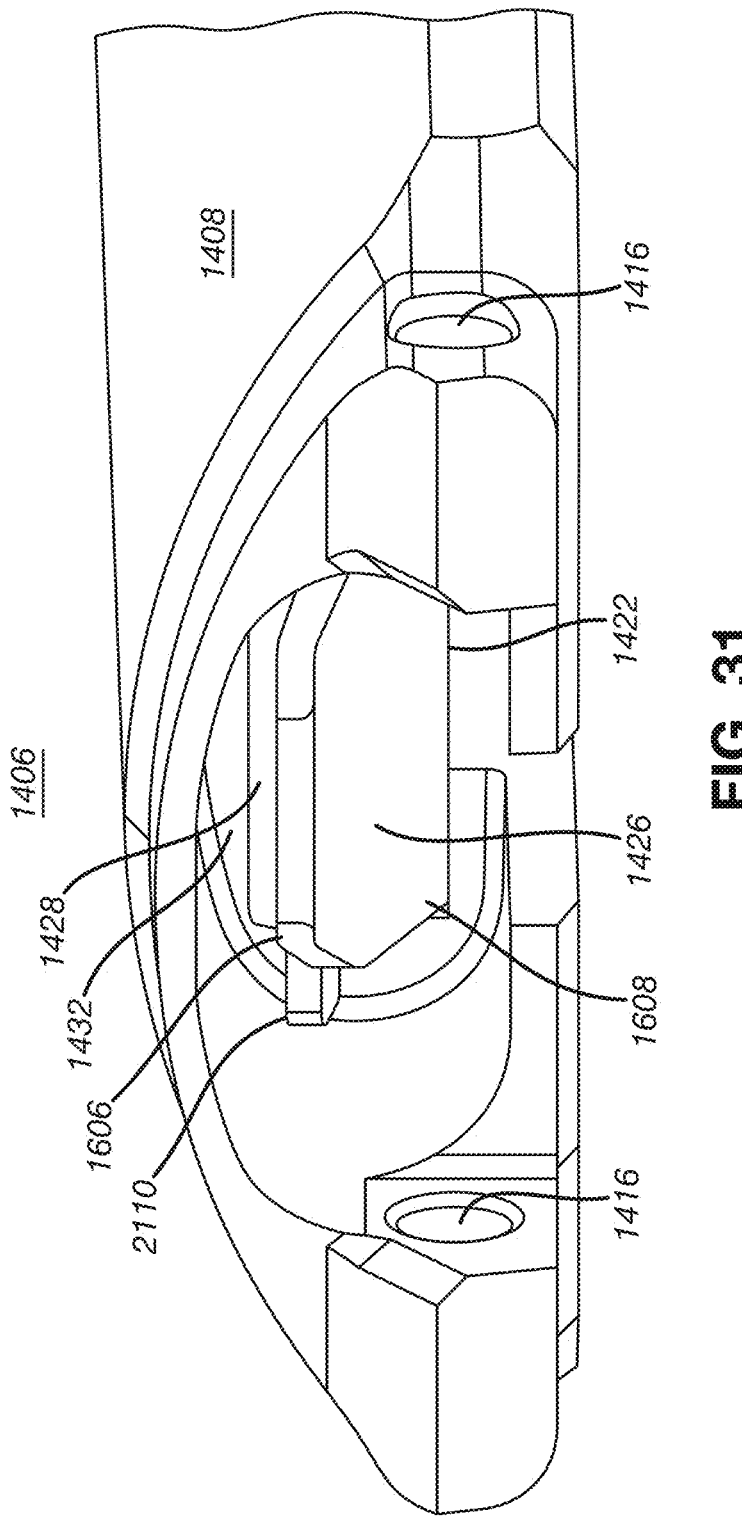
FIG. 31 depicts a front perspective view of the distal end of the anvil jaw of FIG. 29A according to one embodiment.

Further, as shown in FIGS. 29A, 29B and 43A, in one implementation, while the distal portion of the cover (4302) sits in the recess (4304) of the distal tip body (1412), the jaw body (1408) further includes a recess formed by a chamfer (4306) in which a proximal portion of the cover (4302) sits, the distal tip body and jaw body recesses (4304, 4306) configured to constrain the cover (4302), as well as reduce edges of the ends of the cover (4302), i.e., such that the cover (4302) is flush with the non-recessed portion of the distal tip (1410B) and jaw body (1408). In this implementation, the chamfers (4304, 4306) cooperate to form a recess which extends both proximally and distally beyond the joint (4014) and which receives the cover 4302 such that the cover (4302) extends both proximally and distally beyond the joint (4014) to ensure coverage during transitions between and when the distal tip (1410B) is in the first or second orientations. In one implementation, the minimum projected clearance, or depth of the chamfers (4304, 4306), (2902) may be 0.0070 inches at 20 degrees. It will be appreciated that the tip chamfer (4304) is across a more variable cross section. In one implementation, the length of the recess (4308) may be 0.2719 inches when the tip (1410B) is in the first/straight orientation and the length of the recess (4310) may be 0.3217 inches when the top (1410B) is in the second/angled orientation.

Figure 49:
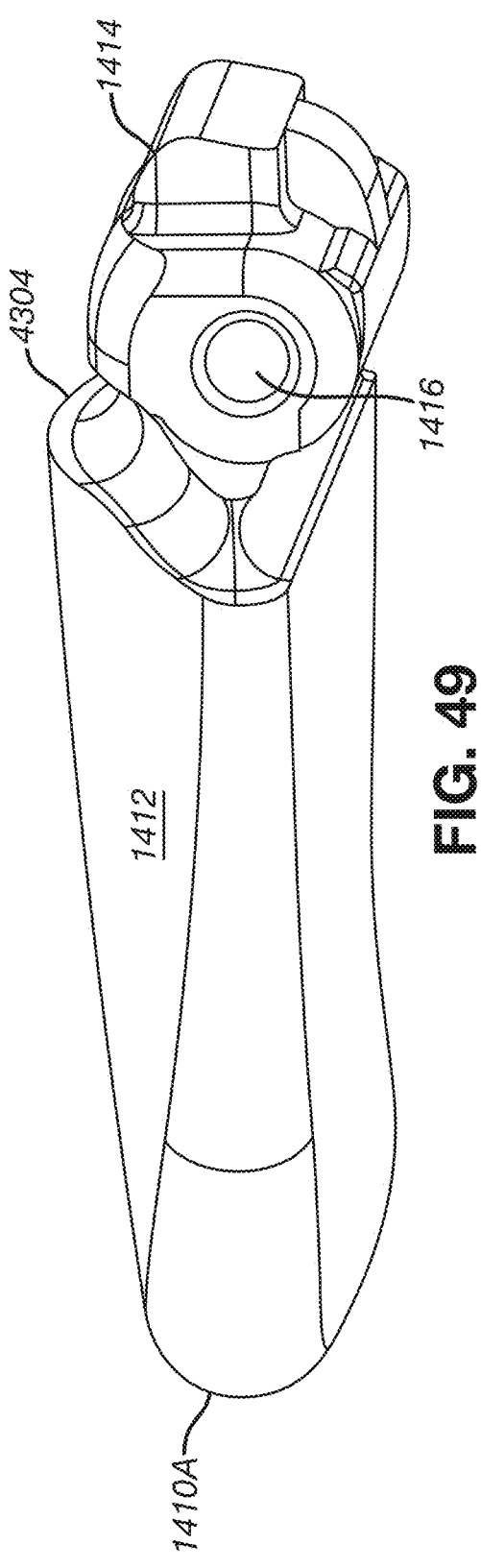
FIG. 49 depicts a side perspective view of a distal tip according to one embodiment.

In an alternative implementation, as shown in FIG. 45-49, the cover (4302) comprises an elastic loop (4502) which is fitted in the recess (4304), shown in FIG. 49. In one implementation, the elastic loop (4502) comprises an o-ring, band or gasket, formed from a suitably flexible/elastic material which may be rolled on, sprayed on, wrapped, or otherwise applied to cover the joint (4014) may be used, including rubber, silicone or other bio-compatible, non-reactive, sterilization compatible, or otherwise tear resistant material. In one implementation, the elastic loop (4502) comprises a medical grade liquid silicone rubber.

Figure 50:
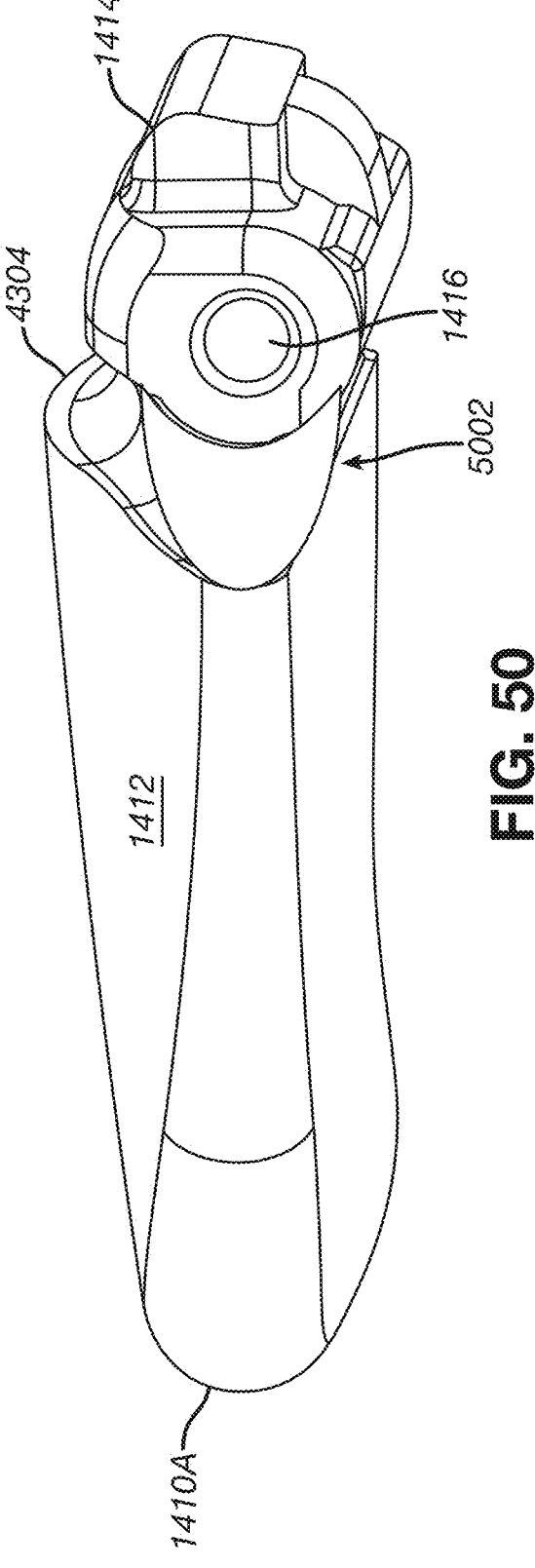
FIG. 50 depicts a side perspective view of a distal tip according to another embodiment.

In another alternative implementation, as shown in FIG. 50, the cover (4302) comprises elastic material (5002) formed on a proximal portion of the distal tip body (1412), i.e., at a time of manufacture of the distal tip (1410A, 1410B) or thereafter, so as to create an interference fit between the distal tip (1410A, 1410B) such that elastic material compresses against the distal end of the jaw body (1408) when the distal tip (1410A) is assembled to the jaw body (1408).

In one implementation, the disclosed end effector (1402) may be manufactured by joining, pivotally, a proximal portion of a distal tip (1410B) to a distal end of the jaw body (1408) such that the distal tip (1410B) is pivotable between at least a first discrete position and a second discrete position different from the first discrete position, wherein in the first discrete position a distal tip axis (1420) assumes a first orientation relative to a jaw body axis (1418), and in the second discrete position the distal tip axis (1420) assumes a second orientation relative to the jaw body axis (1418) different from the first orientation, wherein the joining forms a gap (4016A) between at least a portion the proximal portion of the distal tip (1410B) and at least a portion of the distal end of the jaw body (1408), the gap (4016A) having at least portion (4018) which is aligned with a jaw body axis (1418) of the jaw body (1408); and obstructing the gap (4016A) with a cover (4302) to prevent tissue ingress therein regardless of the position of the distal tip (1410B). The joining may occur at a joint (4014), the method further comprising covering the joint (4014) with the cover (4302). The method may further include extending the cover (4302) distally to cover a proximal portion of the distal tip (1410B) and proximally to cover a distal portion of the jaw body (1408). Where the cover (4302) comprises a heat shrinkable material, the manufacture may further include wrapping or otherwise applying the heat shrinkable material around the proximal portion of the distal tip (1410B) and distal portion of the jaw body (1408) and applying heat thereto, with any excess material being trimmed before and/or after the application of heat. In one implementation, the manufacturing may include forming, at least prior to the obstructing, a recess/chamfer (4304) in the proximal portion of the distal tip (1410B) configured to receive the cover (4302). Where the cover (4302) comprises an elastic loop (4502), the manufacture may include fitting the elastic loop (4502) in the recess (4304). Where the recess (4304) formed in the distal tip (1410B) is configured to receive a distal portion of the cover (4302), the manufacturing may further include forming, at least prior to the obstructing, another recess/chamfer (4306) in the jaw body (1408) configured to receive a proximal portion of the cover (4308), the distal tip and jaw body recesses/chamfers (4304, 4306) configured to create a recess along a length of the distal tip (1410B) and jaw body (1408) to constrain the cover (4302) as well as reduce exposed edges and/or ensure the cover (4302) is flush with non-recessed portion of the distal tip (14010A, 1401B)/jaw body (1408).

VI. Examples of Combinations

The following examples relate to various non-exhaustive ways in which the teachings herein may be combined or applied. It should be understood that the following examples are not intended to restrict the coverage of any claims that may be presented at any time in this application or in subsequent filings of this application. No disclaimer is intended. The following examples are being provided for nothing more than merely illustrative purposes. It is contemplated that the various teachings herein may be arranged and applied in numerous other ways. It is also contemplated that some variations may omit certain features referred to in the below examples. Therefore, none of the aspects or features referred to below should be deemed critical unless otherwise explicitly indicated as such at a later date by the inventors or by a successor in interest to the inventors. If any claims are presented in this application or in subsequent filings related to this application that include additional features beyond those referred to below, those additional features shall not be presumed to have been added for any reason relating to patentability.

Example 1

An apparatus (1402) comprising:
a first jaw (1404); and
a second jaw (1406) configured to cooperate with the first jaw (1404) to clamp and staple tissue with a plurality of staples, wherein the second jaw (1406) includes:
a jaw body (1408) extending longitudinally along a jaw body axis (1418);
a distal tip (1410A, 1410B) movably disposed distal to the jaw body (1408) and extending longitudinally along a distal tip axis (1420), wherein the distal tip (1410A, 1410B) is pivotable, about a pivot axis (1416) that extends transversely to the jaw body axis (1418), between a first discrete position and a second discrete position different from the first discrete position, wherein in the first discrete position the distal tip axis (1420) assumes a first orientation relative to the jaw body axis (1418), and in the second discrete position the distal tip axis (1420) assumes a second orientation relative to the jaw body axis (1418) different from the first orientation, wherein the distal tip (1410A, 1410B) includes a body (1412) which extends distal to the pivot axis (1416) and a protrusion (1414) which extends proximal to the pivot axis (1416) and wherein the body (1412) and protrusion (1414) move in opposing directions about the pivot axis (1416);
first and second stops (1602, 1702A, 1702B, 1702C) configured to constrain the pivotable motion of the distal tip (1410A, 1410B), the first stop (1602) positioned to abut a first portion (1604) of the distal tip when in the first discrete position and the second stop (1702A, 1702B, 1702C) positioned to abut a second portion (1704A, 1704B, 1704C) of the distal tip when in the second discrete position; and
a spring (1422) proximal to the proximal protrusion (1414) and configured to exert a resilient force against the proximal protrusion (1414) in a first direction so as to releasably bias the first portion (1604) of the distal tip (1410A, 1410B) against the first stop (1602) when in the first discrete position and exert the resilient force against the proximal protrusion (1414) in a second direction, different from the first direction, so as to releasably bias the second portion (1704A, 1704B, 1704C) against the second stop (1702A, 1702B, 1702C) when in the second discrete position, wherein as the distal tip (1410A, 1410B) is transitioned from one of the first or second discrete positions to the other of the first or second discrete positions, the direction of the resilient force of the spring (1422) exerted against the proximal protrusion (1414) transitions from one of the first and second directions to the other of the first and second directions.

Example 2

The apparatus of Example 1, wherein the first jaw (1404) comprises a staple cartridge (2102) that houses a plurality of staples and the second jaw (1406) comprises a plurality of staple forming pockets (1424) configured to form the staples, wherein the first and second jaws (1404, 1406) are configured to transition from an open state, wherein the first and second jaws (1404, 1406) are non-parallel, to a closed state, wherein the first and second jaws (1404, 1406) are nominally parallel, to clamp and staple tissue with the staples.

Example 3

The apparatus of Examples 2 or 3, wherein one of the first and second discrete positions is configured for marching the first and second jaws (1404, 1406) through tissue and the other of the first and second discrete positions is configured for gathering tissue between the first and second jaws (1404, 1406) when the first and second jaws (1404, 1406) are transitioned from the open state to the closed state.

Example 4

The apparatus of any of Examples 1-3, wherein when the distal tip is (1410A, 14010B) in the first orientation, the distal tip (1410A, 14010B) is nominally parallel to the jaw body axis (1418) and when in the second orientation, the distal tip (1410A, 14010B) is at an acute angle relative to the jaw body axis (1418).

Example 5

The apparatus of any of Examples 1-4, wherein the spring (1422) is further configured to, when the distal tip (1410A, 14010B) is positioned between the first and second discrete positions, rotatably bias the distal tip (1410A, 14010B) toward the closer of the first discrete position or the second discrete position.

Example 6

The apparatus of any of Examples 1-5, wherein the spring (1422) continuously exerts at least some amount of the resilient force against the proximal protrusion (1414).

Example 7

The apparatus of any of Examples 1-6, wherein the spring (1422) is configured to exert the resilient force against the proximal protrusion (1414) in a current direction until the distal tip (1410A, 14010B) is displaced, via the application of an external force to the body (1412) thereof, from its current orientation by a threshold amount.

Example 8

The apparatus of any of Examples 1-7, wherein the exertion against the proximal protrusion (1414) creates a resistance to the displacement of the distal tip (1410A, 14010B) and defines the threshold amount of external force and the transition of the direction of the resilient force exerted against the proximal protrusion (1414) between the first and second directions occurs abruptly upon the external force exceeding the threshold amount.

Example 9

The apparatus of any of Examples 1-8, wherein the first and second stops (1602, 1702A, 1702B, 1702C) are integrally formed in a distal end of the jaw body (1408).

Example 10

The apparatus of any of Examples 1-9, wherein the first and second stops (1602, 1702A, 1702B, 1702C) define an extent of a range of motion of the distal tip (1410A, 1410B).

Example 11

The apparatus of any of Examples 1-10, wherein the spring (1422) comprises a first spring arm (1426) having a proximal portion retained by the jaw body (1408) and a distal portion in contact with the proximal protrusion (1414).

Example 12

The apparatus of any of Examples 1-11, wherein the first spring arm (1426) comprises an upper surface (1606) and a lower surface (1608), a distal portion of the lower surface (1608) being in contact with the proximal protrusion (1414), the spring (1422) further comprising a second spring arm (1428) having a lower surface (1610), a distal portion of which contacts a distal portion of the upper surface (1606) of the first spring arm (1426) under load, the first and second spring arms (1426, 1428) exerting a combined spring force against the proximal protrusion (1414).

Example 13

The apparatus of any of Examples 1-12, wherein the spring (1422) further comprises a proximal portion (1430) which movably couples proximal ends of the first and second spring arms (1426, 1428) together.

Example 14

The apparatus of any of Examples 1-13, wherein the upper surface (1606) of the first spring arm (1426) is not in contact with the lower surface (1610) of the second spring arm (1428) when not under load.

Example 15

The apparatus of any of Examples 1-14, wherein the spring (1422) comprises a leaf spring having at least two stacked leaves, a lower surface of a lower leaf being in contact with the proximal protrusion (1414).

Example 16

The apparatus of any of Examples 1-15, wherein the proximal protrusion (1414) is characterized by a cam profile (1612) which controls the direction in which the spring (1422) exerts the resilient force against the proximal protrusion (1414).

30

Example 17

The apparatus of any of Examples 1-16, wherein the motion of the proximal protrusion (1414) caused by the transition of the distal tip (1710A, 1710B) between the first and second discrete positions causes the direction of the exertion of the resilient force against the proximal protrusion (1414) to change between the first and second directions.

Example 18

The apparatus of any of Examples 1-17, wherein the cam profile (1612) comprises first and second portions (1614, 1616), the first portion (1614) engaging the spring (1422) when the distal tip (1710A, 1710B) is in the first discrete position to cause the exertion of the resilient force against the proximal protrusion (1414) to be in the first direction, and the second portion (1616) engaging the spring (1422) when the distal tip (1710A, 1710B) is in the second discrete position to cause the exertion of the resilient force against the proximal protrusion (1414) to be in the second direction.

Example 19

The apparatus of any of Examples 1-18, wherein the jaw body (1408) further comprises a longitudinal channel (2104) along which at least a portion of a knife (2106) travels from a proximal end to a distal end of the jaw body (1408), the spring (1422) being positioned at the distal end of the jaw body (1408) and comprising a gap (2108) therein so that the travel of the knife (2106) to the distal end is not impeded thereby.

Example 20

The apparatus of any of Examples 1-20, wherein a distal end of the jaw body (1408 includes a cavity (1432) in which the spring (1422) is inserted, the spring (1422) including at least one portion (2110) which defines the extent of the insertion.

Example 21

A method of pivoting a distal tip (1410A, 1410B), about a pivot axis (1416) that extends transversely to a jaw body axis (1418) of a jaw body (1408) to which the distal tip (1410A, 1410B) is movably disposed at a distal end thereof and extending longitudinally along a distal tip axis (1420), between a first discrete position and a second discrete position different from the first discrete position, wherein in the first discrete position the distal tip axis (1420) assumes a first orientation relative to the jaw body axis (1418), and in the second discrete position the distal tip axis (1420) assumes a second orientation relative to the jaw body axis (1418) different from the first orientation, wherein the distal tip (1410A, 1410B) includes a body (1412) which extends distal to the pivot axis (1416) and a protrusion (1414) which extends proximal to the pivot axis (1416) and wherein the body (1412) and protrusion (1414) move in opposing directions about the pivot axis (1416), the method comprising: exerting a resilient force against the proximal protrusion (1414) in one of a first or second direction so as to releasably bias a first portion of the distal tip against one of a first stop (1602) positioned to abut a first portion (1604) of the distal tip (1410A, 1410B) when in the first discrete position and a second portion (1704A, 1704B, 1704C) of the distal tip (1410A, 1410B) against a second stop (1702A, 1702B,

1702C)), different from the first stop (1602), positioned to abut the second portion (1704A, 1704B, 1704C) of the distal tip (1410A, 1410B) when in the second discrete position; and transitioning the direction of the resilient force exerted against the proximal protrusion (1414) from one of the first and second directions to the other of the first and second directions as the distal tip (1410A, 1410B) transitions from one of the first or second discrete positions to the other of the first or second discrete positions.

Example 22

The method of Example 21, wherein when the distal tip (1410A, 1410B) is in the first orientation, the distal tip (1410A, 1410B) is nominally parallel to the jaw body axis (1408) and when in the second orientation, the distal tip (1410A, 1410B) is at an acute angle relative to the jaw body axis (1408).

Example 23

The method of Examples 21 or 22, further comprising rotatably biasing the distal tip (1410A, 1410B) toward the closer of the first discrete position or the second discrete position when the distal tip (1410A, 1410B) is positioned between the first and second discrete positions.

Example 24

The method of any of Examples 21-23, further comprising continuously exerting at least some amount of the resilient force against the proximal protrusion (1414).

Example 25

The method of any of Examples 21-24, further comprising exerting the resilient force against the proximal protrusion (1414) in a current direction until the distal tip (1410A, 1410B) is displaced, via the application of an external force to the body (1412) thereof, from its current orientation by a threshold amount.

Example 26

The method of any of Examples 21-25, wherein exerting comprises exerting a first amount of force against the proximal protrusion (1414) by a first spring arm (1426), of a spring (1422), having a proximal portion (1430) retained by the jaw body (1408) and a distal portion (1608) in contact with the proximal protrusion (1414), and exerting a second amount of force against at least the distal portion (1608) of the first spring arm (1426) by a distal portion (1610) of a second spring arm (1428), the resilient force exerted against the proximal protrusion (1414) being the combination of the first and second amounts of force.

Example 27

The method of any of Examples 21-26, further comprising controlling the direction in which the resilient force is exerted against the proximal protrusion (1414) using a cam profile (1612) of the proximal protrusion (1414).

Example 28

The method of any of Examples 21-27, further comprises applying an external force to the body (1412) of the distal tip (1410A, 1410B) to displace the distal tip (1410A, 1410B) from one of the first and second discrete positions to the other of the first and second discrete position, the displacement of the body (1412) opposably displacing the proximal protrusion (1414) causing the direction of the exertion of the resilient force against the proximal protrusion (1414) to change between the first and second directions.

Example 29

The method of any of Examples 21-28, wherein the cam profile (1612) comprises first and second portions (1614, 1616), the first portion (1614) causing, when the distal tip (1410A, 1410B) is in the first discrete position, the exertion of the resilient force against the proximal protrusion (1414) to be in the first direction, and the second portion causing, when the distal tip (1410A, 1410B) is in the second discrete position, the exertion of the resilient force against the proximal protrusion (1414) to be in the second direction.

Example 30

An apparatus (1402) comprising:
a first jaw (1404); and
a second jaw (1406) configured to cooperate with the first jaw (1404) to clamp and staple tissue with a plurality of staples, wherein the second jaw (1406) includes:
    a jaw body (1408) extending longitudinally along a jaw body axis (1418);
    a distal tip (1410A, 1410B) movably disposed distal to the jaw body (1408) and extending longitudinally along a distal tip axis (1416), wherein the distal tip (1410A, 1410B) is pivotable about a pivot axis (1416), that extends transversely to the jaw body axis (1418), between a first discrete position and a second discrete position different from the first discrete position, wherein in the first discrete position the distal tip axis (1416) assumes a first orientation relative to the jaw body axis (1418), and in the second discrete position the distal tip axis (1416) assumes a second orientation relative to the jaw body axis (1418) different from the first orientation, wherein the distal tip (1410A, 1410B) includes a body (1412) which extends distal to the pivot axis (1416) and a protrusion (1414) which extends proximal to the pivot axis (1416) and wherein the body (1412) and protrusion (1414) move in opposing directions about the pivot axis;
means for exerting a resilient force against the proximal protrusion (1414) in one of a first or second direction so as to releasably bias a first portion (1604) of the distal tip (1410A, 1410B) against one of a first stop (1602) positioned to abut the first portion (1604) of the distal tip (1410A, 1410B) when in the first discrete position and a second portion (1704A, 1704B, 1704C) of the distal tip (1410A, 1410B) against a second stop (1702A, 1702B, 1702C), different from the first stop (1602), positioned to abut the second portion (1704A, 1704B, 1704C) of the distal tip (1410A, 1410B) when in the second discrete position; and
means for transitioning the direction of the resilient force exerted against the proximal protrusion (1414) from one of the first and second directions to the other of the first and second directions as the distal tip (1410A, 1410B) transitions from one of the first or second discrete positions to the other of the first or second discrete positions.

Example 31

A method of manufacturing a jaw (1406) of an end effector (1402), the jaw (1406) comprising a jaw body (1408), the method comprising:

inserting a spring (1422) into a cavity (1432) formed in a distal end of the jaw body (1408);

affixing, pivotably, a distal tip (1410A, 1410B) to the distal end of the jaw body (1408), the distal tip (1410A, 1410B) comprising a protrusion (1414) proximal to a pivot axis (1416) which abuts and preloads the spring (1422) upon affixation of the distal tip (1410A, 1410B) to the distal end of the jaw body (1408), the spring (1422) thereafter exerting a resilient force against the proximal protrusion (1422) in a first direction so as to releasably bias a first portion (1604) of the distal tip (1410A, 1410B) against a first stop (1602) formed in the jaw body (1408) when in a first discrete position and exert the resilient force against the proximal protrusion (1414) in a second direction, different from the first direction, so as to releasably bias a second portion (1704A, 1704B, 1704C) against a second stop (1702A, 1702B, 1702C) formed in the jaw body (1408), different from the first stop (1602), when in a second discrete position.

Example 32

The method of Example 31, further comprising:

forming, prior to the inserting, the spring (1422) by folding a first spring arm (1426) over a second spring arm (1428) such that the first spring arm (1426) overlaps the second spring arm (1428), wherein upon the affixing, a portion of a lower surface (1608) of the first spring arm (1426) is in contact with the proximal protrusion (1414), and a portion of a lower surface (1610) of the second spring arm (1428) contacts a portion of an upper surface (1606) of the first spring arm (1426), the first and second spring arms (1426, 1428) exerting a combined spring force against the proximal protrusion (1414).

Example 33

The method of Examples 31 or 32, further comprising:

forming, prior to the affixing, a cam profile (1612) on the proximal protrusion (1414) of the distal tip (1410A, 1410B) which controls the direction in which the spring (1422) exerts the resilient force against the proximal protrusion 1414.

Example 34

An apparatus comprising:

a first jaw (1404); and a second jaw (1406) configured to cooperate with the first jaw (1404) to clamp and staple tissue with a plurality of staples, wherein the second jaw (1406) includes:

a jaw body (1408) extending longitudinally along a jaw body axis (1418);

a distal tip (1410B) movably disposed distal to the jaw body (1408) and extending longitudinally along a distal tip axis (1420), wherein the distal tip (1401B) is pivotable about a pivot axis (1416) which extends transversely to the jaw body axis (1418), the distal dip (1410B) being pivotable between at least a first discrete position and a second discrete position different from the first discrete position, wherein in the first discrete position the distal tip axis (1420) assumes a first orientation relative to the jaw body axis (1418), and in the second discrete position the distal tip axis (1420) assumes a second orientation relative to the jaw body axis (1418) different from the first orientation, wherein the distal tip (1410B) includes a body (1412) which extends distal to the pivot axis (1416);

a joint (4014) which pivotably connects a proximal portion of the distal tip (1410B) to a distal end of the jaw body (1408) and defines the pivot axis (1416), the joint characterized by a gap (4016A), into which tissue may ingress, between at least a portion the proximal portion of the distal tip (1410B) and at least a portion of the distal end of the jaw body (1408), the gap (4016A) having at least portion (4018) which is aligned with the jaw body axis (1408); and a cover (4302) which at least obstructs the gap (4016A) to prevent tissue ingress therein regardless of the position of the distal tip (1410B).

Example 35

The apparatus of Example 34, wherein the gap (4016A) comprises a further portion (4020) which is transverse to the jaw body axis (1408).

Example 36

The apparatus of Examples 34 or 35, wherein the cover (4302) is configured to resist displacement during movement of the distal tip (14010B).

Example 37

The apparatus of any of Examples 34-36, wherein the cover (4302) covers the joint (4014).

Example 38

The apparatus of any of Examples 34-37, wherein the cover (4302) extends distally to cover a proximal portion of the distal tip body (1412) and proximally to cover a distal portion of the jaw body (1408).

Example 39

The apparatus of any of Examples 34-38, wherein the cover (4302) comprises a heat shrinkable material wrapped around the proximal portion of the distal tip body (1412) and distal portion of the jaw body (1408).

Example 40

The apparatus of any of Examples 34-39, wherein the proximal portion of the distal tip body (1412) includes a recess (4304) in which the cover (4302) sits.

Example 41

The apparatus of any of Examples 34-40, wherein the cover (4302) comprises an elastic loop (4502) which is fitted in the recess (4304).

Example 42

The apparatus of any of Examples 34-41, wherein a distal portion of the cover (4302) sits in the recess (4304) of the distal tip body (1412), the jaw body (1408) further including a recess (4306) in which a proximal portion of the cover (4302) sits, the distal tip body and jaw body recesses (4304, 4306) configured to constrain the cover (4302).

Example 43

The apparatus of any of Examples 34-42, wherein the cover (4302) comprises elastic material (5002) formed on a proximal portion of the distal tip body (1412) which compresses against the distal end of the jaw body (1408) when the distal tip (1410A) is assembled to the jaw body (1408).

Example 44

A method of preventing tissue ingress into a gap (4016A), formed by a joint (4014) which pivotably connects a proximal portion of a distal tip (1410B) to a distal end of a jaw body (1408) such that the distal tip (1410B) is pivotable between at least a first discrete position and a second discrete position different from the first discrete position, wherein in the first discrete position a distal tip axis (1420) assumes a first orientation relative to a jaw body axis (1418), and in the second discrete position the distal tip axis (1420) assumes a second orientation relative to the jaw body axis (1418) different from the first orientation, the gap (4016A) being between at least a portion the proximal portion of the distal tip (1410A) and at least a portion of the distal end of the jaw body (1408), the gap (4016A) having at least portion (4018) which is aligned with the jaw body axis (1418), the method comprising:
    obstructing the gap (4016A) with a cover (4302) to prevent tissue ingress therein regardless of the position of the distal tip (1410B).

Example 45

The method of Example 44, further comprising affixing the cover (4302) in a recess (4304) formed in the proximal portion of a body (1412) of the distal tip (1410B).

Example 46

The apparatus of Examples 44 or 45, further comprising affixing a distal portion of the cover (4302) in the recess (4304) of the distal tip body (1412), and affixing a proximal portion of the cover (4302) in a recess (4306) formed in a distal end of the jaw body (1408), the distal tip body and jaw body recesses (4304, 4306) constraining the cover (4302).

Example 47

The apparatus of any of Examples 44-46, further comprises forming an elastic material (5002) on a proximal portion of the distal tip body (1412) and compressing the elastic material (5002) against the distal end of the jaw body (1408) when the distal tip (1410B) is assembled to the jaw body (1408).

Example 48

An apparatus for preventing tissue ingress into a gap (4016A), formed by a joint (4014) which pivotably connects a proximal portion of a distal tip (1410B) to a distal end of a jaw body (1408) such that the distal tip (1410B) is pivotable between at least a first discrete position and a second discrete position different from the first discrete position, wherein in the first discrete position a distal tip axis (1420) assumes a first orientation relative to a jaw body axis (1418), and in the second discrete position the distal tip axis (1420) assumes a second orientation relative to the jaw body axis (1418) different from the first orientation, the gap (4016A) being between at least a portion the proximal portion of a body (1412) of the distal tip (1410B) and at least a portion of the distal end of the jaw body (1408), the gap (4016A) having at least portion (4018) which is aligned with a jaw body axis (1418) of the jaw body (1408), the apparatus comprising:
    means for obstructing the gap (4016A) with a cover (4302) to prevent tissue ingress therein regardless of the position of the distal tip (1410B).

Example 49

A method of manufacturing a jaw (1406) of an end effector (1402), the jaw (1406) comprising a jaw body (1408), the method comprising:
    joining, pivotably, a proximal portion of a distal tip (1410B) to a distal end of the jaw body (1408) such that the distal tip (1410B) is pivotable between at least a first discrete position and a second discrete position different from the first discrete position, wherein in the first discrete position a distal tip axis (1420) assumes a first orientation relative to a jaw body axis (1418), and in the second discrete position the distal tip axis (1420) assumes a second orientation relative to the jaw body axis (1418) different from the first orientation, wherein the joining forms a gap (4016A) between at least a portion the proximal portion of the distal tip (1410B) and at least a portion of the distal end of the jaw body (1408), the gap (4016A) having at least portion (4018) which is aligned with a jaw body axis (1418) of the jaw body (1408); and
    obstructing the gap (4016A) with a cover (4302) to prevent tissue ingress therein regardless of the position of the distal tip (1410B).

Example 50

The method of Example 50, wherein the joining occurs at a joint (4014), the method further comprising covering the joint (4014) with the cover (4302).

Example 51

The method of Examples 49 or 50, further comprising extending the cover (4302) distally to cover a proximal portion of the distal tip (1410B) and proximally to cover a distal portion of the jaw body (1408).

Example 52

The method of any of Examples 49-51, wherein the cover (4302) comprises a heat shrinkable material, the method further comprising wrapping the heat shrinkable material around the proximal portion of the distal tip (1410B) and distal portion of the jaw body (1408) and applying heat thereto.

Example 53

The method of any of Examples 49-52, further comprising forming, at least prior to the obstructing, a recess (4304) in the proximal portion of the distal tip (1410B) configured to receive the cover (4302).

Example 54

The method of any of Examples 49-53, wherein the cover (4302) comprises an elastic loop (4502), the method comprising fitting the elastic loop (4502) in the recess (4304).

Example 55

The method of any of Examples 49-54, wherein the recess (4304) formed in the distal tip (1410B) is configured to receive a distal portion of the cover (4302), the method further comprising forming, at least prior to the obstructing, another recess (4306) in the jaw body (1408) configured to receive a proximal portion of the cover (4308), the distal tip and jaw body recesses (4304, 4306) configured to constrain the cover (4302).

Example 56

The method of any of Examples 49-55, further comprising forming, prior to the joining, the cover (4302), comprising an elastic material (5002), on a proximal portion of the distal tip (1410B) which compresses against the distal end of the jaw body (1408) when the distal tip (1410B) is joined to the jaw body (1408).

The following clauses also relate to various non-exhaustive ways in which the teachings herein may be combined or applied.

1. An apparatus comprising:
   a first jaw; and
   a second jaw configured to cooperate with the first jaw to clamp and staple tissue with a plurality of staples, wherein the second jaw includes:
   a jaw body extending longitudinally along a jaw body axis;
   a distal tip movably disposed distal to the jaw body and extending longitudinally along a distal tip axis, wherein the distal tip is pivotable, about a pivot axis that extends transversely to the jaw body axis, between a first discrete position and a second discrete position different from the first discrete position, wherein in the first discrete position the distal tip axis assumes a first orientation relative to the jaw body axis, and in the second discrete position the distal tip axis assumes a second orientation relative to the jaw body axis different from the first orientation, wherein the distal tip includes a body which extends distal to the pivot axis and a protrusion which extends proximal to the pivot axis and wherein the body and protrusion move in opposing directions about the pivot axis;
   first second stops configured to constrain the pivotable motion of the distal tip, the first stop positioned to abut a first portion of the distal tip when in the first discrete position and the second stop positioned to abut a second portion of the distal tip when in the second discrete position; and
   a spring proximal to the proximal protrusion and configured to exert a resilient force against the proximal protrusion in a first direction so as to releasably bias the first portion of the distal tip against the first stop when in the first discrete position and exert the resilient force against the proximal protrusion in a second direction, different from the first direction, so as to releasably bias the second portion against the second stop when in the second discrete position, wherein as the distal tip is transitioned from one of the first or second discrete positions to the other of the first or second discrete positions, the direction of the resilient force of the spring exerted against the proximal protrusion transitions from one of the first and second directions to the other of the first and second directions.

2. The apparatus of claim 1, wherein the first jaw comprises a staple cartridge that houses a plurality of staples and the second jaw comprises a plurality of staple forming pockets configured to form the staples, wherein the first and second jaws are configured to transition from an open state, wherein the first and second jaws are non-parallel, to a closed state, wherein the first and second jaws are nominally parallel, to clamp and staple tissue with the staples.

3. The apparatus of claim 2, wherein one of the first and second discrete positions is configured for marching the first and second jaws through tissue and the other of the first and second discrete positions is configured for gathering tissue between the first and second jaws when the first and second jaws are transitioned from the open state to the closed state.

4. The apparatus of claim 1, wherein when the distal tip is in the first orientation, the distal tip is nominally parallel to the jaw body axis and when in the second orientation, the distal tip is at an acute angle relative to the jaw body axis.

5. The apparatus of claim 1, wherein the spring is further configured to, when the distal tip is positioned between the first and second discrete positions, rotatably bias the distal tip toward the closer of the first discrete position or the second discrete position.

6. The apparatus of claim 1, wherein the spring continuously exerts at least some amount of the resilient force against the proximal protrusion.

7. The apparatus of claim 1, wherein the spring is configured to exert the resilient force against the proximal protrusion in a current direction until the distal tip is displaced, via the application of an external force to the body thereof, from its current orientation by a threshold amount.

8. The apparatus of claim 7, wherein the exertion against the proximal protrusion creates a resistance to the displacement of the distal tip and defines the threshold amount of external force and the transition of the direction of the resilient force exerted against the proximal protrusion between the first and second directions occurs abruptly upon the external force exceeding the threshold amount.

9. The apparatus of claim 1, wherein the first and second stops are integrally formed in a distal end of the second jaw body.

10. The apparatus of claim 1, wherein the first and second stops define an extent of a range of motion of the distal tip.

11. The apparatus of claim 1, wherein the spring comprises a first spring arm having a proximal portion retained by the jaw body and a distal portion in contact with the proximal protrusion.

12. The apparatus of claim 11, wherein the first spring arm comprises an upper surface and a lower surface, a distal portion of the lower surface being in contact with the proximal protrusion, the spring further comprising a second spring arm having a lower surface, a distal portion of which contacts a distal portion of the upper surface of the first spring arm under load, the first and second spring arms exerting a combined spring force against the proximal protrusion.

13. The apparatus of claim 12, wherein the spring further comprises a proximal portion which movably couples proximal ends of the first and second spring arms together.

14. The apparatus of claim 13, wherein the upper surface of the first spring arm is not in contact with the lower surface of the second spring arm when not under load.

15. The apparatus of claim 1, wherein the spring comprises a leaf spring having at least two stacked leaves, a lower surface of a lower leave being in contact with the proximal protrusion.

16. The apparatus of claim 1, wherein the proximal protrusion is characterized by a cam profile which controls the direction in which the spring exerts the resilient force against the proximal protrusion.

17. The apparatus of claim 16, wherein the motion of the proximal protrusion caused by the transition of the distal tip between the first and second discrete positions causes the direction of the exertion of the resilient force against the proximal protrusion to change between the first and second directions.

18. The apparatus of claim 16, wherein the cam profile comprises first and second portions, the first portion engaging the spring when the distal tip is in the first discrete position to cause the exertion of the resilient force against the proximal protrusion to be in the first direction, and the second portion engaging the spring when the distal tip is in the second discrete position to cause the exertion of the resilient force against the proximal protrusion to be in the second direction.

19. The apparatus of claim 1, wherein the jaw body further comprises a longitudinal channel along which at least a portion of a knife travels from a proximal end to a distal end of the jaw body, the spring being positioned at the distal end of the jaw body and comprising a gap therein so that the travel of the knife to the distal end is not impeded thereby.

20. The apparatus of claim 1, wherein a distal end of the jaw body includes a cavity in which the spring is inserted, the spring including at least one portion which defines the extent of the insertion.

21. A method of pivoting a distal tip, about a pivot axis that extends transversely to a jaw body axis of a jaw body to which the distal tip is movably disposed at a distal end thereof, between a first discrete position and a second discrete position different from the first discrete position, wherein in the first discrete position the distal tip axis assumes a first orientation relative to the jaw body axis, and in the second discrete position the distal tip axis assumes a second orientation relative to the jaw body axis different from the first orientation, wherein the distal tip includes a body which extends distal to the pivot axis and a protrusion which extends proximal to the pivot axis and wherein the body and protrusion move in opposing directions about the pivot axis, the method comprising:

exerting a resilient force against the proximal protrusion in one of a first or second direction so as to releasably bias a first portion of the distal tip against one of a first stop positioned to abut a first portion of the distal tip when in the first discrete position and a second portion of the distal tip against a second stop, different from the first stop, positioned to abut the second portion of the distal tip when in the second discrete position; and transitioning the direction of the resilient force of the spring exerted against the proximal protrusion from one of the first and second directions to the other of the first and second directions as the distal tip transitions from one of the first or second discrete positions to the other of the first or second discrete positions.

22. The method of claim 21, wherein when the distal tip is in the first orientation, the distal tip is nominally parallel to the jaw body axis and when in the second orientation, the distal tip is at an acute angle relative to the jaw body axis.

23. The method of claim 21, further comprising rotatably biasing the distal tip toward the closer of the first discrete position or the second discrete position when the distal tip is positioned between the first and second discrete positions.

24. The method of claim 21, further comprising continuously exerting at least some amount of the resilient force against the proximal protrusion.

25. The method of claim 21, further comprising exerting the resilient force against the proximal protrusion in a current direction until the distal tip is displaced, via the application of an external force to the body thereof, from its current orientation by a threshold amount.

26. The method of claim 21, wherein exerting comprises exerting a first amount of force against the proximal protrusion by a first spring arm having a proximal portion retained by the jaw body and a distal portion in contact with the proximal protrusion, and exerting a second amount of force against at least the distal portion of the first spring arm by a distal portion of a second spring arm, the resilient force exerted against the proximal protrusion being the combination of the first and second amounts of force.

27. The method of claim 21, further comprising controlling the direction in which the resilient force is exerted against the proximal protrusion using a cam profile of the proximal protrusion.

28. The method of claim 27, further comprises applying an external force to the body of the distal tip to displace the distal tip from one of the first and second discrete positions to the other of the first and second discrete position, the displacement of body opposably displacing the distal protrusion causing the direction of the exertion of the resilient force against the proximal protrusion to change between the first and second directions.

29. The method of claim 27, wherein the cam profile comprises first and second portions, the first portion engaging the spring when the distal tip is in the first discrete position to cause the exertion of the resilient force against the proximal protrusion to be in the first direction, and the second portion engaging the spring when the distal tip is in the second discrete position to cause the exertion of the resilient force against the proximal protrusion to be in the second direction.

30. An apparatus comprising:

a first jaw; and a second jaw configured to cooperate with the first jaw to clamp and staple tissue with a plurality of staples, wherein the second jaw includes:

a jaw body extending longitudinally along a jaw body axis;

a distal tip movably disposed distal to the jaw body and extending longitudinally along a distal tip axis, wherein the distal tip is pivotable about a pivot axis, that extends transversely to the jaw body axis, between a first discrete position and a second discrete position different from the first discrete position, wherein in the first discrete position the distal tip axis assumes a first orientation relative to the jaw body axis, and in the second discrete position the distal tip axis assumes a second orientation relative to the jaw body axis different from the first orientation, wherein the distal tip includes a body which extends distal to the pivot axis and a protrusion which extends proximal to the pivot axis and wherein the body and protrusion move in opposing directions about the pivot axis;

means for exerting a resilient force against the proximal protrusion in one of a first or second direction so as to releasably bias a first portion of the distal tip against one of a first stop positioned to abut a first portion of the distal tip when in the first discrete position and a second portion of the distal tip against a second stop, different from the first stop, positioned to abut the second portion of the distal tip when in the second discrete position; and means for transitioning the direction of the resilient force of the spring exerted against the proximal protrusion from one of the first and second directions to the other of the first and second directions as the distal tip transitions from one of the first or second discrete positions to the other of the first or second discrete positions.

31. A method of manufacturing a jaw of an end effector, the jaw comprising a jaw body, the method comprising:
   inserting a spring into a cavity formed in a distal end of the jaw body;
   affixing, pivotably, a distal tip to the distal end of the jaw body, the distal tip comprising a portion proximal to a pivot axis which abuts and preloads the spring upon affixation of the distal tip to the distal end of the jaw body, the spring thereafter exerting a resilient force against the proximal protrusion in a first direction so as to releasably bias the first portion of the distal tip against a first stop formed in the jaw body when in a first discrete position and exert the resilient force against the proximal protrusion in a second direction, different from the first direction, so as to releasably bias the second portion against a second stop formed in the jaw body, different from the first stop, when in a second discrete position.

32. The method of claim 31, further comprising:
   forming, prior to the inserting, the spring by folding a first spring arm over a second spring arm such that the first spring arm overlaps the second spring arm, wherein upon the affixing, a portion of the lower surface of the second spring arm is in contact with the proximal protrusion, and a portion of a lower surface of the first spring arm contacts a portion of an upper surface of the second spring arm, the first and second spring arms exerting a combined spring force against the proximal protrusion.

33. The method of claim 31, further comprising:
   forming, prior to the affixing, a cam profile on the proximal portion of the distal tip which controls the direction in which the spring exerts the resilient force against the proximal protrusion.

The following clauses also relate to various non-exhaustive ways in which the teachings herein may be combined or applied.

1. An apparatus comprising:
   a first jaw; and
   a second jaw configured to cooperate with the first jaw to clamp and staple tissue with a plurality of staples, wherein the second jaw includes:
      a jaw body extending longitudinally along a jaw body axis;
      a distal tip movably disposed distal to the jaw body and extending longitudinally along a distal tip axis, wherein the distal tip is pivotable about a pivot axis which extends transversely to the jaw body axis, the distal dip being pivotable between at least a first discrete position and a second discrete position different from the first discrete position, wherein in the first discrete position the distal tip axis assumes a first orientation relative to the jaw body axis, and in the second discrete position the distal tip axis assumes a second orientation relative to the jaw body axis different from the first orientation, wherein the distal tip includes a body which extends distal to the pivot axis;
   a joint which pivotably connects a proximal portion of the distal tip to a distal end of the jaw body and defines the pivot axis, the joint characterized by a gap, into which tissue may ingress, between at least a portion the proximal portion of the distal tip and at least a portion of the distal end of the jaw body, the gap having at least portion which is aligned with the jaw body axis; and
   a cover which at least obstructs the gap to prevent tissue ingress therein regardless of the position of the distal tip.

2. The apparatus of claim 1, wherein the gap comprises a further portion which is transverse to the jaw body axis.

3. The apparatus of claim 1, wherein the cover is configured to resist displacement during movement of the distal tip.

4. The apparatus of claim 1, wherein the cover covers the joint.

5. The apparatus of claim 4, wherein the cover extends distally to cover a proximal portion of the distal tip body and proximally to cover a distal portion of the jaw body.

6. The apparatus of claim 1, wherein the cover comprises a heat shrinkable material wrapped around the proximal portion of the distal tip body and distal portion of the jaw body.

7. The apparatus of claim 1, wherein the proximal portion of the distal tip includes a recess in which the cover sits.

8. The apparatus of claim 7, wherein the cover comprises an elastic loop which is fitted in the recess.

9. The apparatus of claim 7, wherein a distal portion of the cover sits in the recess of the distal tip, the jaw body further including a recess in which a proximal portion of the cover sits, the distal tip and jaw body recesses configured to constrain the cover.

10. The apparatus of claim 1, wherein the cover comprises elastic material formed on a proximal portion of the distal tip body which compresses against the distal end of the jaw body when the distal tip is assembled to the jaw body.

11. A method of preventing tissue ingress into a gap, formed by a joint which pivotably connects a proximal portion of a distal tip to a distal end of a jaw body such that the distal tip is pivotable between at least a first discrete position and a second discrete position different from the first discrete position, wherein in the first discrete position the distal tip axis assumes a first orientation relative to the jaw body axis, and in the second discrete position the distal tip axis assumes a second orientation relative to the jaw body axis different from the first orientation, the gap being between at least a portion the proximal portion of the distal tip and at least a portion of the distal end of the jaw body, the gap having at least portion which is aligned with a jaw body axis of the jaw body, the method comprising:
  obstructing the gap with a cover to prevent tissue ingress therein regardless of the position of the distal tip.

12. The method of claim 11, further comprising affixing the cover in a recess formed in the proximal portion of the distal tip.

13. The apparatus of claim 12, further comprising affixing a distal portion of the cover in the recess of the distal tip, and affixing a proximal portion of the cover in a recess formed in a distal end of the jaw body, the distal tip and jaw body recesses constraining the cover.

14. The apparatus of claim 11, further comprises forming an elastic material on a proximal portion of the distal tip body and compressing the elastic material against the distal end of the jaw body when the distal tip is assembled to the jaw body.

15. An apparatus for preventing tissue ingress into a gap, formed by a joint which pivotably connects a proximal portion of a distal tip to a distal end of a jaw body such that the distal tip is pivotable between at least a first discrete position and a second discrete position different from the first discrete position, wherein in the first discrete position the distal tip axis assumes a first orientation relative to the jaw body axis, and in the second discrete position the distal tip axis assumes a second orientation relative to the jaw body axis different from the first orientation, the gap being between at least a portion the proximal portion of the distal tip and at least a portion of the distal end of the jaw body, the gap having at least portion which is aligned with a jaw body axis of the jaw body, the apparatus comprising:
  means for obstructing the gap with a cover to prevent tissue ingress therein regardless of the position of the distal tip.

16. A method of manufacturing a jaw of an end effector, the jaw comprising a jaw body, the method comprising:
  joining, pivotably, a proximal portion of a distal tip to a distal end of the jaw body such that the distal tip is pivotable between at least a first discrete position and a second discrete position different from the first discrete position, wherein in the first discrete position the distal tip axis assumes a first orientation relative to the jaw body axis, and in the second discrete position the distal tip axis assumes a second orientation relative to the jaw body axis different from the first orientation, wherein the joint forms a gap between at least a portion the proximal portion of the distal tip and at least a portion of the distal end of the jaw body, the gap having at least portion which is aligned with a jaw body axis of the jaw body; and
  obstructing the gap with a cover to prevent tissue ingress therein regardless of the position of the distal tip.

17. The method of claim 16 further comprising covering the joint with the cover.

18. The method of claim 17, further comprising extending the cover distally to cover a proximal portion of the distal tip body and proximally to cover a distal portion of the jaw body.

19. The method of claim 16, wherein the cover comprises a heat shrinkable material, the method further comprising wrapping the heat shrinkable material around the proximal portion of the distal tip body and distal portion of the jaw body and applying heat thereto.

20. The method of claim 16, further comprising forming, at least prior to the obstructing, a recess in the proximal portion of the distal tip configured to receive the cover.

21. The method of claim 20, wherein the cover comprises an elastic loop, the method comprising fitting the elastic loop in the recess.

22. The method of claim 20, wherein the recess formed in the distal tip is configured to receive a distal portion of the cover, the method further comprising forming, at least prior to the obstructing, another recess in the jaw body configured to receive a proximal portion of the cover, the distal tip and jaw body recesses configured to constrain the cover.

23. The method of claim 16, further comprising forming, prior to the joining, the cover, comprising an elastic material, on a proximal portion of the distal tip which compresses against the distal end of the jaw body when the distal tip is joined to the jaw body.

VII. Miscellaneous

It should be understood that any one or more of the teachings, expressions, embodiments, examples, etc. described herein may be combined with any one or more of the other teachings, expressions, embodiments, examples, etc. that are described herein. The above-described teachings, expressions, embodiments, examples, etc. should therefore not be viewed in isolation relative to each other. Various suitable ways in which the teachings herein may be combined will be readily apparent to those of ordinary skill in the art in view of the teachings herein. Such modifications and variations are intended to be included within the scope of the claims.

Furthermore, any one or more of the teachings herein may be combined with any one or more of the teachings disclosed in U.S. patent application Ser. No. 18/588,147, entitled "Surgical Stapler Cartridge Having Intermediate Raised Tissue Engagement Protrusions," filed on Feb. 27, 2024; U.S. patent application Ser. No. 18/588,175, entitled "Surgical Stapler Cartridge Having Tissue Engagement Protrusions with Enlarged Engagement Surface," filed on Feb. 27, 2024; U.S. patent application Ser. No. 18/588,206, entitled "Surgical Stapler Cartridge Having Raised Surface to Promote Buttress Adhesion," filed on Feb. 27, 2024; U.S. patent application Ser. No. 18/588,240, entitled "Surgical Stapler Cartridge Having Cartridge Retention Features," filed on Feb. 27, 2024; U.S. patent application Ser. No. 18/588,269, entitled "Surgical Stapler Anvil Having Staple Forming Pockets with Laterally Varying Orientations," filed on Feb. 27, 2024; U.S. patent application Ser. No. 18/588,684, entitled "Method of Surgical Stapling," filed on Feb. 27, 2024; and/or U.S. patent application Ser. No. 18/588,094, entitled "Incompatible Staple Cartridge Use Prevention Features for Surgical Stapler," filed on Feb. 27, 2024.

Additionally, any one or more of the teachings herein may be combined with any one or more of the teachings disclosed in U.S. Pat. App. No. 63/459,739, entitled "Surgical Stapler Anvil Having Staple Forming Pockets with Laterally Varying Orientations," filed on Apr. 17, 2023. The disclosure of each of these U.S. patent applications is incorporated by reference herein in its entirety.

Additionally, any one or more of the teachings herein may be combined with any one or more of the teachings disclosed in U.S. Pat. No. 11,304,697, entitled "Surgical Stapler with Deflectable Distal Tip," issued Apr. 19, 2022, the disclosure of which is incorporated by reference herein, in its entirety; U.S. Pat. No. 11,317,912, entitled "Surgical Stapler with Rotatable Distal Tip," issued May 3, 2022, the disclosure of which is incorporated by reference herein, in its entirety; and/or U.S. Pat. No. 11,439,391, entitled "Surgical Stapler with Toggling Distal Tip," issued Sep. 13, 2022, the disclosure of which is incorporated by reference herein, in its entirety.

It should be appreciated that any patent, publication, or other disclosure material, in whole or in part, that is said to be incorporated by reference herein is incorporated herein only to the extent that the incorporated material does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

Versions of the devices described above may have application in conventional medical treatments and procedures conducted by a medical professional, as well as application in robotic-assisted medical treatments and procedures. By way of example only, various teachings herein may be readily incorporated into a robotic surgical system such as those made available by Auris Health, Inc. of Redwood City, CA or by Intuitive Surgical, Inc., of Sunnyvale, California.

Versions of the devices described above may be designed to be disposed of after a single use, or they can be designed to be used multiple times. Versions may, in either or both cases, be reconditioned for reuse after at least one use. Reconditioning may include any combination of the steps of disassembly of the device, followed by cleaning or replacement of particular pieces, and subsequent reassembly. In particular, some versions of the device may be disassembled, and any number of the particular pieces or parts of the device may be selectively replaced or removed in any combination. Upon cleaning and/or replacement of particular parts, some versions of the device may be reassembled for subsequent use either at a reconditioning facility, or by a user immediately prior to a procedure. Those skilled in the art will appreciate that reconditioning of a device may utilize a variety of techniques for disassembly, cleaning/replacement, and reassembly. Use of such techniques, and the resulting reconditioned device, are all within the scope of the present application.

By way of example only, versions described herein may be sterilized before and/or after a procedure. In one sterilization technique, the device is placed in a closed and sealed container, such as a plastic or TYVEK bag. The container and device may then be placed in a field of radiation that can penetrate the container, such as gamma radiation, x-rays, or high-energy electrons. The radiation may kill bacteria on the device and in the container. The sterilized device may then be stored in the sterile container for later use. A device may also be sterilized using any other technique known in the art, including but not limited to beta or gamma radiation, ethylene oxide, or steam.

Having shown and described various embodiments of the present invention, further adaptations of the methods and systems described herein may be accomplished by appropriate modifications by one of ordinary skill in the art without departing from the scope of the present invention. Several of such potential modifications have been mentioned, and others will be apparent to those skilled in the art. For instance, the examples, embodiments, geometrics, materials, dimensions, ratios, steps, and the like discussed above are illustrative and are not required. Accordingly, the scope of the present invention should be considered in terms of the following claims and is understood not to be limited to the details of structure and operation shown and described in the specification and drawings.

We claim:

1. An apparatus comprising:

a first jaw; and a second jaw configured to cooperate with the first jaw to clamp and staple tissue with a plurality of staples, wherein the second jaw includes:

a jaw body extending longitudinally along a jaw body axis;

a distal tip movably disposed distal to the jaw body and extending longitudinally along a distal tip axis, wherein the distal tip is pivotable, about a pivot axis that extends transversely to the jaw body axis, between a first discrete position and a second discrete position different from the first discrete position, wherein the distal tip includes a body which extends distal to the pivot axis and a protrusion which extends proximal to the pivot axis;

first and second stops configured to constrain the pivotable motion of the distal tip, the first stop positioned to abut a first portion of the distal tip when in the first discrete position and the second stop positioned to abut a second portion of the distal tip when in the second discrete position; and a spring proximal to the proximal protrusion and configured to exert a resilient force against the proximal protrusion in a first direction so as to releasably bias the first portion of the distal tip against the first stop when in the first discrete position and exert the resilient force against the proximal protrusion in a second direction, different from the first direction, the second direction being substantially aligned with the second discrete position, so as to releasably bias the second portion against the second stop when in the second discrete position, wherein as the distal tip is transitioned from one of the first or second discrete positions to the other of the first or second discrete positions, the direction of the resilient force of the spring exerted against the proximal protrusion transitions from one of the first and second directions to the other of the first and second directions; and wherein the first and second stops are integrally formed in a distal end of the second jaw body.

2. The apparatus of claim 1, wherein the first jaw comprises a staple cartridge that houses a plurality of staples and the second jaw comprises a plurality of staple forming pockets configured to form the staples, wherein the first and second jaws are configured to transition from an open state, wherein the first and second jaws are non-parallel, to a closed state, wherein the first and second jaws are nominally parallel, to clamp and staple tissue with the staples.

3. The apparatus of claim 2, wherein one of the first and second discrete positions is configured for marching the first and second jaws through tissue and the other of the first and second discrete positions is configured for gathering tissue between the first and second jaws when the first and second jaws are transitioned from the open state to the closed state.

4. The apparatus of claim 1, wherein when the distal tip is in the first discrete position, the distal tip is nominally parallel to the jaw body axis and when in the second discrete position, the distal tip is at an acute angle relative to the jaw body axis.

5. The apparatus of claim 1, wherein the spring is further configured to, when the distal tip is positioned between the first and second discrete positions, rotatably bias the distal tip toward the closer of the first discrete position or the second discrete position.

6. The apparatus of claim 1, wherein the spring continuously exerts at least some amount of the resilient force against the proximal protrusion.

7. The apparatus of claim 1, wherein the spring is configured to exert the resilient force against the proximal protrusion in a current direction until the distal tip is displaced, via the application of an external force to the body thereof, from its current discrete position by a threshold amount.

8. The apparatus of claim 7, wherein the exertion against the proximal protrusion creates a resistance to the displacement of the distal tip and defines the threshold amount of external force and the transition of the direction of the resilient force exerted against the proximal protrusion between the first and second directions occurs abruptly upon the external force exceeding the threshold amount.

9. The apparatus of claim 1, wherein the first and second stops define an extent of a range of motion of the distal tip.

10. The apparatus of claim 1, wherein the proximal protrusion is characterized by a cam profile which controls the direction in which the spring exerts the resilient force against the proximal protrusion.

11. The apparatus of claim 10, wherein the motion of the proximal protrusion caused by the transition of the distal tip between the first and second discrete positions causes the direction of the exertion of the resilient force against the proximal protrusion to change between the first and second directions.

12. The apparatus of claim 10, wherein the cam profile comprises first and second portions, the first portion engaging the spring when the distal tip is in the first discrete position to cause the exertion of the resilient force against the proximal protrusion to be in the first direction, and the second portion engaging the spring when the distal tip is in the second discrete position to cause the exertion of the resilient force against the proximal protrusion to be in the second direction.

13. An apparatus comprising:
a first jaw; and
a second jaw configured to cooperate with the first jaw to clamp and staple tissue with a plurality of staples, wherein the second jaw includes:
a jaw body extending longitudinally along a jaw body axis;
a distal tip movably disposed distal to the jaw body and extending longitudinally along a distal tip axis, wherein the distal tip is pivotable, about a pivot axis that extends transversely to the jaw body axis, between a first discrete position and a second discrete position different from the first discrete position, wherein the distal tip includes a body which extends distal to the pivot axis and a protrusion which extends proximal to the pivot axis;
first and second stops configured to constrain the pivotable motion of the distal tip, the first stop positioned to abut a first portion of the distal tip when in the first discrete position and the second stop positioned to abut a second portion of the distal tip when in the second discrete position; and
a spring proximal to the proximal protrusion and configured to exert a resilient force against the proximal protrusion in a first direction so as to releasably bias the first portion of the distal tip against the first stop when in the first discrete position and exert the resilient force against the proximal protrusion in a second direction, different from the first direction, so as to releasably bias the second portion against the second stop when in the second discrete position, wherein as the distal tip is transitioned from one of the first or second discrete positions to the other of the first or second discrete positions, the direction of the resilient force of the spring exerted against the proximal protrusion transitions from one of the first and second directions to the other of the first and second directions; and
wherein the spring comprises a first spring arm having a proximal portion retained by the jaw body and a distal portion in contact with the proximal protrusion; and
wherein the first spring arm comprises an upper surface and a lower surface, a distal portion of the lower surface being in contact with the proximal protrusion, the spring further comprising a second spring arm having a lower surface, a distal portion of which contacts a distal portion of the upper surface of the first spring arm under load, the first and second spring arms exerting a combined spring force against the proximal protrusion.

14. The apparatus of claim 13, wherein the spring further comprises a proximal portion which movably couples proximal ends of the first and second spring arms together.

15. The apparatus of claim 14, wherein the upper surface of the first spring arm is not in contact with the lower surface of the second spring arm when not under load.

16. The apparatus of claim 13, wherein the spring comprises a leaf spring having at least two stacked leaves, a lower surface of a lower leaf being in contact with the proximal protrusion.

17. The apparatus of claim 13, wherein the jaw body further comprises a longitudinal channel along which at least a portion of a knife travels from a proximal end to a distal end of the jaw body, the spring being positioned at the distal end of the jaw body and comprising a gap therein so that the travel of the knife to the distal end is not impeded thereby.

18. The apparatus of claim 13, wherein a distal end of the jaw body includes a cavity in which the spring is inserted, the spring including at least one portion which defines the extent of the insertion.

19. A method of pivoting a distal tip, about a pivot axis that extends transversely to a jaw body axis of a jaw body to which the distal tip is movably disposed at a distal end thereof, between a first discrete position and a second discrete position different from the first discrete position, wherein the distal tip includes a body which extends distal to the pivot axis and a protrusion which extends proximal to the pivot axis, the method comprising:
exerting a resilient force against the proximal protrusion in one of a first or second direction, the second direction being different from the first direction, the second direction being substantially aligned with the second discrete position, so as to releasably bias, when the resilient force is exerted in the first direction, a first portion of the distal tip against one of a first stop integrally formed in a distal end of the second jaw body and positioned to abut a first portion of the distal tip when in the first discrete position and, when the resilient force is exerted in the second direction, a second portion of the distal tip against a second stop, different from the first stop, integrally formed in the distal end of the second jaw body and positioned to abut the second portion of the distal tip when in the second discrete position; and transitioning the direction of the resilient force of the spring exerted against the proximal protrusion from one of the first and second directions to the other of the first and second directions as the distal tip transitions from one of the first or second discrete positions to the other of the first or second discrete positions.

20. The method of claim 19, wherein when the distal tip is in the first discrete position, the distal tip is nominally parallel to the jaw body axis and when in the second discrete position, the distal tip is at an acute angle relative to the jaw body axis.

21. The method of claim 19, further comprising rotatably biasing the distal tip toward the closer of the first discrete position or the second discrete position when the distal tip is positioned between the first and second discrete positions.

22. The method of claim 19, further comprising continuously exerting at least some amount of the resilient force against the proximal protrusion.

23. The method of claim 19, further comprising exerting the resilient force against the proximal protrusion in a current direction until the distal tip is displaced, via the application of an external force to the body thereof, from its current discrete position by a threshold amount.

24. The method of claim 19, wherein exerting comprises exerting a first amount of force against the proximal protrusion by a first spring arm having a proximal portion retained by the jaw body and a distal portion in contact with the proximal protrusion, and exerting a second amount of force against at least the distal portion of the first spring arm by a distal portion of a second spring arm, the resilient force exerted against the proximal protrusion being the combination of the first and second amounts of force.

25. The method of claim 19, further comprising controlling the direction in which the resilient force is exerted against the proximal protrusion using a cam profile of the proximal protrusion.

26. The method of claim 25, further comprises applying an external force to the body of the distal tip to displace the distal tip from one of the first and second discrete positions to the other of the first and second discrete A position, the displacement of body displacing the distal protrusion causing the direction of the exertion of the resilient force against the proximal protrusion to change between the first and second directions.

27. The method of claim 25, wherein the cam profile comprises first and second portions, the first portion engaging the spring when the distal tip is in the first discrete position to cause the exertion of the resilient force against the proximal protrusion to be in the first direction, and the second portion engaging the spring when the distal tip is in the second discrete position to cause the exertion of the resilient force against the proximal protrusion to be in the second direction.

50

28. An apparatus comprising:
a first jaw; and
a second jaw configured to cooperate with the first jaw to clamp and staple tissue with a plurality of staples, wherein the second jaw includes:
   a jaw body extending longitudinally along a jaw body axis;
   a distal tip movably disposed distal to the jaw body and extending longitudinally along a distal tip axis, wherein the distal tip is pivotable about a pivot axis, that extends transversely to the jaw body axis, between a first discrete position and a second discrete position different from the first discrete position, wherein the distal tip includes a body which extends distal to the pivot axis and a protrusion which extends proximal to the pivot axis;
means for exerting a resilient force against the proximal protrusion in one of a first or second direction different from the first direction so as to, when the resilient force is exerted in the first direction, releasably bias a first portion of the distal tip against one of a first stop integrally formed in a distal end of the second jaw body and positioned to abut a first portion of the distal tip when in the first discrete position and, when the resilient force is exerted in the second direction, releasably bias a second portion of the distal tip against a second stop, different from the first stop, integrally formed in the distal end of the second jaw body and positioned to abut the second portion of the distal tip when in the second discrete position; and
means for transitioning the direction of the resilient force of the spring exerted against the proximal protrusion from one of the first and second directions to the other of the first and second directions as the distal tip transitions from one of the first or second discrete positions to the other of the first or second discrete positions.

29. A method of manufacturing a jaw of an end effector, the jaw comprising a jaw body, the method comprising:
   inserting a spring into a cavity formed in a distal end of the jaw body;
   affixing, pivotably, a distal tip to the distal end of the jaw body, the distal tip comprising a portion proximal to a pivot axis which abuts and preloads the spring upon affixation of the distal tip to the distal end of the jaw body, the spring thereafter exerting a resilient force against the proximal protrusion in a first direction so as to releasably bias the first portion of the distal tip against a first stop formed in the jaw body when in a first discrete position and exert the resilient force against the proximal protrusion in a second direction, different from the first direction, the second direction being substantially aligned with the second discrete position, so as to releasably bias the second portion against a second stop formed in the jaw body, different from the first stop, when in a second discrete position.

30. The method of claim 29, further comprising:
   forming, prior to the inserting, the spring by folding a first spring arm over a second spring arm such that the first spring arm overlaps the second spring arm, wherein upon the affixing, a portion of the lower surface of the second spring arm is in contact with the proximal protrusion, and a portion of a lower surface of the first spring arm contacts a portion of an upper surface of the second spring arm, the first and second spring arms exerting a combined spring force against the proximal protrusion.

31. The method of claim 29, further comprising:

forming, prior to the affixing, a cam profile on the proximal portion of the distal tip which controls the direction in which the spring exerts the resilient force against the proximal protrusion.

* * * * *